(12) United States Patent
Naughton et al.

(10) Patent No.: US 9,360,509 B2
(45) Date of Patent: Jun. 7, 2016

(54) NANOSCALE SENSORS WITH NANOPOROUS MATERIAL

(75) Inventors: Michael J. Naughton, Chestnut Hill, MA (US); Dong Cai, West Newton, MA (US); Binod Rizal, Brighton, MA (US); Thomas Chiles, Norfolk, MA (US); Huaizhou Zhao, Brighton, MA (US)

(73) Assignee: Trustees of Boston College, Chestnut Hill, MA (US)

( * ) Notice: Subject to any disclaimer, the term of this patent is extended or adjusted under 35 U.S.C. 154(b) by 281 days.

(21) Appl. No.: 14/005,205

(22) PCT Filed: Mar. 21, 2012

(86) PCT No.: PCT/US2012/029962
§ 371 (c)(1),
(2), (4) Date: Sep. 25, 2013

(87) PCT Pub. No.: WO2012/129314
PCT Pub. Date: Sep. 27, 2012

(65) Prior Publication Data
US 2014/0015548 A1    Jan. 16, 2014

Related U.S. Application Data

(60) Provisional application No. 61/454,870, filed on Mar. 21, 2011.

(51) Int. Cl.
*G01R 27/26*  (2006.01)
*G01N 27/327*  (2006.01)
*H01L 21/00*  (2006.01)
*C12Q 1/00*  (2006.01)
*B82Y 15/00*  (2011.01)
*B82Y 30/00*  (2011.01)

(52) U.S. Cl.
CPC ........ *G01R 27/2605* (2013.01); *G01N 27/3278* (2013.01); *G01R 27/26* (2013.01); *B82Y 15/00* (2013.01); *B82Y 30/00* (2013.01); *C12Q 1/00* (2013.01); *H01L 21/00* (2013.01); *H01L 2221/00* (2013.01); *Y10T 29/49124* (2015.01)

(58) Field of Classification Search
CPC ...... H01L 21/00; H01L 2221/00; C12Q 1/00; C12Q 2304/00; A61B 1/00; A61B 17/00; A61B 2217/00; A61B 2218/00; B03C 1/00; B03C 2201/00
See application file for complete search history.

(56) References Cited

U.S. PATENT DOCUMENTS 5,049,741 A    9/1991  Fukuda et al.
5,869,973 A    2/1999  Nosov
(Continued)

FOREIGN PATENT DOCUMENTS

WO    WO-2010/006877    1/2010

OTHER PUBLICATIONS

International Search Report of PCT/US2012/029962 dated Oct. 5, 2012.

*Primary Examiner* — Huy Q Phan
*Assistant Examiner* — Temilade Rhodes-Vivour
(74) *Attorney, Agent, or Firm* — Joseph M. Noto; Bond, Schoeneck & King PLLC

(57) ABSTRACT

A nanocoaxial sensor includes an outer conductor, an inner conductor, a nanoporous dielectric material disposed between the outer and inner conductors, a nanocavity sized to allow target species to enter the nanocavity between the outer and inner conductors.

36 Claims, 34 Drawing Sheets

(56) References Cited

U.S. PATENT DOCUMENTS

| | | | |
|---|---|---|---|
| 6,000,287 A * | 12/1999 | Menzel | 73/514.32 |
| 6,335,690 B1 * | 1/2002 | Konchin et al. | 340/618 |
| 7,042,224 B2 | 5/2006 | Fujiwara | |
| 7,335,908 B2 * | 2/2008 | Samuelson | B82Y 10/00 257/12 |
| 2003/0134267 A1 | 7/2003 | Kang et al. | |
| 2003/0164048 A1 | 9/2003 | Shkel | |
| 2004/0023253 A1 | 2/2004 | Kunwar et al. | |
| 2004/0036484 A1 * | 2/2004 | Tamai | 324/663 |
| 2004/0085080 A1 * | 5/2004 | Schilowitz et al. | 324/698 |
| 2004/0125266 A1 * | 7/2004 | Miyauchi | B01L 3/502761 349/57 |
| 2006/0279905 A1 | 12/2006 | Chow et al. | |
| 2007/0132043 A1 * | 6/2007 | Bradley et al. | 257/414 |
| 2007/0178477 A1 | 8/2007 | Joiner et al. | |
| 2008/0268288 A1 * | 10/2008 | Jin | B81C 1/00031 428/800 |
| 2010/0080954 A1 * | 4/2010 | Mohseni | G03F 7/20 428/131 |

* cited by examiner

FIG. 15A  FIG. 15B  FIG. 15C  FIG. 15D
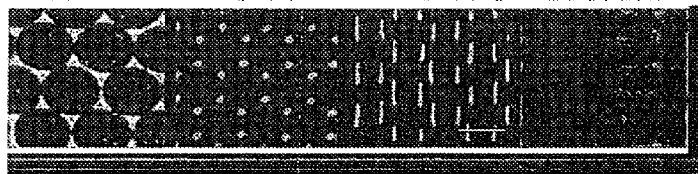
Spatial Amplification
$$V_{total} = \sum_{i=1}^{N} V_i$$
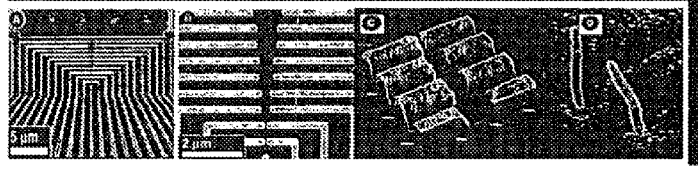
Addressing/Multiplexing
$$V = |v_{ij}|$$
for $i=1,2,...,n \wedge j=1,2,...,m$
FIG. 16A  FIG. 16B  FIG. 16C  FIG. 16D
Physical selectivity
$$V = v \cdot f_{(d)}$$
$$f_{(d)} = \begin{cases} g_{(d)} & d \leq D_0 \\ 0 & d = other \end{cases}$$
FIG. 17

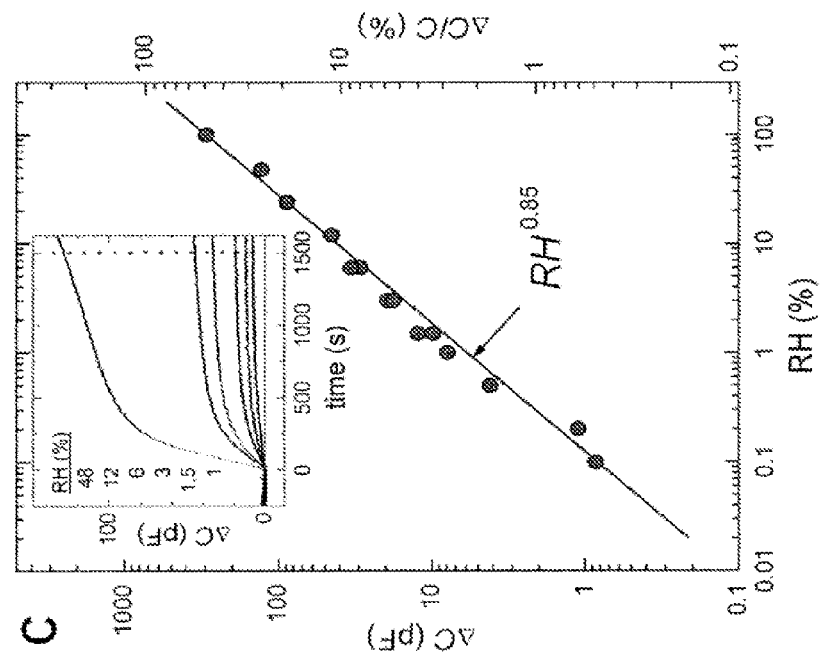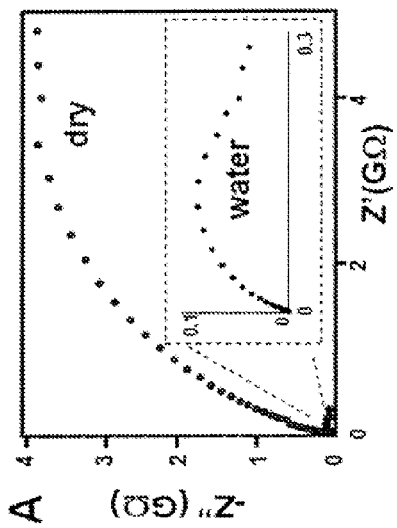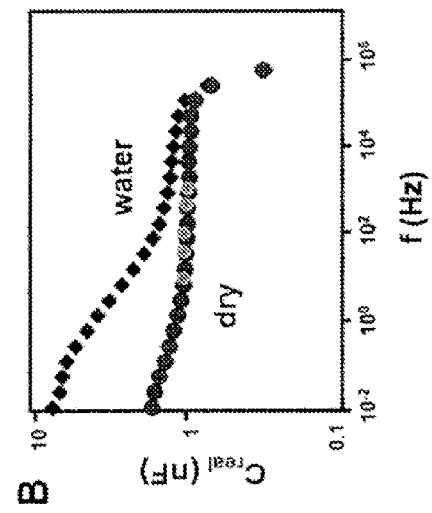
FIGs. 20A-C

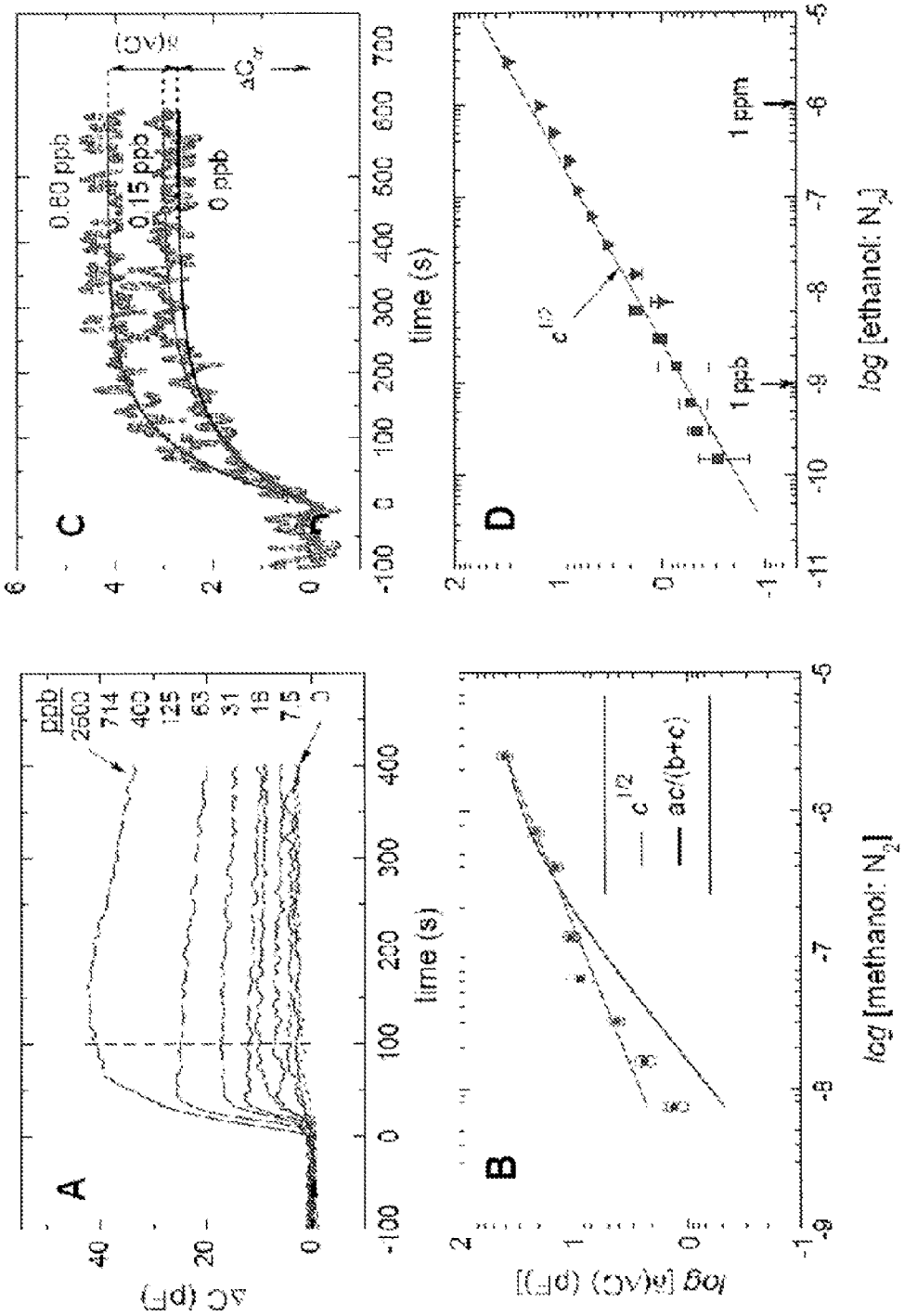
FIG 21A-D

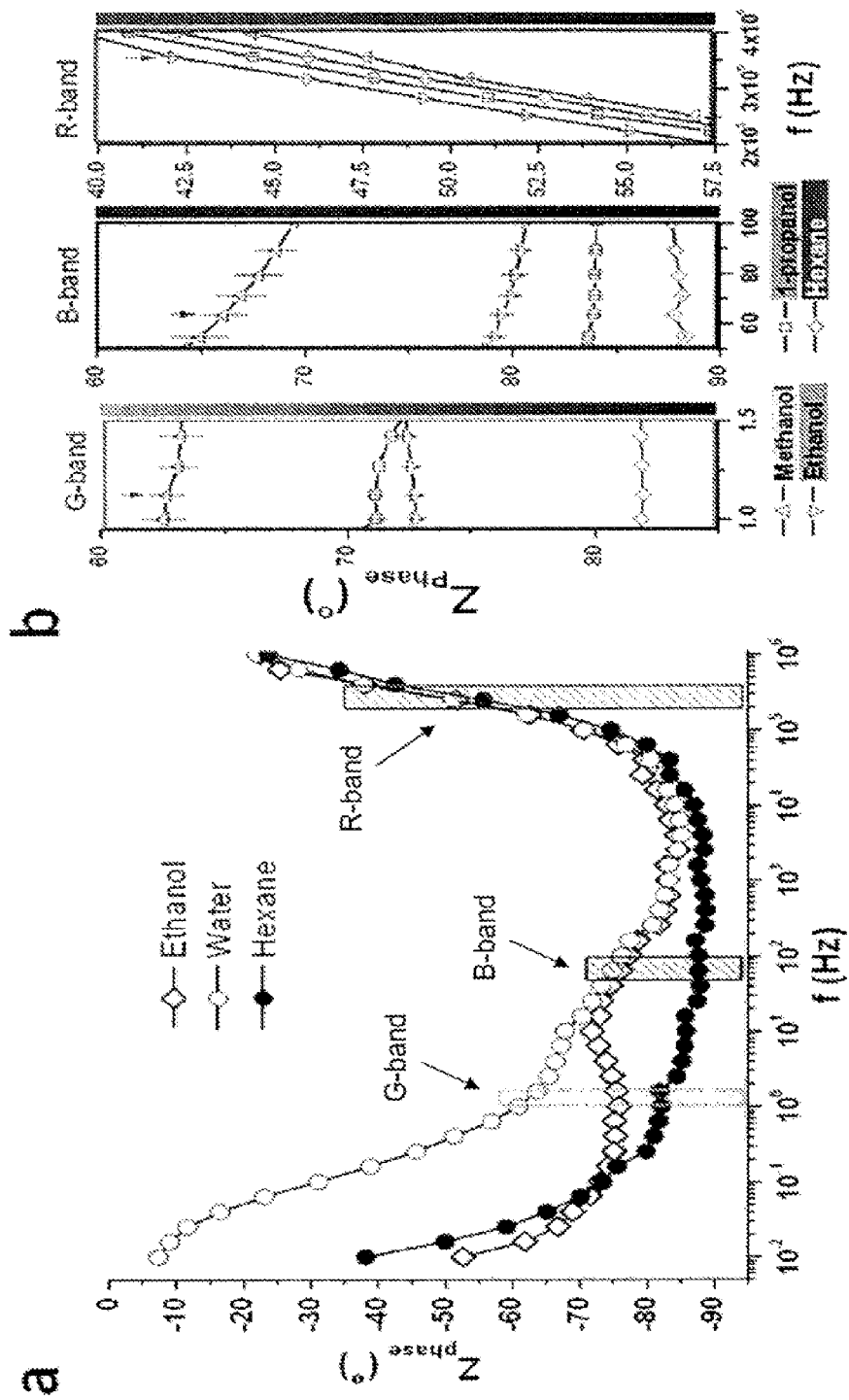
FIG 22A-B

NANOSCALE SENSORS WITH NANOPOROUS MATERIAL

CROSS-REFERENCE TO RELATED PATENT APPLICATIONS

This application is the U.S. National Stage of International Patent Application No. PCT/US2012/029962, filed Mar. 21, 2012, which claims the benefit of U.S. Provisional Patent Application No. 61/454,870 filed Mar. 21, 2011, the entire contents of which are incorporated by reference herein. The subject matter of this application is also related to U.S. Provisional Patent Application No. 60/859,735, filed Nov. 17, 2006; U.S. patent application Ser. No. 12/514,689, filed Nov. 17, 2007; and International Patent Application No. PCT/US2010/023068, filed Mar. 2, 2010, the entire contents of each of which is incorporated herein by reference in its entirety.

STATEMENT REGARDING FEDERALLY-SPONSORED RESEARCH OR DEVELOPMENT

This invention was made with Government Support under Contract Number PHY-0804718 awarded by the National Science Foundation and Contract Number CA137681 awarded by the Department of Health and Human Services. The Government has certain rights in the invention.

BACKGROUND

The present invention relates generally to the field of nanoscale sensors, and more particularly to an apparatus and method for detecting a target species using nanoscale sensors.

Chemical and biological sensors typically operate at elevated temperatures to enhance chemical reactivity, and often require long recovery times (if recoverable at all), poor reproducibility, and are applicable to the detection of a very limited range of chemical and biological species and are described in U.S. Pat. No. 7,013,708, entitled "Carbon Nanotube Sensors"; U.S. Pat. No. 7,166,325, entitled "Carbon Nanotube Devices"; U.S. Application Publication No. 2003/0134267, entitled "Sensor for Detecting Biomolecule Using Carbon Nanotubes"; U.S. Application Publication No. 2004/0245209, entitled "Method for Fabricating a Carbon Nanotube Array and a Biochip Using the Self-Assembly of Supramolecules and Staining of Metal Compound"; U.S. Application Publication No. 2005/0181409, entitled "Biochip and Biomolecular Detection System Using the Same"; and U.S. Patent Application Publication No. 2005/0230270, entitled "Carbon Nanotube Nanoelectrode Arrays."

An article by Choi et al., entitled "YY1-DNA interaction results in a significant change of electronic context as measured by capacitance," *Biophysical Chemistry* 103, 109-115 (2003), which is incorporated herein by reference in its entirety, describes a nanosensor that detects a dielectric change upon the formation of a specific Yin-Yang 1 (YY1)-DNA complex within an 80-nm gap between two electrodes of a capacitor. Aliquots of a mixture of YY1 and P5 promoter DNA were placed on the capacitor and, after a 5-min incubation period, the capacitance was measured between 10 kHz and 3 MHz. Changes in the capacitance were attributed to the specific YY1-DNA complexation. It is believed that the dielectric effect is due to the alignment of dipoles to the electric field of the capacitor, whereby a stronger dipole results in greater capacitance. However, the sensitivity of the device suffered due to signal contributions arising from complexation and other contributions outside of the electrode gap.

SUMMARY

One embodiment of the invention provides a nanosensor that includes a capacitor having a nanocavity between a first and second conductor of the capacitor. The nanosensor is adapted to exhibit each of: a size-dependent physical selection of target species entering into the nanocavity, a selective capture of at least one of the target species within the nanocavity to at least one of the first and second conductors; and an electromagnetic shielding within the nanocavity such that a signal produced in response to the selective capture within the nanocavity is substantially undisturbed by a capture outside of the nanocavity.

Another embodiment of the invention provides a nanocoaxial sensor that includes an outer conductor, an inner conductor, and a nanocavity sized to allow target species to enter the nanocavity between the outer and inner conductors. Some embodiments include an active sensing element immobilized within the nanocavity on at least one of the inner or outer conductors. The active sensing element is adapted to selectively capture at least one of the target species.

Another embodiment of the invention provides a method of making a nanocoaxial sensor. The method includes providing an array of vertically-aligned electrically conducting nanostructures which extend substantially perpendicular to a substrate, wherein each nanostructure is circumferentially surrounded by a dielectric material disposed within a metal cylinder, and forming at least one nanocavity by removing at least a portion of the dielectric material located on a side of the array opposite the substrate.

Another embodiment of the invention provides a method of using a nanosensor to detect a presence of a target species. The method includes transmitting electromagnetic waves through a medium disposed between a first and second electrode of the nanosensor, wherein the first and second electrodes comprise an inter-electrode spacing of no more than about 500 nm and the waves are substantially shielded by the first and second electrodes, and monitoring for a change in the electromagnetic waves based on a change in a dielectric constant between the first and second electrodes, wherein the change in the dielectric constant corresponds to the presence of the target species between the first and second electrodes.

In some aspects, the present disclosure relates to an apparatus, or a nanosensor for sensing the presence of target species. The nanosensor may comprise a capacitor having a space between a first and second conductor of the capacitor. The space may be at least partially filled with a nanoporous dielectric material. The nanosensor may produce a signal in response to the capture of a target species in the space.

In some embodiments, the nanosensor is adapted to exhibit: a size-dependent physical selection of target species entering into the space, a selective capture of at least one of the target species within the space to at least one of the first and second conductors and/or the nanoporous dielectric material.

Some embodiments feature an electromagnetic shielding within the space such that a signal produced in response to a selective capture within the space is substantially undisturbed by a capture outside of the space.

In further embodiments, the size-dependent physical selection is performed by an opening to a nanocavity in the space that prevents species having a size greater than a critical size from entering into the nanocavity. In further embodiments, the size comprises a distance between the first and second conductors.

In some embodiments, the signal produced in response to the capture comprises a change in the complex impedance (e.g., capacitance and/or conductance) of the capacitor. In further embodiments, the nanosensor device may comprise a nanocoaxial capacitor. The first conductor may comprise an outer conductor of the nanocoaxial capacitor. The inner conductor may comprise an inner conductor of the nanocoaxial capacitor. In some embodiments, the nanosensor further comprises a nanoporous dielectric material disposed between the inner and outer conductors, wherein the inner conductor comprises a nano fiber (or a metallic or metallic coated nanopillar), and the outer conductor comprises a metal. In further embodiments, the nanosensor comprises an etched nanocavity in at least a portion of the dielectric material. In some embodiments, the nanoporous material substantially fills the nanocavity. In further embodiments, the nanosensor comprises at least one active sensing element immobilized on a portion of the nanoporous dielectric, the at least one active sensing element may be adapted to selectively capture the at least one target species. In still further embodiments, the at least one target species comprises an antigen, the at least one active sensing element comprises an antibody, and the selective capture comprises a specific binding of the antigen with the antibody.

In some embodiments, the nanofiber comprises a carbon nanotube (or a gold nanowire, any metallic nanowire, a heavily doped semiconductor nanowire, a nonmetallic nanopillar coated with a metal, etc.), the metal comprises at least one of: nickel, aluminum, titanium, gold, platinum, and chromium, and the dielectric material comprises at least one of: $Al_2O_3$, $SiO_2$, MgO, $Si_3N_4$, $TiO_2$, and a non-conductive polymer. The carbon nanotube may comprise a multi-walled carbon nanotube, the metal may comprise chromium, and the dielectric material may comprise $Al_2O_3$.

The nanosensor may comprise the outer conductor circumferentially surrounding the inner conductor. In some embodiments, a space between the outer and inner conductors running along substantially the entire length of the inner conductor is substantially filled with dielectric material. The nanosensor may comprise an unfilled nanocavity located at one end of the nanosensor between the inner and outer conductors. The outer conductor may comprise a cylinder and the inner conductor may comprise a nanofiber. In some embodiments, the inner conductor is about 40 nm to about 200 nm in diameter; and the nanocavity is about 50 nm to about 2,000 nm in depth measured from the one end of the nanosensor. In certain embodiments, the inner conductor is in electrical contact with a metal layer deposited on at least a portion of a substrate and the inner conductor is elongated in a direction substantially perpendicular to the substrate. In further embodiments, the outer conductor is not in electrical contact with the metal layer. In some embodiments, the nanosensor comprises a layer of nonporous dielectric material located adjacent to the inner conductor. The nanoporous material may have a porosity of at least 10% by volume. In some embodiments, the nanoporous material has an average pore size of 50 nm or less.

In some aspects, the present disclosure relates to a sensor array. The sensor array may comprise a plurality of sensors. Each of the plurality of sensors may comprise a nanosensor described herein. The sensor array may comprise an ordered pattern of the sensors on a substrate. The ordered pattern may comprise a hexagonal pattern. In some embodiments, the sensor array comprises an inner conductor of at least one sensor that is not in electrical contact with the inner conductor of at least one other sensor. In further embodiments, the sensor array comprises an insulating material disposed between the outer conductors of adjacent nanosensors.

In some aspects, the present disclosure relates to a method of making a sensor. The method may comprise a step of providing an array of vertically-aligned (e.g., conducting) nanostructures prepared (e.g., grown) substantially perpendicular to a substrate, wherein each nanostructure is circumferentially surrounded by an at least partially nanoporous dielectric material disposed within a conductive cylinder.

In some embodiments, at least one nanocavity may be formed by removing at least a portion of the dielectric material located on a side of the array opposite the substrate. In certain embodiments, each conductive cylinder is circumferentially surrounded by an insulative material. In further embodiments, the array on the side opposite the substrate is polished, wherein the step of polishing is performed before the step of forming the at least one nanocavity. In some embodiments, at least one nanoporous surface of the dielectric material is functionalized. In further embodiments, the method comprises a step of removing a portion of material comprises partially etching the dielectric material on the polished side of the array. In yet further embodiments, the nanostructures comprise carbon fibers (or metal coated polymer nanopillars); the metal cylinders comprise at least one of nickel, aluminum, titanium, gold, platinum, and chromium; and the dielectric material comprises at least one of $Al_2O_3$, $SiO_2$, MgO, $Si_3N_4$, $TiO_2$, and a non-conductive polymer. In still further embodiments, the dielectric material comprises $Al_2O_3$; the carbon fibers comprise carbon nanotubes. In some embodiments the polymer nanopillars comprise SU-8 polymer coated with a metal, such as gold.

In some aspects, the present disclosure relates to a method of using a nanosensor to detect a presence of a target specie. The method may comprise a step of applying an alternating electric potential between a first and second electrode of the nanosensor and monitoring the complex dielectric impedance (capacitance and conductance) response of the circuit.

The method may comprise a step of transmitting electromagnetic waves through a nanoporous dielectric medium disposed between a first and second electrode of the nanosensor, wherein the first and second electrodes comprise an interelectrode spacing of no more than about 500 nm and the waves are substantially shielded between the first and second electrodes. The method may also comprise the step of monitoring for a change in the electromagnetic waves based on a change in a dielectric constant between the first and second electrodes, wherein the change in the dielectric constant corresponds to a selective capture of a target specie between the first and second electrodes.

In some embodiments, the electromagnetic waves comprise an oscillating electromagnetic field. The step of monitoring may comprise a step of using at least one of Impedance Spectroscopy or Time Domain Dielectric Spectroscopy to measure at least one of impedance or dielectric constant between the first and second electrodes as a function of frequency of the field, and the frequency is swept over a range of about 1 Hz to about 10 GHz. In further embodiments, the frequency is swept over a range of about 1 Hz to about 10 MHz. In still further embodiments, the frequency is swept over a range of about 1 MHz to about 10 GHz. In some embodiments, the electromagnetic waves are transmitted through the medium in a transverse electromagnetic mode. The step of monitoring may comprise measuring at least one of intensity or wavelength of the transmitted waves. The electromagnetic waves may comprise visible light. The first and second electrode may each comprise a coplanar layer of a nanoscale coplanar transmission line, and the medium may comprise a dielectric layer disposed between the coplanar layers. In some embodiments, the first electrode comprises an outer conductor of a nanoscale coaxial transmission line, the second electrode comprises an outer conductor of the nanoscale coaxial transmission line, and the medium comprises a nanoporous dielectric layer disposed between the inner and outer conductors. In certain embodiments, the nanosensor comprises a nanocavity formed between the inner and outer conductors.

In various embodiments, the sensors described herein may be used to detect any suitable analyte, including organic and inorganic compounds. In some embodiments, the a biomolecule, The biomolecule may include nucleic acids (DNA, RNA, etc.), proteins, polysaccharides, lipids, phospholipids, vitamins, hormones, metabolites, carbohydrates, peptides, heavy metal binding complexes, toxins (e.g., neurotoxins), etc.

BRIEF DESCRIPTION OF THE DRAWINGS

FIG. 2A shows a schematic view and an exemplary view of a carbon nanotube. FIG. 2B shows a schematic view and an exemplary view of the carbon nanotube in FIG. 2A after coating with a dielectric material. FIG. 2C shows a schematic view and an exemplary view of the carbon nanotube in FIG. 2B after coating with an outer conductor material.

FIG. 5 shows a nanoscale coaxial transmission line array according to an embodiment of the present invention.

FIG. 6A shows a high-resolution optical microscope image of white light reflected from the nanoscale coaxial transmission line medium. FIG. 6B shows a high-resolution optical microscope image of white light transmitted through the medium. FIG. 6C is an SEM image of the nanoscale coaxial transmission line medium surface (tilted 45 deg). FIGS. 6A-6C have the same magnification. FIG. 6D shows an image of a laser beam with λ=532 nm transmitted through a glass substrate (exposure time 0.0025 sec). FIG. 6E shows an image of a laser beam with λ=532 nm transmitted through the nanoscale coaxial transmission line medium on the same glass substrate (exposure time 1 sec). FIG. 6F shows an image of a laser beam with λ=680 nm transmitted through a glass substrate (exposure time 0.0025 sec). FIG. 6G shows an image of a laser beam with λ=680 nm transmitted through the nanoscale coaxial transmission line medium on the same glass substrate (exposure time 1 sec). FIGS. 6D-6G have the same magnification.

FIG. 7D shows a plot of measured intensity of the transmitted light at fixed wavelength (λ=532 nm) versus sample thickness.

FIG. 15A-15D are SEM images showing the steps used to fabricate an array of nanocoaxial sensors according to an embodiment of the present invention.

FIG. 16A-16D show an individually-addressable array of nanocoaxial sensors according to an embodiment of the present invention.

FIG. 17 are SEM images showing the tunability of the size of the nanocavity openings of the nanocoaxial sensors according to an embodiment of the present invention.

FIG. 18A is a schematic diagram of an experimental setup used to nucleate a gold film. FIG. 18B is a plot of resistivity versus temperature of the gold film. FIG. 18C shows the steps of a method for functionalizing CNTs with gold nanoparticles according to an embodiment of the present invention.

FIG. 20 A-C shows results of nanoporous nanosensors.

FIG. 21A-D shows results of nanoporous nanosensors.

FIG. 22 A-B shows results of nanoporous nanosensors in various solutions.

Figure 1A:
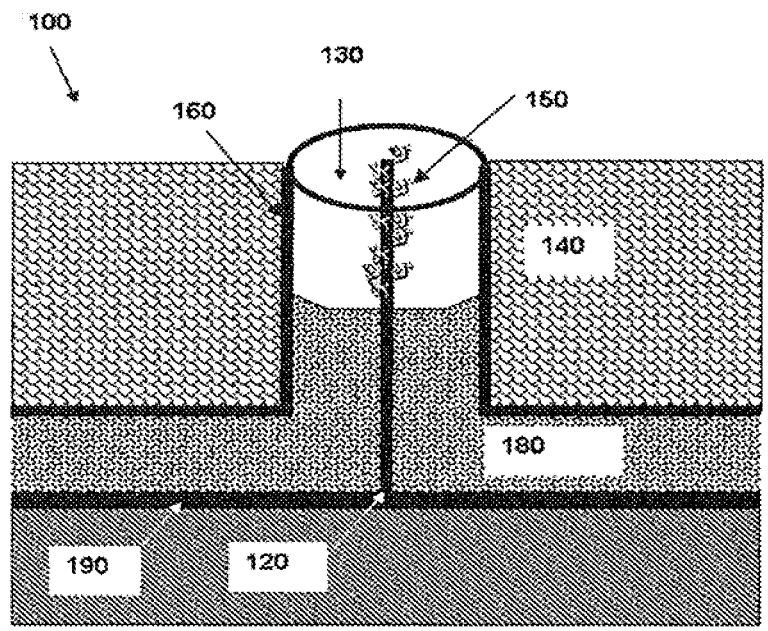
FIG. 1A shows a schematic image of a nanoscale sensor unit structure according to an embodiment of the present invention.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The embodiments disclosed herein relate to the field of nanoscale sensors, and more particularly to an apparatus and method for ultrasensitive sensing of target species, such as chemical and/or biological molecules, using nanoscale sensors. Methods of fabricating a nanoscale sensor apparatus are also disclosed. The nanoscale sensors are able to capture the real-time signals from a single target species. The nanoscale sensors may be used in various biomedical related applications including, but not limited to, clinic diagnosis, bio-attack alarming system, drinking water monitoring, biomolecule characterization in research, constructing an artificial neuronal post-synaptic membrane, food quality test, allergic species detection, forensic examination, and personnel biological identification. The nanoscale sensors may be used in various non-biomedical areas including, but not limited to, explosive detection, narcotics control, and pollution monitoring.

The basic elements of nanoscale capacitance sensor measurements are disclosed. The nanoscale sensors are used to detect particles of bio-species, for example, with ultrasensitivity that affords single molecule detection. The nanoscale sensor unit structure comprises a dielectric material located between a first electrical conductor and a second electrical conductor. The nanoscale sensor unit structure constitutes a nanoscale capacitor and forms a nanoscale coaxial transmission line built around an internal conductor with the diameter registered at any value between about 1 nm and about 1000 nm, such as about 40 nm to about 200 nm, for example about 100 nm. Biomolecules, or biologically active sensing elements, are immobilized either on the first conductor or the second conductor, or both.

The following definitions are used to describe the various aspects and characteristics of the presently disclosed embodiments.

As used herein, "nanostructures" and "nanostructure materials" refer to a broad class of materials, with microstructures modulated in zero to three dimensions on length scales less than about 1,000 nm; materials with atoms arranged in nano-sized clusters, which become the constituent grains or building blocks of the material; and any material with at least one dimension in the about 1-1,000 nm range. Using a variety of synthesis methods, it is possible to produce nanostructured materials in the following forms: nanorods, nanowires, nanopillars, nanofibers, nanotubes, nanohorns, thin films, coatings, powders and as a bulk material. In an embodiment, the material comprising the nanostructure is carbon. In an embodiment, the material comprising the nanostructure need not be carbon. In applications where symmetric structures are generated, the sizes (largest dimensions) can be as large as tens of microns.

As used herein, "carbon nanotubes" and "CNTs" are used interchangeably. These terms primarily refer to a type of carbon nanofiber having cylindrical carbon molecules. CNTs may have unique properties that make them potentially useful in a wide variety of applications in nanotechnology, electronics, optics, and other fields of materials science. They exhibit extraordinary strength and unique electrical properties, and are efficient conductors of heat.

As used herein, "single-walled carbon nanotubes" (SWCNTs) are made of one graphene sheet rolled into a cylinder. "Double-walled carbon nanotubes" (DWCNTs) are made of two graphene sheets in parallel, and those with multiple sheets (typically about 3 to about 30) are "multi-walled carbon nanotubes" (MWCNTs). For the coaxial nanostructures disclosed herein, MWCNTs need not be specifically graphitic (i.e. crystalline graphene) in structure, but can be fibrous. MWCNTs are a type of carbon nanotube, and carbon nanotubes are a type of carbon nanofiber.

As used herein, a CNT is "vertically aligned" when its longitudinal axis is oriented substantially perpendicular to a substrate on which the CNT's proximal end is in contact, for example the substrate from which the CNT is grown. CNTs may be vertically aligned even if they are not exactly perpendicular to the substrate and even if they are curved or kinked.

As used herein, a "tubule" is an individual CNT.

As used herein, "linear CNTs" refer to CNTs that do not contain any branches originating from the surface of individual CNT tubules along their linear axes.

As used herein, "conductor" refers to an electrically conducting material. A conductor may be a metallic or non-metallic material.

As used herein CNTs have a "uniform length" wherein the length of individual tubules are substantially the same length relative to one another. Depending on growth conditions used, the height of a CNT in an array in a given growth run can be varied in height by about 10% to about 50%. Alternatively, height uniformity is accomplished by performing additional mechanical polish steps. In an embodiment, the CNTs have a uniform length from about 1 to about 50 micrometers.

As used herein, the "aspect ratio" of a CNT is the ratio of tubule length and tubule diameter.

The CNTs have "proximal" and "distal" ends. The proximal ends of the CNTs engage a substrate.

As used herein, a "nanoscale coaxial transmission line" refers to a nanoscale coaxial wire, which includes a plurality of concentric layers. In an embodiment, the nanoscale coaxial transmission line has three concentric layers: an internal conductor, a dielectric material around the internal conductor, and an outer conductor. Transmission of electromagnetic energy inside the coaxial line is wavelength-independent and happens in transverse electromagnetic (TEM) mode. In an embodiment, the internal conductor is a metallic core. In an embodiment, the outer conductor is a metallic shielding that increases the signal-to-noise ratio of the detected signal.

As used herein, a "nanoscale coplanar line" refers to a nanoscale coplanar structure, which includes a plurality of parallel layers. In an embodiment, the nanoscale coplanar line has three parallel layers: two metallic conductors, with a dielectric coating between them. Transmission of electromagnetic energy inside the coplanar line is wavelength-independent and happens in transverse electromagnetic (TEM) mode.

As used herein, "transverse electromagnetic (TEM)" refers to an electromagnetic mode in a transmission line for which both the electric and magnetic fields are perpendicular to the direction of propagation. Other possible modes include but are not limited to transverse electric (TE), in which only the electric field is perpendicular to the direction of propagation, and transverse magnetic (TM), in which only the magnetic field is perpendicular to the direction of propagation.

As used herein, "nano-optics" is the study of optical interactions with matter on a subwavelength scale, i.e., nanoscale optics.

As used herein, an "optical signal" refers to any electromagnetic radiation pulse including gamma rays, X-rays, ultraviolet light, visible light, infrared, microwaves, radio waves (ULF, VLF, LF, MF, HF, long, short, HAM, VHF, UHF, SHF, EHF), cosmic microwave background radiation and other forms of radiation of the electromagnetic spectrum.

As used herein, a "non-metallic material" is any non-conductive material suitable for depositing a metallic layer thereupon. Examples of "non-metallic materials" include but are not limited to, silicon, silica, glass, alumina, quartz, polymer and graphite. Examples of non-metallic polymers include but are not limited to, polyvinyl chloride (PVC), polyacrylate (PA), polypropylene (PP), polyphenol (PPN), polymethylmethacrylate (PMMA), polycarbonate (PC), polyethylene (PE) and thermoset plastics. In an embodiment, the non-metallic material is a silicon wafer.

As used herein, a "metallic material" can be a metal, metal alloy or mixture thereof. Examples of a metallic material include, but are not limited to, chromium (Cr), molybdenum (Mo), tungsten (W), ruthenium (Ru), copper (Cu), silver (Ag), gold (Au), and conductive polymers. In an embodiment, the metallic material is chromium (Cr).

As used herein, a "catalytic transition metal" can be any transition metal, transition metal alloy or mixture thereof. Examples of a catalytic transition metal include, but are not limited to, nickel (Ni), silver (Ag), gold (Au), platinum (Pt), palladium (Pd), iron (Fe), ruthenium (Ru), osmium (Os), cobalt (Co), rhodium (Rh) and iridium (Ir). In an embodiment, the catalytic transition metal comprises nickel (Ni).

As used herein, a "catalytic transition metal alloy" can be any transition metal alloy. Preferably, a catalytic transition metal alloy is a homogeneous mixture or solid solution of two or more transition metals. Examples of a catalytic transition metal alloy include, but are not limited to, a nickel/gold (Ni/Au) alloy and a cobalt/iron (Co/Fe) alloy.

In an embodiment, a working electrode is a metallic coated non-metallic substrate for use in depositing a catalytic transition metal. In an embodiment the working electrode is a chromium (Cr) coated silicon (Si) wafer. The chromium (Cr) coating provides a flat, conductive and defect free surface on the silicon (Si) wafer. A method of preparing a chromium (Cr) coated silicon (Si) wafer comprises sputtering a layer of chromium (Cr) on a silicon (Si) wafer. In an embodiment the sputtering method is magnetron sputtering.

In an embodiment, a counter electrode is any suitable electrically-conductive metal. In an embodiment, the counter electrode comprises a noble metal. Examples of suitable noble metals include, but are not limited to, gold (Au), platinum (Pt) and iridium (Ir). In an embodiment, the counter electrode is gold (Au) plate.

In an embodiment, an electrolytic solution is a transition metal salt and a mineral acid. Preferably, the transition metal salt is a transition metal sulfate. In an embodiment, the transition metal sulfate is nickel sulfate ($NiSO_4$). Examples of suitable mineral acids include but are not limited to boric acid ($H_3BO_3$), nitric acid ($HNO_3$), hydrochloric acid (HCl) and sulfuric acid ($H_2SO_4$). Preferably the electrolytic solution is weekly acidic. In an embodiment, the mineral acid is boric acid ($H_3BO_3$). For example, the electrolytic solution comprises 0.01 M nickel sulfate ($NiSO_4$) and 0.01 M boric acid ($H_3BO_3$) in double distilled water.

Pulse-Current Electrochemical Deposition (PCED) is an electrochemical deposition process which utilizes a modulated current waveform (a current pulse). PCED can be used to achieve superior leveling of the deposit, and to minimize porosity and contamination. PCED is performed by applying a constant current pulse by using a current source and a voltage source. Both the current source and the voltage source are controlled by any suitable means known in the art including analog and digital controller devices. In an embodiment, the current source and the voltage source is controlled by a computer. In an embodiment, PCED is performed by applying a constant current pulse to a two electrode system comprising a working electrode and a counter electrode. The working electrode and the counter electrode are spaced at a suitable distance. In an embodiment, PCED is carried out on a two electrode system, wherein the distance between the two electrodes is maintained at about 1 cm, and a constant current pulse is applied by using a current source and a voltage source, both of which are controlled by the computer program. The working electrode is prepared by sputtering a layer of chromium on a silicon wafer thereby obtaining a flat, conductive and defect free surface. A gold plate is used as a counter electrode. About 1 $cm^2$ of the working electrode surface is exposed to a weakly acidic electrolyte solution comprising 0.01 M $NiSO_4$ (0.01M $Ni^{2+}$) and 0.01 M $H_3BO_3$ in double distilled water at room temperature. PCED is performed at any suitable temperature. In an embodiment, the PCED is performed at room temperature.

Many factors with PCED can affect the deposited microparticles, including the composition of the electrolyte solution; the surface morphology of the substrate; the magnitude of the applied pulse current density and the duration time. Lowering the concentration of transition metal ions will decrease both the nucleation site density and the size of the deposited catalytic transition metal microparticles.

Varying mineral acid concentrations, such as boric acid concentrations, changes the pH value. Solutions with a support electrolyte (potassium chloride) added are tested and it is found only when the concentration of mineral acid is very low and no other support electrolyte is added, the catalytic transition metal microparticles with low site density and large size (larger than 100 nm in diameter) are achieved. When the mineral acid concentration increases or some other support electrolyte is added, the conductivity of the solution increases, and the electrodeposited catalytic transition metal microparticles have higher density and smaller size. The surface morphology of the substrate also affects the distribution of the deposited catalytic transition metal microparticles. Microparticles form on the defect site of the substrate with high site density. In order to eliminate the aggregation of the microparticles, a sputtering method is used to coat a thin layer of metallic material such as chromium (Cr) on the non-metallic substrate material such as a silicon (Si) wafer to obtain a conductive and defect free surface.

When the solution composition and the substrate are fixed, the site density and the size of the catalytic transition metal microparticles are determined by the combined effect of applied pulse current density and duration time. High current density and long duration time result in high site density and large particles (greater than about 100 nm).

In an embodiment, the size distribution of the electrochemical deposited catalytic transition metal microparticles is quite large. Both large particles (greater than about 100 nm) and small particles (less than about 50 nm) are deposited on the substrate material. The morphology of the CNTs is related to the size of the catalytic transition metal microparticles. When the diameter of the catalytic transition metal microparticles is smaller than about 50 nanometers, either no CNTs or only short and curved CNTs are grown. When the size of the catalytic transition metal microparticles is large, well-aligned CNTs with uniform length distribution are grown. In an embodiment, the substrate material is optionally plasma etched prior to CNT growth to substantially reduce the number of catalytic transition metal microparticles that have a diameter smaller than about 50 nanometers. The plasma etches the catalyst substrate and at the same time assists the CNT growth.

CNTs can be grown by any suitable method known in the art. For example, CNTs can be grown by any chemical vapor deposition (CVD) method, including but not limited to, plasma enhanced chemical vapor deposition (PECVD), hot filament chemical vapor deposition (HFCVD) or synchrotron radiation chemical vapor deposition (SRCVD). In CVD, gaseous mixtures of chemicals are dissociated at high temperature (for example, $CO_2$ into C and $O_2$). This is the "CV" part of CVD. Some of the liberated molecules may then be deposited on a nearby substrate (the "D" in CVD), with the rest pumped away. In an embodiment, CNTs are obtained by placing a catalyst substrate material, which is formed by electrochemical deposition of catalytic transition metal microparticles, with a pre-determined site density, on a metal coated non-metallic substrate material, within a PECVD chamber known in the art, following which CNT growth is initiated on the surface of the catalyst substrate material by standard methods described in the art (see for example Z. F. Ren, et al., Science, 282, 1105 (1998); Z. P. Huang, et al., Appl. Phys. A: Mater. Sci. Process, 74, 387 (2002); and Z. F. Ren et al., Appl. Phys. Lett., 75, 1086 (1999), all of which are incorporated herein by reference in their entirety).

A promoter gas can be a substance that is a gaseous compound at the reaction temperatures, and preferably comprises a non-carbon gas such as ammonia, ammonia-nitrogen, hydrogen, thiophene, or mixtures thereof. The promoter gas may be diluted by mixing it with a diluent gas, which are primarily unreactive, oxygen-free gases, such as for example, hydrogen, helium, nitrogen, argon, neon, krypton, xenon, hydrogen sulfide, or combinations thereof. For the CVD reaction process of the presently disclosed embodiments, hydrogen is preferred for reaction temperatures maintained at less than about 700° C., while for higher temperatures (greater than or equal to about 700° C.), the promoter gas is chosen from ammonia, hydrogen, nitrogen, or any combination thereof. The promoter gas can be introduced into the reaction chamber of the reaction apparatus (e.g. the CVD reaction chamber) at any stage of the reaction process. Preferably, the promoter gas is introduced into the reaction chamber either prior to or simultaneously with the carbon source gas. The CNT nanotube nucleation process on the catalyst substrate is catalyzed by the promoter gas enabling every metal catalyst "cap" that is formed within individual tubules to catalyze their efficient and rapid growth.

A carbon source gas can be saturated, unsaturated linear branched or cyclic hydrocarbons, or mixtures thereof, that are in either the gas or vapor phase at the temperatures at which they are contacted with the catalyst substrate material (reaction temperature). Preferred carbon source gases include methane, propane, acetylene, ethylene, benzene, or mixtures thereof. In an embodiment, the carbon source gas for the synthesis of linear CNTs is acetylene.

CNT tubule diameter, tubule length, number of concentric graphene layers (graphitization) comprising individual tubules and the yield of the CNTs is controlled by varying the reaction temperature of CNT synthetic process.

The manufacturing methods described herein facilitate the tailoring of linear CNT morphology by controlling gas pressure. At low pressures, CNTs with a tubular hollow structure can be obtained, whereas at high pressures, CNTs with "bamboo-like" structure and increased compartmental density can be obtained. The number of graphene layers, which is related to thickness of the tubule wall and diaphragm of the CNTs, can also be controlled during their formation by control of gas pressure. Once the first layer forms as a bamboo-like structure, all subsequent layers terminate on the surface of the CNT.

Scanning electron microscopy (SEM) is employed to examine the morphology. Transmission electron microscopy (TEM) is used to characterize the structure of the CNTs by standard methods.

A dielectric can be any a non-conducting or insulating material. Preferably, the dielectric has a low porosity, a high density and is substantially defect free. Examples of dielectrics include high-density polymers, and metal oxides. In an embodiment, the dielectric is aluminum oxide ($Al_2O_3$), $SiO_2$, MgO, $Si_3N_4$ or $TiO_2$, or a combination thereof.

As used herein, the term "ligand" or "analyte" or "marker" or "target species" refers to any molecule being detected. It is detected through its interaction with an active sensing element, which specifically or non-specifically binds the target species. The target species can be any molecule for which there exists another molecule, such as an active sensing element, which specifically or non-specifically binds to the target species, owing to recognition, chemical or otherwise, of some portion of the target species. The active sensing element, for example, can be an antibody and the target species a molecule such as an antigen which binds specifically to the antibody. In the event that the antigen is bound to the surface and the antibody is the molecule being detected, for the purposes of this document the antibody becomes the target species and the antigen is the active sensing element. The target species may include nucleic acids, proteins, lipids, small molecules, membranes, carbohydrates, polymers, cells, cell membranes, organelles and synthetic analogues thereof.

Target species include, but are not limited to, antibodies (forming an antibody/epitope complex), antigens, nucleic acids (e.g. natural or synthetic DNA, RNA, gDNA, cDNA, mRNA, tRNA, etc.), lectins, sugars (e.g. forming a lectin/sugar complex), glycoproteins, receptors and their cognate target species (e.g. growth factors and their associated receptors, cytokines and their associated receptors, signaling receptors, etc.), small molecules such as drug candidates (either from natural products or synthetic analogues developed and stored in combinatorial libraries), metabolites, drugs of abuse and their metabolic by-products, co-factors such as vitamins and other naturally occurring and synthetic compounds, oxygen and other gases found in physiologic fluids, cells, cellular constituents cell membranes and associated structures, natural or synthetic toxins, pathogens (e.g., *Bacillus anthracis, Yersinia pestis, Francisella tularensis, Coxiella burnetii*) other natural products found in plant and animal sources, other partially or completely synthetic products, pathogens (e.g. virus and bacteria, etc.), and the like. Target species may be found in a variety of heterogeneous test samples (e.g., water, saliva, sweat, urine, serum, blood, plasma, tissues and food).

The active sensing element is adapted to selectively capture at least one target species. For example, the active sensing element can specifically or nonspecifically bind with another molecule (such as a target species). Also, the active sensing element can exert specific enzymatic activity with the target species to produce intermediate molecules that can change the physiochemical environment in the nanocavity. As used herein, the active sensing element is usually immobilized on the surface of a nanoscale sensor, either alone or as a member of a binding pair that is immobilized on the surface. In some embodiments, the active sensing element may include the molecules on the signal path, on a dielectric surface or in a dielectric volume, or a conductive surface, such as on the inner or outer conductor of the coaxial nanosensor. Immobilization of the active sensing element can be performed by one or more linkers.

The selective capture of the target species can be a specific binding, such as by a binding reaction which is determinative of the cognate target species of interest in a heterogeneous population of proteins and/or other biologics. Thus, under designated conditions, the specified target species binds to its particular active sensing element (e.g., a hormone specifically binds to its receptor, or a given nucleic acid sequence binds to its complementary sequence) and does not bind in a significant amount to other molecules present in the sample or to other molecules to which the target species or antibody may come in contact in an organism or in a sample derived from an organism.

A. Nanoscale Sensors

FIG. 1A shows a schematic view of a nanoscale sensor unit structure 100. The nanoscale sensor unit structure 100 comprises a dielectric material 180 located between a first electrical conductor 120 and a second electrical conductor 160. In some embodiments, the dielectric material 180 includes a nanoporous material, as described in greater detail below. In general, the use of a nanoporous material may improve the sensor performance in detecting an analyte, e.g., by attracting and or binding the analyte (e.g., through adsorption).

The first electrical conductor 120 serves as an internal electrode and the second electrical conductor 160 serves as an outer electrode. The nanoscale sensor unit structure 100 is supported by a metallized substrate 190, such as an insulating or semiconducting substrate that is partially or entirely coated with a metal layer. Other substrates, including substrates without a metal layer, may be used. The standing nanoscale sensor unit structure 100 is supported by a thick dielectric material 140. A nanocavity 130 is fabricated at the upper end of the nanoscale sensor unit structure 100 after chemical etching of at least a portion of the dielectric material 180. In an embodiment, the dielectric material 180 is entirely removed by etching. Alternatively, a portion of the dielectric material 180 is removed by etching. In an embodiment, the dielectric material is $Al_2O_3$ and is etched with NaOH. Active sensing elements 150 can be immobilized within the nanocavity 130, for example on the first electrical conductor 120 for selective capture of the target species. The nanocavity area houses a solution containing the target species. In an embodiment, the solution may be aqueous based, such as pure water, water with biomolecules, physiological saline or other solutions known in the art. In an embodiment, the solution may be in organic solvents, such as acetic acid, acetone, benzene, carbon tetrachloride, chloroform, dichloromethane, dimethylformalmide (DMF), dimethylsulphonate (DMSO), ethanol, ether, ethyl acetate, light petroleum, methylated spirits (~2% methanol in ethanol), methanol, petroleum spirit, pyridine, mineral oil, or other solvents known to those skilled in the art.

The internal electrode 120 may be a nanostructure having a conductive core. Examples of materials that can be used for the internal electrode 120 include but are not limited to, carbon fiber; carbon nanotube; pure transition metals such as nickel (Ni), aluminum (Al), or chromium (Cr); metal alloys, e.g. stainless steel (Fe/C/Cr/Ni) or aluminum alloys (Al/Mn/Zn); and metallic polymers. Other internal electrodes 120 are highly doped semiconductors, and semi-metals (metals with vanishingly small band gap, e.g. graphite). In an embodiment, the internal electrode 120 is a carbon nanofiber, such as carbon nanotube, for example a SWCNT or MWCNT. The nanotubes may, but need not, be substantially of the metallic chirality. The nanotubes can include a mixture of metallic and semiconducting chiralities. The nanotubes are preferably sufficiently conductive to be used as the inner conductor of a nanocoaxial capacitor. Those skilled in the art will recognize that the internal electrode 120 may be other conducting materials known in the art and be within the spirit and scope of the present embodiments.

The internal electrode 120 may be non-conducting nanostructure coated with a conducting (e.g., metallic) material. For example, the inner electrode may include a polymer (e.g., SU-8) nanopillar coated with a metallic material (e.g., Al, Cr, etc.). Arrays of such polymer nanopillars may be fabricated using nano-imprint lithography (NIL) techniques, e.g. using an array of silicon nanopillars as an NIL master.

Although the inner electrode 180 is shown having a cylindrical shape, any other suitable shape may be used, including a conical, trapezoidal, tapered, or other shape. In some embodiments the shape may be truncated.

The dielectric material 180 circumferentially surrounds a portion of the internal electrode 120, either uniformly surrounding the internal electrode 120 or non-uniformly surrounding the internal electrode 120. In an embodiment, the dielectric material 180 may be $Al_2O_3$, $SiO_2$, MgO, $Si_3N_4TiO_2$, or a non-conductive polymer, or a combination thereof, and may be deposited by sputter coating, atomic layer deposition, or electropolymerization. The dielectric material 180 can be crystalline (periodic arrangement of atoms in macroscopic scale), polycrystalline (periodic arrangement of atoms in microscopic scale), or amorphous (aperiodic arrangement of atoms in macroscopic scale). Optionally, the dielectric material 180 can be omitted.

The second electrical conductor or outer electrode 160 may be a metal nanostructure. Thus, the outer electrode 160 may take the form of a metallic cylinder. In an embodiment, the metallic cylinder provides shielding of electromagnetic waves that are transmitted along the length of the unit structure 100. Examples of outer electrodes include but are not limited to, pure transition metals such as nickel (Ni), aluminum (Al), chromium (Cr), titanium (Ti), gold (Au), platinum (Pt); metal alloys e.g. stainless steel (Fe/C/Cr/Ni) or aluminum alloys (Al/Mn/Zn); a conductive metal oxide; and metallic polymers. In an embodiment the outer electrode 160 is chromium. Those skilled in the art will recognize that the outer electrode 160 may be other conducting materials known in the art and be within the spirit and scope of the presently disclosed embodiments.

The nanoscale sensor unit structure 100 can be simplified as a nanoscale coaxial capacitor, whose capacitance is proportional to the dielectric constant of the materials filling in the gap between the internal electrode 120 and the outer electrode 160. Any method that is based on capacitance measurement is applicable to form a biosensing system with the proposed nanoscale sensor unit structure 100. The dimension of the nanoscale sensor unit structure 100 is in the nano or sub-micro range, therefore most of the target species can produce signals upon the specific binding to their active sensing elements 150 immobilized on the internal electrodes 120. Preferably, the volume of the nanocavity 130 is sufficiently small to allow magnification of the signal transduction. The signal-to-noise ratio is improved due to electromagnetic shielding between the first and second conductors 120, 160. For example, even a single molecule can be detected.

Figure 1B:
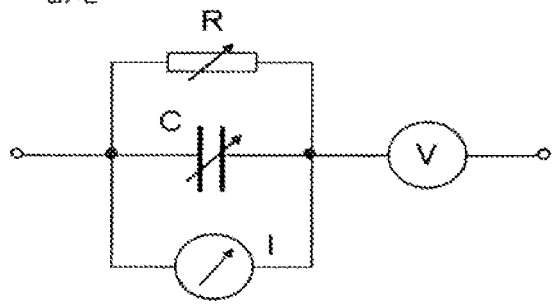
FIG. 1B shows an equivalent circuit diagram of the nanoscale sensor unit structure of FIG. 1A.

An example of an equivalent circuit of the nanoscale sensor unit structure 100 is illustrated in FIG. 1B. A method for detecting the presence of target species is any measurement method that measures the real and/or imaginary component(s) of capacitance, such as Impedance Spectroscopy (IS) and Time Domain Dielectric Spectroscopy (TDDS), by scanning over the frequency range of about 1 Hz to about 10 GHz, such as about 1 Hz to about 10 MHz or about 1 MHz to about 10 GHz, to measure the impedance and/or dielectric constant between the two conductors. For example, the presence of a target species between the two conductors induces a change in the capacitance, as manifested by a change in impedance and/or dielectric constant being measured. The present embodiments makes use of the observation that a vast number of molecules can be distinguished based upon the unique dielectric properties most molecules exhibit. These distinguishing dielectric properties can be observed by coupling an electromagnetic signal to the captured target species. The unique dielectric properties change the signal, giving it a unique signal response. The unique signal response can then be used to detect and identify the target species and other molecules which make up the molecular binding region. C, the capacitance of the nanoscale sensor unit structure 100, is variable to the change in $\in_r$ corresponding to any target species binding on the internal electrode 120. The capacitance is also sensitive to the interference of electrode-solution interface by the molecular interactions. R, the resistance between the inner electrode 120 and the outer electrode 160, is sensitive to $\rho$ which is determined by the composition of the dielectric material 180. An electron transfer resistance exists due to electron transfer at the electrode-solution interface. If a redox couple is in the solution containing the target species, a diffusion impedance should be taken into account. These parameters are all subject to change upon the molecular bindings. V and I are electric biases (i.e., voltage and current) introduced by reactive species due to their redox properties.

IS measures the dielectric properties of a medium as a function of frequency. IS is based on the interaction of an external field with the electric dipole moment of the sample, often expressed by permittivity. This is an established method that is sensitive to polarization interfaces and intermolecular interactions, such as dipole-dipole interactions and cooperative processes, and has been used for extracting with high accuracy the electrical dipole moment for biomolecules, such as myoglobin, hemoglobin, DNA, etc. Traditionally, the recording is done with a standard time domain reflectometer. But problems associated with such a setup are the high level of drift and instabilities during generation of the signal and its detection in the sampler are usually inherent in the serial reflectometry equipment, since the registration of incident $V_o(t)$ and reflected $R(t)$ signals is accomplished by the accumulation of several measurements. The nanoscale sensor unit structure 100 enhances the signal-to-noise ratio without such troublesome accumulation. The system performance can be further enhanced by using digital sampling oscilloscopes and automated, high-precision TDDS hardware.

Figures 2A, 2B, 2C:
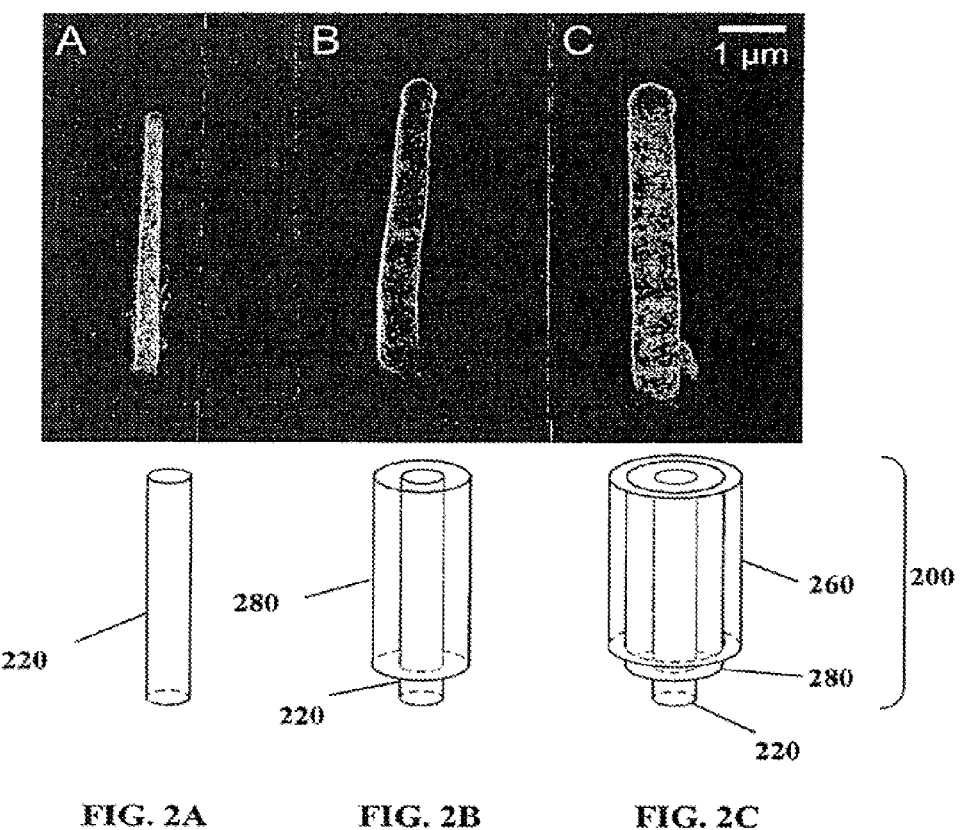
FIG. 2A-2C show schematic and exemplary views of a nanoscale coaxial transmission line built around a carbon nanotube.

FIG. 2A-2C each show a schematic view (bottom) and an exemplary view (top) of a nanoscale coaxial transmission line 200 built around a carbon nanotube 220. The schematic views show the major steps for fabricating a nanoscale coaxial transmission line 200. The exemplary views were taken using a scanning electron microscope (SEM) at a 30 degree angle relative to the sample surface.

FIG. 2A shows a schematic view and an exemplary view of a carbon nanotube as the internal electrode 220. The plasma-enhanced chemical vapor deposition (PECVD) method is used to grow vertically-aligned, multiwalled, straight carbon nanotubes with an average length of about 5-6 μm using a nickel catalyst (FIG. 2A). The catalyst is electrodeposited on a thin chromium layer (about 10 nm) sputtered on the top of a substrate.

FIG. 2B shows a schematic view and an exemplary view of a carbon nanotube 220 after coating with a dielectric material 280. The nanotube 220 was coated with a dielectric material 280 of aluminum oxide ($Al_2O_3$). The dielectric material 280 has a thickness between about 100 nm to about 150 nm or thicker.

FIG. 2C shows a schematic view and an exemplary view of a carbon nanotube 220 after being coated with a dielectric material 280 and an outer conductive material 260. The nanotube 220 coated with the dielectric material 280 was sputtered with about 100 nm to about 150 nm thick chromium layer as the outer conductor 260. In an embodiment, the outer conductor 260 is thicker than about 150 nm.

Figures 3A, 3B:
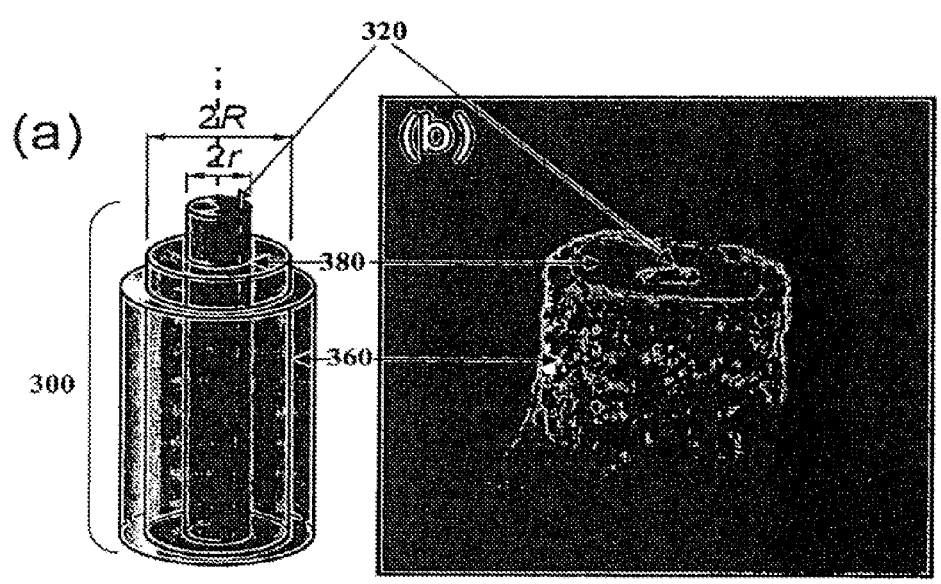
FIG. 3A shows a schematic view of a nanoscale coaxial transmission line built around a carbon nanotube.
FIG. 3B shows a scanning electron microscope (SEM) image of the nanoscale coaxial transmission line built around a carbon nanotube. The carbon nanotube's diameter is about 100 nm.

FIGS. 3A-3B show a nanoscale coaxial transmission line according to an embodiment of the present invention. The nanoscale coaxial transmission lines can propagate light over large distances (>>wavelength λ) through nanostructures with nanoscopically restricted, subwavelength transverse dimensions (<<λ). A schematic of a nanoscale coaxial transmission line 300 is illustrated in FIG. 3A. The nanoscale coaxial transmission line 300 (with a center located at the dashed line) includes a metallic nanostructure wire 320 of radius r, a dielectric filling material with radius R, and a coaxial metallic cylinder 360 with inner radius R. A dielectric medium 380 fills the gap in between the wire 320 and the cylinder 360. The physics of the conventional coaxial cable is well-established: (i) the basic transmitted mode is transverse electromagnetic (TEM), (ii) for this mode, the wave impedance of the coaxial cable is identical to that of free space filled with the same dielectric medium as in the coaxial cable (iii) this mode operates at arbitrary frequency (i.e. no cut-off), and (iv) attenuation is dominated by resistive losses in the metal.

In conventional coaxial cable theory, the assumption is that the electrode metals are nearly perfect, i.e. highly conductive, and the dielectric medium between electrodes is of very low loss. Impedance matching of a coaxial cable to free space can be achieved very efficiently by extending the center conductor beyond the coax end, so that it forms an antenna. The nanoscale coaxial transmission line 300 retains approximately all of the above properties of the conventional coaxial cables.

In the visible frequency range, conventional coaxial cable theory must be modified because of plasma effects. Typically, metals have their plasmon resonances (bulk and surface) in the visible or UV frequency ranges. Interaction of the plasmon resonances with transmission line modes (photon modes) leads to new modes, so-called plasmon polaritons. Each metal-dielectric interface in a nanoscale coaxial transmission line of the presently disclosed embodiments supports a plasmon polariton. Consider a single, planar interface between a metal with dielectric function $\in_1$ and a uniform dielectric with dielectric constant $\in_2$. Solving this problem involves matching plane wave solutions of Maxwell's equations in each region across the interface, using standard boundary conditions. To describe the metallic region, the Drude dielectric function $\in_1 = \in_b - \omega_p^2/(\omega^2 + i\omega\gamma)$, can be used, where $\omega$ is the frequency, $\omega_p$ is the metal's plasma frequency, $\gamma$ is the damping parameter, and $\in_b$ is the contribution from bound electrons in the metal.

Figure 4:
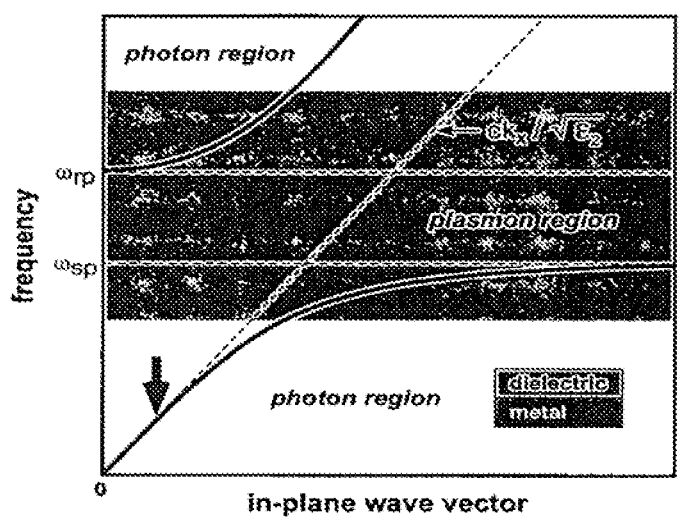
FIG. 4 shows the plasmon polariton dispersion (k) at the metal-dielectric interface of a nanoscale coaxial transmission line according to an embodiment of the present invention.

FIG. 4 shows a plot of frequency as a function of in-plane wave vector. The resulting eigenmode of the system, the plasmon polariton, has the dispersion (for $\gamma \to 0$). The topology and meaning of this dispersion relation is clear: the "light line" ($\omega = ck_x/\sqrt{\in_2}$) crosses the surface ($\omega_{sp} = \omega_p/\sqrt{\in_2 + \in_b}$) and bulk ($\omega_{rp} = \omega_p/\sqrt{\in_b}$) plasmon resonances, and this anti-crossing results in the two-branch structure of the plasmon polariton. For small values of $k_x$, the lower branch asymptotically approaches the light line (arrow in FIG. 4), so that the plasmon polariton becomes identical to the free-space TEM photon mode. In the higher, plasma frequency range, on the other hand, there is a drastic departure from the simple free-space plane wave behavior: a gap opens in the spectrum, and the plasmon polariton acquires "mass" at the renormalized bulk plasmon frequency ($\partial^2\omega/\partial k_x^2 \neq 0$).

Elements of this mode structure prevail in the nanoscale coaxial transmission line 300. The main conclusions regarding the low-frequency solution ($\omega \ll \omega_p$), however, are essentially the same as above, as long as (a) $d = R - r \geq \delta_0$, where $\delta_0 = \sqrt{2/\omega\sigma\mu_0}$ is the penetration depth into the metal, $\sigma$ is the dc-conductivity of the metal, and (b) $2r > d_c = c/\omega_p$. Then, the plasmon polariton in the nanoscale coaxial transmission lines of the presently disclosed embodiments has dispersion given by $$k_x = (\omega/c)\sqrt{\varepsilon_2} - i\alpha \quad (1)$$

where $$\alpha = F(\omega, \gamma) \frac{\sqrt{\varepsilon_2}}{\ln(R/r)} \left(\frac{1}{r} + \frac{1}{R}\right) \ll \operatorname{Re}(k_x) \quad (2)$$

This shows that the transmitted mode is again essentially free-space TEM (because of the linear dispersion and the fact that $k_z = \sqrt{(\omega/c)^2 \in_2 - k_x^2} \approx 0$) and it is propagating along the coaxial transmission line 300 in the x direction, outside the inner nanostructure conductor 320 (the wave vector depends only on $\in_2$). The exponential decay along the propagation direction (due to losses in the metal) is parameterized by $\alpha$, or alternatively by the photon propagation length $L = 1/\alpha$. In the extreme low frequency limit, $\omega \ll \gamma \ll \omega_p$, $F(\omega,\gamma) \approx \sqrt{\omega\gamma}/2$ $\sqrt{2}\omega_p = (2\sigma\delta_0)^{-1}$ and Equation (2) reduces to the well-know decay constant of a conventional coaxial cable mode. In the intermediate frequency range, $\gamma \ll \omega \ll \omega_p$, the difference is that the mode experiences much slower decay described by Equation (2), with $F(\omega,\gamma) \approx \gamma/4\omega_p$.

The nanoscale coaxial transmission line 300 shown in FIGS. 3A and 3B are based on a multi-walled carbon nanotube used as the inner nanostructure conductor 320. Carbon nanotubes are substantially conductive, with plasma frequency ($\omega_p$) at about 6 eV, and losses in the visible range comparable to those in Cu, i.e. $\approx 0.003\omega_p$. For the carbon nanotubes 320 shown in FIGS. 3A and 3B, r is about 50 nm, and thus $2r > d_c = c/\omega_p \approx 50$ nm. The diameter of the inner conductor 320 can range from about 40 nm to about 200 nm, such as about 80 nm to about 150 nm. For the nanoscale coaxial transmission line 300 shown in FIGS. 3A and 3B, aluminum oxide ($Al_2O_3$, $\in_2 = 2.62$ in the visible range) may be used as the transparent dielectric material 380. The thickness (d) of the dielectric 380 is about 100 nm, which assures that the nanoscale coaxial transmission line 300 shown in FIGS. 3A and 3B is a subwavelength transmission line, and also that $d = 100$ nm $\gg \delta_0 \sim 10$ nm. The thickness of the dielectric 380 can range from about 10 nm to about 500 nm, such as about 50 nm to about 300 nm. In an embodiment, Cr is chosen as the material for the outer electrode 360 of the nanoscale coaxial transmission line 300, whose dielectric constant in the visible range is $\in_{Cr} = -3 + i18$, thus well-simulating, in the visible, the low-frequency dielectric response of a good metal. The nanoscale coaxial transmission line 300 propagates a weakly dispersive mode, resembling in all respects the conventional TEM coaxial cable mode in the visible frequency range. The propagation length (L) of visible light along the nanoscale coaxial transmission line 300 is about 50 μm in the visible range (i.e. about $10^2$ wavelengths), which is a suitable propagation distance for many nanoscale applications.

FIG. 5 shows an apparatus 500 that is capable of transmitting visible light through nanoscale coaxial transmission lines 510 that are many wavelengths in length, with an inter-electrode separation much less than a wavelength, for example about 500 nm or less, such as about 300 nm or less. The apparatus 500 comprises the array of nanoscale coaxial transmission lines 510 distributed uniformly or periodically on a metallized substrate 590. The array of nanoscale coaxial transmission lines 510 may be aligned in rows or unevenly distributed on the metallized substrate 590. The array may be arranged in an ordered pattern on the metallized substrate 590, such as in a hexagonal pattern. The metallized substrate 590 may be transparent. The metallized substrate 590 may be composed of a polymer, glass, ceramic material, carbon fiber, glass fiber or combinations thereof onto which a layer of metallic material is deposited. The metallized substrate 590 includes a metal layer that covers a portion or all of the substrate. Optionally, the metal layer is absent and the metallized substrate 590 is not metallized. Those skilled in the art will recognize that the substrate may be other materials known in the art and be within the spirit and scope of the presently disclosed embodiments.

An array of vertically aligned conductors 520 (e.g., multi-walled carbon nanotubes or other types of nanowires or nanofibers) are grown or attached to the substrate 590. Next, the conductors 520 are coated with appropriate dielectric material 580. The conductors 520 are then coated with a metallic layer 560 acting as the outer conductor.

The apparatus 500 includes vertically aligned carbon nanotubes 520 grown on a glass substrate coated with a thin (about 10 nm) chromium layer. On this layer, nickel catalyst for PECVD growth of nanotubes was deposited electrochemically. Then, nanotubes 520 were coated with about 150 nm of aluminum oxide as the dielectric material 580 and then with about 100 nm of chromium as the metallic layer 560. The entire array of nanoscale sensor unit structures was filled with spin-on-glass (SOG) which does not affect array functionality but allowed the top part of the nanoscale coaxial transmission lines 510 to be mechanically polished off. In an embodiment, the thickness of the SOG is about 6 µm, preferably less than about 50 µm, such as less than 20 µm. Optionally, a nanocavity is etched into the dielectric material 580 and an active sensing element is immobilized within the nanocavity on the inner conductor 520 or the outer conductor 560, or both.

Figure 5A:
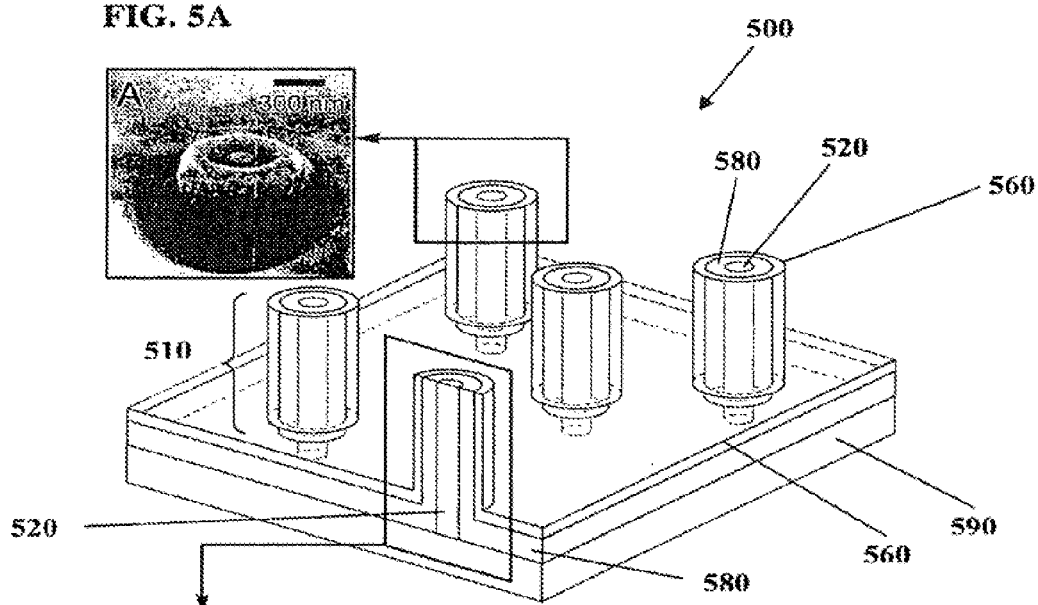
FIG. 5A shows a single nanoscale coaxial transmission line viewed by SEM.
Figures 5B, 5C:
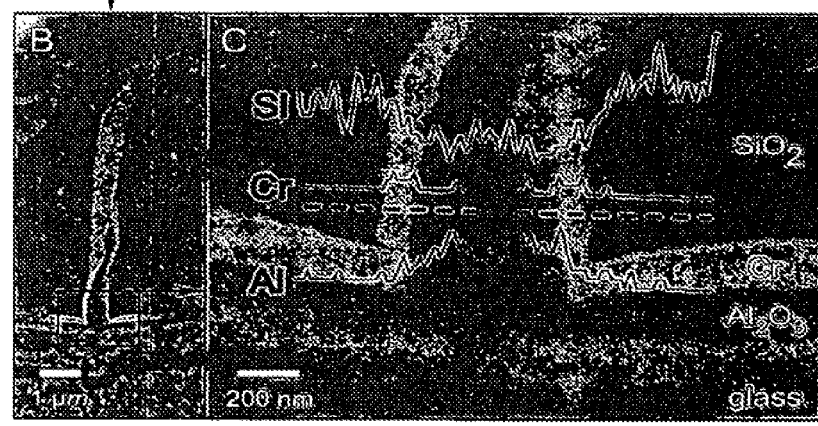
FIG. 5B shows a cross-section view of a single nanoscale coaxial transmission line viewed by a scanning electron microscope.
FIG. 5C shows an energy dispersive x-ray spectroscopy (EDS) analysis of the composition of the coaxial layers showing concentration mapping for silicon (Si), chromium (Cr), and aluminum (Al).

FIG. 5B shows a cross-section view of a single nanoscale coaxial transmission line 510 viewed by a scanning electron microscope showing the internal structure of the nanoscale coaxial transmission line 510.

FIG. 5C shows an energy dispersive x-ray spectroscopy (EDS) analysis of the composition of the coaxial layers of each of the nanoscale coaxial transmission lines 510 showing concentration mapping for spin-on-glass (SOG), chromium (Cr), and aluminum (Al). The dotted line in FIG. 5C corresponds to the position of the EDS linescan while three presented plots correspond to spin-on-glass (SOG), chromium (Cr), and aluminum (Al) concentration along the scanned line. FIG. 5C shows that the concentration of silicon is highest in the spin-on-glass (SOG) rich area. Similarly, the highest chromium concentration is present in the region of outer metallic coating of walls, and highest aluminum concentration is observed in the area of dielectric material 580 ($Al_2O_3$).

Due to the presence of the non-transparent Cr coating 560, light may pass through the sample only via the interior of the nanoscale coaxial transmission lines 510, i.e. through the inter-electrode spacing (d=R-r~100 nm) filled with alumina. In the embodiment shown in FIG. 5, the inner electrodes 520 of each nanoscale coaxial transmission line protrudes about 250 nm on the substrate side, and thus serve as nanoantennas providing efficient coupling to external radiation. On the polished side, however, there is no antenna section, and thus, the overall transmission through a nanoscale coaxial transmission line 510 is "bottlenecked" by this antenna-less end, and is expected to be very small.

Figure 5D:
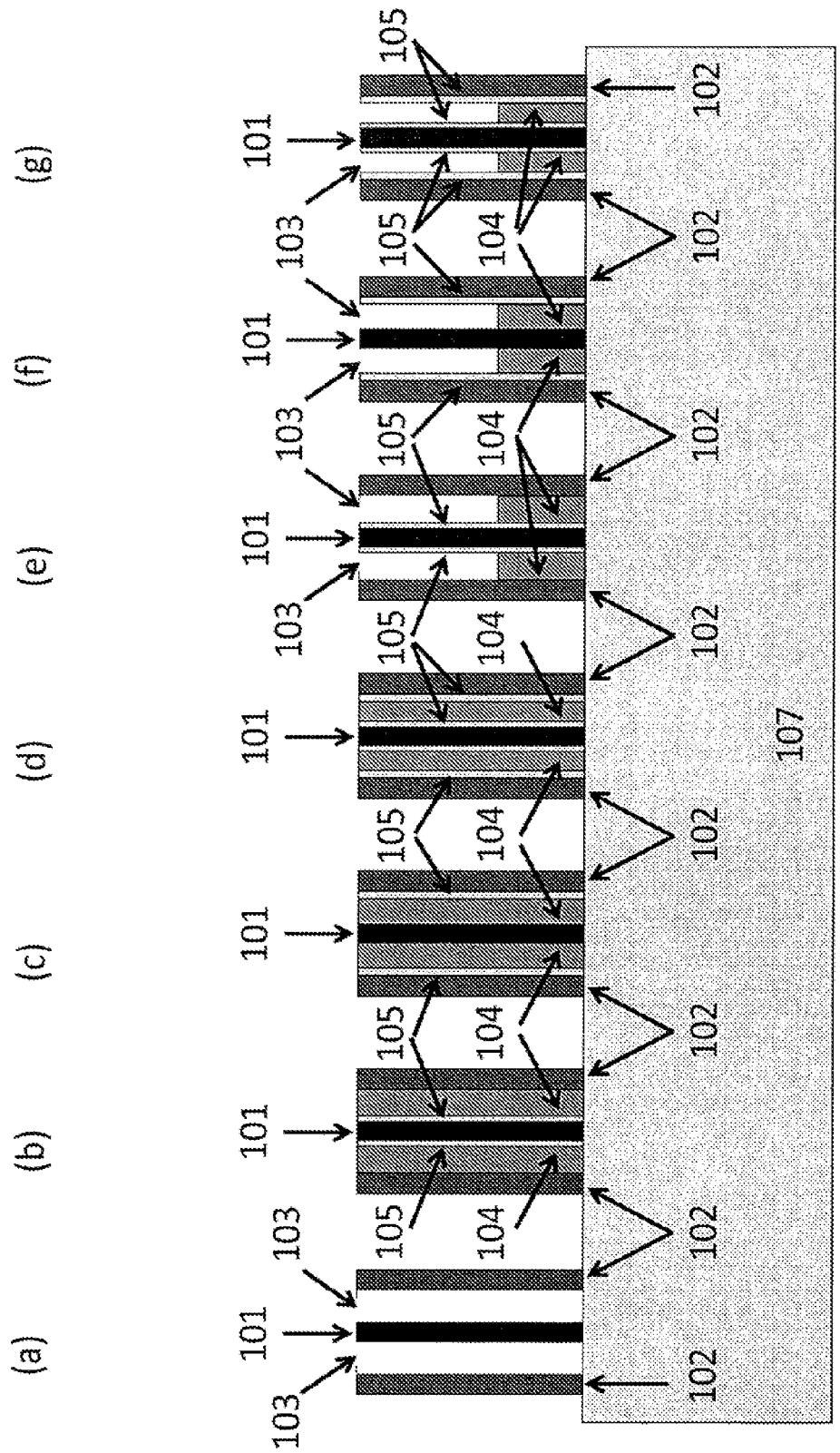
FIG. 5D shows embodiments of a nanoporous nanosensor.

Referring, now to FIG. 5D, some embodiments (a)-(g) of nanocoaxial dielectric impedance chemical sensors are illustrated. FIG. 5D (a) illustrates a nanocoaxial dielectric impedance sensor comprising a hollow annulus. FIG. 5D (b)-(d) illustrate nanocoaxial dielectric impedance sensors having an annulus filled with various arrangements of porous and nonporous dielectric/electrically-insulating material layers, as detailed below. FIG. 5D (e)-(g) illustrate nanocoaxial dielectric impedance sensors having an annulus filled with various arrangements of porous and nonporous material with partial filling with the porous material, such that a nanocavity is formed in the top end of the sensor.

Each nanosensor of FIG. 5D includes a coax outer conductor 102 comprising a conductive (e.g., metallic) material on a substrate 107. Each nanosensor further comprises an inner conductor 101 that may include a metal nanowire or a metalized nanopillar. The nanosensor (a) includes a hollow coax annulus 103, comprising no porous material deposited inside the annulus (or after such material is removed after deposition).

The nanosensor (b) includes a layer of nonporous coating 105 on the inner conductor 101 and a nanoporous material 104 filling the remainder of the space between the inner conductor 101 and the outer conductor 102. In some embodiments, the nonporous coating 105 on the inner conductor 101 is formed prior to the formation of the nanoporous material 104, thereby preventing the unwanted filling of the pores of the nanoporous material 104.

The nanosensor (c) includes a layer of nonporous coating 105 on the outer conductor 102 and a nanoporous coax material 104 filling the remainder of the space between the inner conductor 101 and the outer conductor 102. In some embodiments, the nonporous coating 105 on the outer conductor 102 is formed prior to the formation of the nanoporous material 104, thereby preventing the unwanted filling of the pores of the nanoporous material 104.

The nanosensor (d) includes both a layer of nonporous coating 105 on the inner conductor 101 and a layer of non-porous coating 105 on the outer conductor 102. A nanoporous coax material 104 fills the remainder of the space between the inner conductor 101 and the outer conductor 102. In some embodiments, the nonporous coating 105 on the inner and/or the outer conductor 102 is formed prior to the formation of the nanoporous material 104, thereby preventing the unwanted filling of the pores of the nanoporous material 104.

The nanosensors (e), (f), and (g) have similar layer structures to nanosensors (b), (c), and (d), respectively. However, the space between the inner conductor 101 and the outer conductor 102 is only partially filled with the porous material 104 such that a nanocavity 103 is formed in the top end of the sensor. Again, in some embodiments, the nonporous coating 105 on the inner and/or the outer conductor 102 is formed prior to the formation of the nanoporous material 104, thereby preventing the unwanted filling of the pores of the nanoporous material 104. In some alternative embodiments, the nanoporous material 104 may be replaced with a nonporous material partially filling the space between the conductors 101 and 102.

While in some embodiments, a nanosensor may include a hollow annulus 103 (as shown in FIG. 5D (a)), the annulus may also be modified to be either fully filled, or partially filled by any amount between 0% and 100% of the total annulus volume. The nanoporous material 104, may include pores having diameters of anywhere between 1 and 100 nm, such as for example between 1 and 10 nm, 10 and 20 nm, 20 and 30 nm. The nonporous coating 105 between the nanoporous material 104 and the inner conductor 101 and/or the outer conductor 102 may comprise any nonporous material capable of separating the nanoporous material 104 from the conductor and therefore preventing any short circuits or any undesired electromagnetic effects in the nanocavity.

Nanosensors comprising nanoporous materials 104 may enable the target molecules to enter the annulus and further enter into the nanopores of the material and adsorb or bind onto the surfaces or walls of the nanopores inside the material. The adsorbed molecules may cause a change in effective dielectric constant of the coaxial capacitor, thus inducing an even greater change in capacitance and complex impedances due to its increased surface area introduced by the pores. Since the pores cause the surfaces of the nanoporous materials to have larger, e.g., significantly larger (e.g., larger by a factor of a few, a factor of 10, a factor of 100 or greater) surface areas, these nanostructures enable the molecules to adsorb not only on the visible surfaces, but also inside the pores of the material as well. As the molecules gain access to additional surface areas created by the uneven, hollow and porous surfaces of the nanoporous materials, the nanoporous nanosensor may have an increased physisorption as well as the increased chemisorption. Thus these nanostructures may have an increased probability of binding to the target molecules, increasing the total signal of the binding molecules detected as well as increasing the number of target molecules that can be detected, thus increasing the signal-to-noise ratio.

Nonporous coating 105 may comprise any nonporous dielectric or at least partially insulating material (e.g., a non-metallic material) that may separate or segregate the nanoporous material 104 from the inner conductor 101 and/or the outer conductor 102. Nonporous coating 105 may comprise a material capable of being deposited without pores, forming a uniform, even, solid and smooth surface. Nonporous coating 105 may comprise any one, or a combination of: $Al_2O_3$, $SiO_2$, $TiO_2$, CuO, VPO, $WO_3$, zeolites, methylsilsesquioxane, silica and other aerogels, various nitrides, various polymers, such as PMMA, polyurethane, as well as metal-organic framework materials, such as MOF-177. The nonporous material 105 may be deposited via any deposition means, including thin film deposition methods of any kind, such as the atomic layer deposition (ALD), chemical vapor deposition (CVD), sputtering, physical vapor deposition (PVD), thermal evaporation, electroplating, electropolymerization electroless plating or polymerization, or any other deposition method used in the field. Nonporous coating 105 may be deposited to be any thickness, such as between 1 and 5 nm, 5 and 10 nm, 10 and 30 nm, 30 and 50 nm, 50 and 100 nm or any other thickness between 1 nm and 1 micrometer. The nonporous material may be an insulator material or a semiconductive material. The nonporous material may include any material with resistive, conductive, chemical or physical properties that may be used to bias the operation of the nanosensors. In some embodiments (e.g., FIG. 5D (a)), the nonporous coating 105 may be omitted, such that the nanoporous material 104 directly abuts the inner conductor 101 and/or outer conductor 102.

The nanoporous material 104, herein also referred to as nanoporous coax material 104, may comprise any type and form of nonmetallic material comprising hollow portions, openings or pores. Nanoporous material 104 may comprise any nonmetallic material capable of being deposited to create pores, such as $Al_2O_3$, $SiO_2$, $TiO_2$, CuO, VPO, $WO_3$, zeolites, methylsilsesquioxane, silica and other aerogels, various nitrides, various polymers, PMMA, polyurethane, and metal-organic framework materials, such as MOF-177. The nanoporous material 104 may be deposited via any deposition technique where the deposition process can be controlled to ensure the formation of pores, including thin film deposition of any kind, such as the atomic layer deposition (ALD), chemical vapor deposition (CVD), sputtering, physical vapor deposition (PVD), thermal evaporation or any other deposition method used in the field. In some embodiments, a nonporous material may be deposited initially, and then processed to form the pores, e.g., using electron beam processing techniques, reactive ion processing techniques, etc. Exemplary techniques for forming nanoporous material are described in Samir Iqbal and Rashid Bashir, *Nanopores: Sensing and Fundamental Biological Interactions* Springer (2011).

Note that in some embodiments, nonporous material 105 and nanoporous material 104 may have the same chemical properties, but differing porosity. For example, the nonporous material 105 may be a coating $Al_2O_3$ was deposited by atomic layer deposition (ALD) using deposition conditions that avoid the formation of pores. The nanoporous material may be a porous layer of $Al_2O_3$ formed using a technique such as reactive sputtering with deposition conditions chosen to ensure the formation of pores.

In some embodiments, the layer may be formed using electropolymerization techniques, e.g., of the type described in International Patent Publication No, WO 2010/144157, published Dec. 16, 2010 and incorporated herein by reference. For example, in some embodiments, using the techniques described in this publication, a non-conductive nanocoating (e.g. a polymer nanocoating) is established on a nanostructure, e.g., the inner conductor 101. A target molecule (e.g., a protein) can be incorporated with the coating and then washed out to create imprinted cavities in the coating corresponding to the target molecule. The imprints hold an intrinsic affinity to the target molecule that enables specific recognition. The target-polymer interaction can be measured using the techniques described herein, e.g., as an impedance change. Using the imprinting method, one may be able to selectively detect a target molecule of interest without the use of antibodies or epitopes of antibodies.

Nanoporous material 104 may have any shape or porosity. Nanoporous material 104 may have any porosity or void fraction between 0.1% and 99.9%. Nanoporous material 104 may have porosity of anywhere between 0.1% and 10%, 10% and 20%, 20% and 30%, 30% and 40%, 40% and 50%, 50% and 60%, 60% and 70%, 70% and 80%, 80% and 90% and 90% and 99.9%. In some embodiments, nanoporous material 104 may be filled as a layer as illustrated by the middle and right embodiments of FIG. 5D. However, in other embodiments, nanoporous material 104 may be deposited unevenly, varying in thickness between the top and bottom of the annulus.

As used herein, nanoporous refers to material having a pore size (defined by the largest dimension of the pore) of less than 1 μm. In some embodiments, the nanoporous material may have a maximum pore size (defined by the largest dimension of the pore) of less than 1 μm, less than 500 nm, less than 400 nm, less than 300 nm, less than 200 nm, less than 100 nm, less than 50 nm, less than 10 nm, less than 5 nm, less than 2 nm, less than 1 nm, or less. In some embodiments the nanoporous material may replaced by a porous material having a maximum pore size of 1 μm or more.

Nanoporous material 104 may have any variation of pore sizes, such as pores of between 1 nm to 10 nm in diameter, 10 nm and 20 nm in diameter, 20 nm and 30 nm in diameter, 30 nm and 40 nm in diameter, 40 nm and 50 nm in diameter, 50 nm and 60 nm in diameter, 60 nm and 70 nm in diameter, 70 nm and 80 nm in diameter, 80 nm and 90 nm in diameter, 90 nm and 100 nm in diameter and 100 nm and 10 micrometers in diameter. The sizes of pores and/or porosity may be carefully tuned within a particular range for a specific detection of a specific molecule or they may be random and widely distributed.

For example, when detecting a biological target, such as a protein, DNA, RNA, etc., larger pore sizes (e.g., in the range of 2-500 nm, 10-500 nm, 100-500 nm, etc.) may be used. For detecting chemicals such as an inorganic chemicals a volatile organic chemicals, etc., smaller pore sizes may be used (e.g., in the range of 2-100 nm, 2-50 nm, 2-10 nm, etc.) may be used. Exemplary ranges for pore size and porosity for detecting are show in Table I below.

TABLE I

|  | biological detection | chemical detection |
| --- | --- | --- |
| Pore size range (nm) | 2-500 | 2-100 |
| Porosity range (%) | 1-95 | 1-95 |

The coax outer conductor 102 may have any form, shape and size. In some embodiments, coax outer conductors 102 are cone-shaped, such that they are further apart in the bottom and closer to each other on the top. In other embodiments, coax outer conductors 102 are reversed shaped to be closer on the bottom and wider apart at the top. Some embodiments, coax outer conductors 102 are tuned to accommodate sensing of any particular molecule. For smaller sized molecules, such as inorganic molecules for example, the walls of the coax outer conductor may be closer together and be ranged between 20 nm and 100 nm. In other embodiments, the walls of coax outer conductor may be designed to be about 500 nm to 2 micrometers apart. In further embodiments, the walls of the coax outer conductor 102 may be even between 2 micrometers and 10 micrometers apart.

The inner conductor may 101 may be any suitable conductive nanostructure. Examples of materials that can be used for the include but are not limited to, carbon fiber; carbon nanotube; pure transition metals such as nickel (Ni), aluminum (Al), or chromium (Cr); metal alloys, e.g. stainless steel (Fe/C/Cr/Ni) or aluminum alloys (Al/Mn/Zn); and metallic polymers. Other possibilities are highly doped semiconductors, and semi-metals (metals with vanishingly small band gap, e.g. graphite). In an embodiment, the internal electrode 101 is a carbon nanofiber, such as carbon nanotube, for example a SWCNT or MWCNT.

As described above the inner conductor 101 above may be a non-conducting nanostructure coated with a conducting (e.g., metallic) material. For example, the inner electrode may include a polymer (e.g., SU-8) nanopillar coated with a metallic material (e.g., Al, Cr, etc.). Arrays of such polymer nanopillars may be fabricated using nano-imprint lithography (NIL) techniques, e.g. using an array of silicon nanopillars as an NIL master.

Although in FIG. 5D, the inner electrode 101 is shown having a cylindrical shape, any other suitable shape may be used, including a conical, trapezoidal, tapered, or other shape. In some embodiments, the shape may be truncated.

The nanosensor may be tuned or modified to accommodate detection of any particular molecule. For example, a sensor may be designed to have a particular porosity of the nanoporous material 104 as well as a particular diameter of the coax outer conductor 102 tuned to filter out, or at least bias against, some molecules while being able to bond with other molecules. Similarly, the nanosensor may be designed to have the sizes of the pores themselves be fine-tuned to accommodate particular molecules, based either on the sizes of the molecules being targeted or their chemical and physical properties. In addition, the nanoporous material 104 may be functionalized or coated with any coating or material that further helps with binding or attracting the target molecules. Since the porous material comprises a larger surface area than a nonporous material, having the functionalizing coating go into the pores may increase the functionalizing effects. In some embodiments, materials, such as aminopropyltriethoxysilane (APTES) may be used to functionalize the nanoporous material 104 to improve the sensing capabilities with respect to TNT or DNT materials. In some embodiments, additional surfaces of the sensor may be functionalized, including surfaces of the inner conductor 101 and the outer coax conductor 102, or exposed surfaces of the nonporous material 105, as discussed below.

Other substances such as peptides, amino acids, can be used to specifically recognize and immobilize target macromolecules such as lipids, proteins, antigens, nucleic acids, peptide nucleic acids (PNAs), etc. Embodiments may also use any of numerous conjugation schemes known in the art, usually involving a coupling agent such as 3-aminopropyltriethoxysilane (APTES, mentioned above), streptavidin-biotin, gold-thiol, silica, etc. to aid in the capture of targets.

In the nanosensors shown in FIG. 5D (e)-(g), the size of the nanocavity may also be tuned to provide enhanced selectivity to a certain analyte or class of analytes, (e.g., certain biomolecules), as described in detail herein. Further, in such embodiments, the exposed surfaces of the nonporous coating 105 may be functionalized. In some embodiments, this functionalization may be the same as or different than functionalization of the nanoporous material 104. In cases where different functionalization is used, the sensor can be made selectively sensitive to multiple targets. For example, in the embodiment shown in FIG. 5D (g), different functionalization may be applied to each of the nanoporous material 104, the nonporous material 105 in the inner conductor 101, and the nonporous material on the outer conductor 102, thereby sensitizing the sensor to three different targets.

Note that although FIG. 5D shows various types of sensors on a single substrate 107 for illustrative purposes, in general only one type or any suitable combination of types may be used In some embodiments, nanosensors (or arrays thereof) tuned to different analytes may be integrated into a single sensing device (e.g., as described in greater detail herein), to allow for the detection of multiple analytes and/or particular combinations of analytes. For example, a single integrated sensing device may feature a first set of nanosensors resembling that shown in FIG. 5D (b)-(d) with a nanoporous material with porosity and pore sized tuned to detect an inorganic compound. The integrated sensing device may additionally feature a second set of nanosensors resembling that shown in FIG. 5D (e)-(g) featuring a nanosensor with a nanocavity having a size tuned to detect a specific biomolecules or class of biomolecules. Accordingly, when both sets of sensors detect the presence of their respective analyte, the presence of both the organic compound and the biomolecules is indicated. In various embodiments, any other number or type of tuned nanosensors may be used.

In some embodiments, multiple arrays of sensors of a given type may be integrated on a single chip or similar device (e.g., to form an array of sensor arrays), allowing for the convenient simultaneous detection of multiple analytes.

In various embodiments, nanosensors of the type described herein may detect analytes at the part per billion level, part per trillion level, or less, e.g., allowing single molecule detection. In some embodiments, the nanosensor may detect a volatile organic chemical (e.g., methanol, ethanol, propanol, acetone, hexane, cyclohexane, etc.) present in an inert gas (e.g., $N_2$) at a concentration of 10 ppb, 1 ppb, 0.1 ppb, 0.01 ppb, 0.001 ppb, or even less, e.g., in the range of 0.001 ppb-10 ppb or any subrange thereof.

Figure 5E:
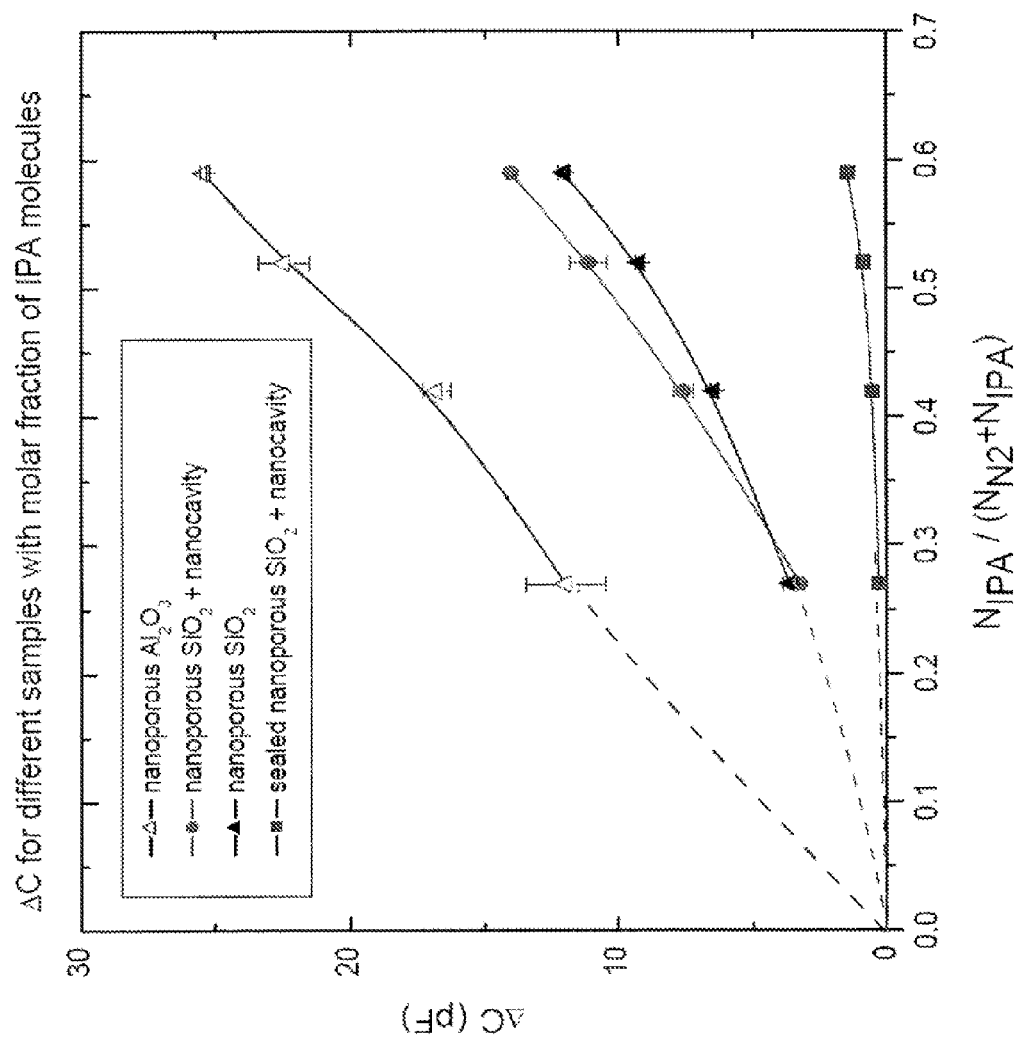
FIG. 5E shows results of the embodiments of the nanoporous nanosensors.

FIG. 5E shows exemplary sensing results for nanosensor devices of the type shown in FIG. 5D with and without nanocavities, and featuring various materials used for the dielectric material in the coax structure. The various sensors were exposed to isopropyl alcohol (IPA) molecules in a nitrogen gas, and the capacitance response of the sensors measure for various molar fractions of the IPA (using methods and techniques of the type described in the Examples below). The figure shows the resulting change as a function of IPA molar fraction. The greater the dynamic range of the response, the more efficient/sensitive the device is in detecting the IPA analyte.

In brief overview, results from a sealed nanoporous $SiO_2$ nanosensor with a nanocavity comprising a nanosensor with a nonporous material sealing the nanoporous $SiO_2$ material beneath are illustrated as the least efficient. The reasoning may be that the nonporous material capping the nanoporous $SiO_2$ prevents the molecules from getting into the nanopores, thus reducing the efficiency (i.e., sensitivity) of the device.

The results for a nanoporous $SiO_2$ nanosensor (without a nanocavity) show an increased efficiency relative to the capped device. This device includes a nanoporous $SiO_2$ material filling the annulus of the nanosensor. The nanoporous $SiO_2$ nanosensor resembles the nanosensors from FIGS. 5(b)-(d) having $SiO_2$ as the nanoporous material.

Still better efficiency is found for a nanoporous $SiO_2$ nanosensor with nanocavity. This nanosensor resembles the nanosensors from FIG. 5(a) comprising $SiO_2$ partially filling the annulus, leaving a nanocavity in the end of the coax structure. The results of the nanoporous $SiO_2$ with nanocavity reflect a more sensitive sensor than the results of the nanoporous $SiO_2$ (without cavity) and sealed nanoporous $SiO_2$ with nanocavity.

FIG. 5E further illustrates results for nanoporous $Al_2O_3$ nanosensor (without a nanocavity) which exhibits even higher efficiency than other devices illustrated. This device resembles the nanosensors from FIGS. 5(d)-(e) comprising $Al_2O_3$ as the nanoporous material. It may be anticipated from these results that a nanoporous $Al_2O_3$ device with nanocavity, in other words a device resembling the nanosensors from FIGS. 5(e)-(g) using $Al_2O_3$ as the nanoporous material, may be a more efficient sensing device.

Figure 6:
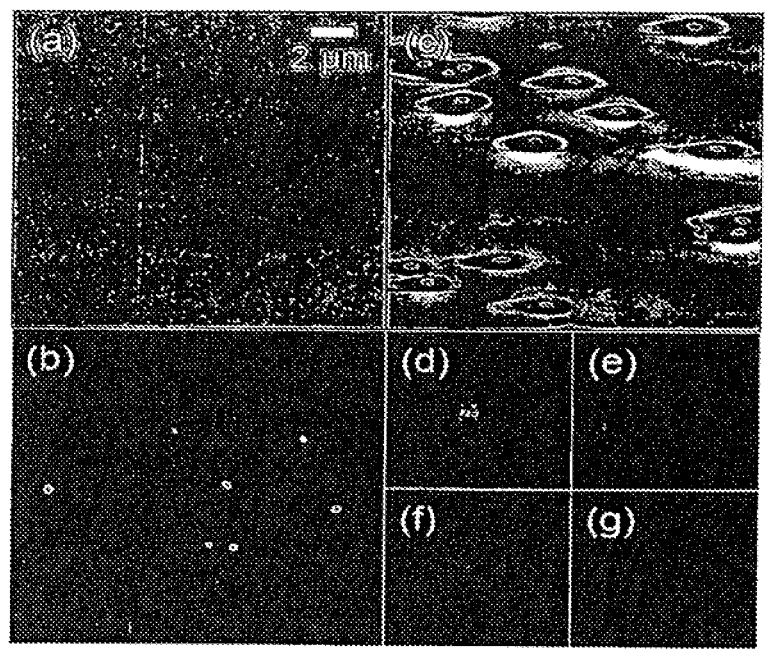
FIG. 6A-6G show the results of a small-area reflection and transmission experiment of a nanoscale coaxial transmission line according to an embodiment of the present invention.

FIG. 6A-6B show results of optical reflection and transmission from and through the apparatus 500 of FIG. 5A. In the high resolution optical microscope image of FIG. 6A, white light is reflected from the top surface of the sample, showing the topography, with dark spots due primarily to absorption of light by the transmission lines 510. When the light is incident from the back-side (i.e. that with the antennae), the light is transmitted along the transmission lines 510 and emerges at the top surface, as seen by the white spots in FIG. 6B for the same region of this sample.

The SEM image in FIG. 6C shows the top surface of another area of the sample at the same magnification (tilted view). The transmitted light remains white, FIG. 6B, which suggests no cut-off frequency, which is in agreement with transmission results for a larger area of this sample. FIGS. 6D and 6F show images of green and red laser beams passing directly through the glass substrate, and projected onto a screen. FIGS. 6E and 6G show the corresponding images for the laser beams transmitted through the apparatus 500. The relative intensity of the transmitted light, in each case, was obtained from RGB histograms. The overall transmission coefficient (T) for the apparatus 500 is about $10^{-3}$, in the visible range. While this value is small, it is within the expected range, given the absence of a nanoantenna on one side of each transmission line 510. Transmission (either for an array 500 or a single transmission line 510) increases with $\lambda$, and thus there is no cut-off frequency in this range, again as expected for a coaxial transmission line. The dependence of T on the transmission line 510 length has been measured, by polishing the sample to various sample thicknesses. Transmission from a large area of the sample (at $\lambda=532$ nm) is obtained as before from a RGB histogram at each polishing stage (i.e., for sample thickness of 6.2, 3.5, and 0.5 µm).

Figure 7:
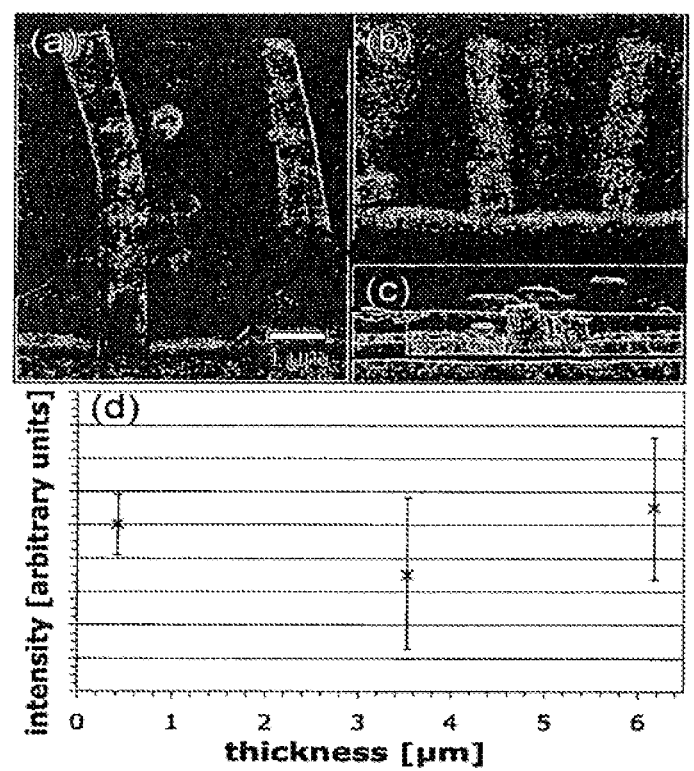
FIG. 7 shows SEM images of the cross-section of the nanoscale coaxial transmission line medium at different transmission line lengths: 6 µm (FIG. 7A), 3.5 µm (FIG. 7B), and 0.4 µm (FIG. 7C).

FIGS. 7A-C show SEM images of the polished edge of the transmission lines 510 medium, with nanocoaxes clearly visible. The scales are the same in all figures. FIG. 7D is a plot of intensity versus sample thickness and shows that T is essentially independent of thickness (i.e., the transmission line 510 length). This is consistent with the theoretical value of L being about 50 µm as stated above, which is much greater than the film thickness at each stage of polishing.

The nanoscale coaxial transmission lines 500, in addition to being a subwavelength transmission line having applications in nano-optics, also facilitates many novel approaches by enabling subwavelength, nanoscale manipulation of visible light. By replacing the inter-electrode dielectric material with a nonlinear material in each nanoscale coaxial transmission line, one may achieve light mixing, switching or phase conjugation. The nanoscale coaxial transmission line medium processes the transmitted light in a discrete manner by breaking the incoming wave into wavelets, and then re-assembling the plane wave on the other side of the medium. Having control over the transmission through individual nanoscale coaxial transmission lines enables control over the re-assembled outgoing waves, which may be the basis for a new discrete optics. The nanoscale coaxial transmission line structures described herein can be fabricated from a wide variety of materials. The inner and outer conductors can be made from any appropriate metal, using soft (e.g. templated electrodeposition, CVD) or hard (electron or focused ion beam lithography) techniques, and the choice of dielectrics is extensive. Moreover, the coupling of radiation (light) to the nanoscale coaxial transmission line can be achieved in ways other than the linear antenna described herein. For example, rather than coupling the inner conductor on the substrate side, coupling can be achieved on the opposite end of the coaxial transmission line (i.e., on the distal end of the inner conductor), such as by extending the distal end of the inner conductor beyond the distal end of the inner conductor.

Figure 8A:
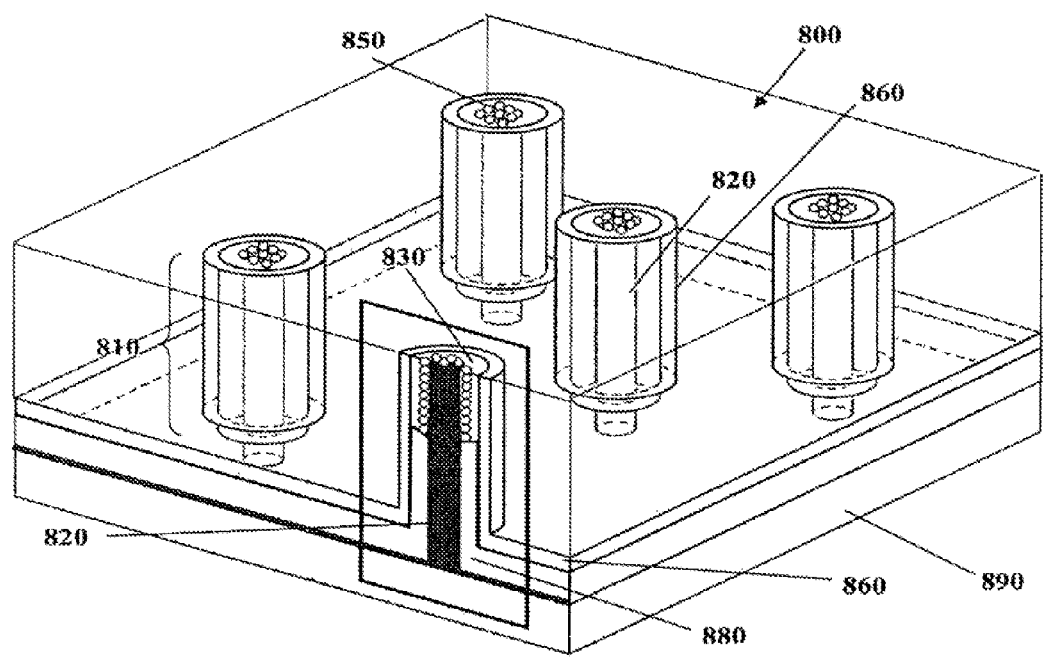
FIG. 8A-8B show a nanocoaxial sensors according to an embodiment of the present invention.

FIG. 8 shows a nanoscale sensor array 800 according to one embodiment of the present invention. The nanoscale sensor array 800 comprises an array of nanoscale sensor unit structures 810 distributed on a metallized substrate 890. The array of nanoscale sensor unit structures 810 may be arranged in a uniform, periodic or random distribution on the substrate 890. For example, the structures 810 may be arranged in a hexagonal pattern on the substrate 890. The array of nanoscale sensor unit structures 810 may be aligned in rows or unevenly distributed on the metallized substrate 890. The metallized substrate 890 may be transparent. The metallized substrate 890 may be composed of a polymer, glass, ceramic material, carbon fiber, glass fiber or combinations thereof onto which a layer of metallic material is deposited. Those skilled in the art will recognize that the substrate may be other materials known in the art and be within the spirit and scope of the presently disclosed embodiments.

An array of vertically aligned conductors 820 (e.g., multi-walled carbon nanotubes or other types of nanowires or nanofibers) are grown or attached to the substrate 890. The conductors 820 are coated with a dielectric material 880. The conductors 820 are then coated with a metallic layer 860 acting as the outer conductor.

The nanoscale sensor apparatus 800 includes vertically aligned carbon nanotubes 820 grown on a glass substrate coated with a thin (about 10 nm) chromium layer. On this layer nickel catalyst for PECVD growth of nanotubes was deposited electrochemically. The nanotubes 820 were coated with about 150 nm of aluminum oxide as the dielectric material 880 and with about 100 nm of chromium as the metallic layer 860. The entire array of nanoscale sensor unit structures 810 was filled with spin-on-glass (SOG) which does not affect array functionality but allowed the top part of the nanoscale sensor unit structures to be mechanically polished off. In an embodiment, the thickness of the SOG is about 6 µm. The nanotube 820 in each sensor unit structure 810 has the same length, unifying the array surface. Consequently, the capacitance of every nanoscale sensor unit structure 810 will be close to the same. Nanocavities 830 are formed by chemically etching at least a portion of the intermediate dielectric layer 880 between the electrodes 820 and 860. A nanocavity is opened for every nanoscale sensor unit structure 810. The nanocavity 830 is adapted to capture target species. Significant impedance change will be produced corresponding to the molecular accumulation in the nanocavity 830. A complete nanoscale sensing unit structure 810 is finished upon the addition of sensing elements 850 onto nanotubes 820. These sensing elements 850 provide specific recognition of the target species.

Figure 8B:
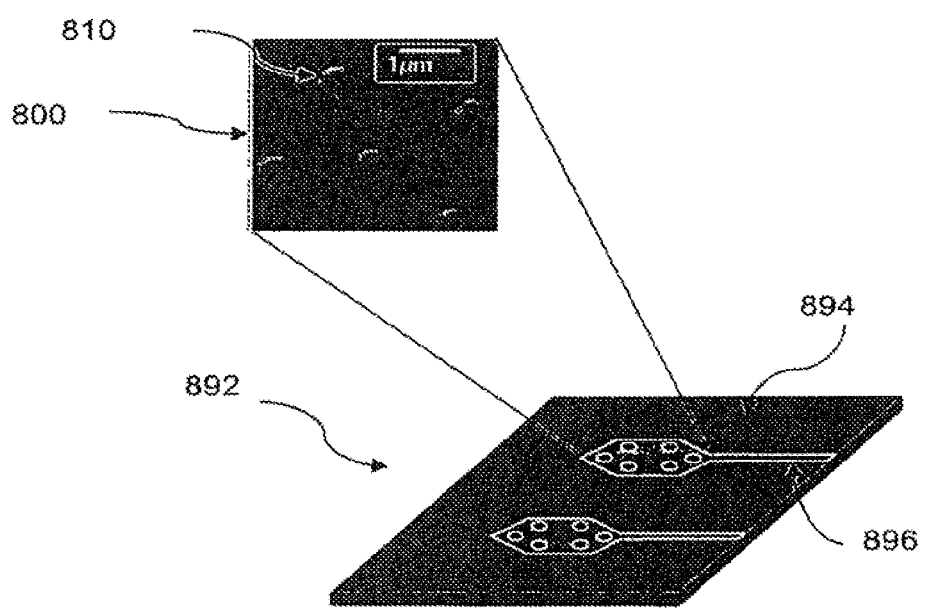

FIG. 8B shows a sensor device 892 comprising the nanoscale sensor array 800 containing individual unit structures 810. Optionally, the device 892 may be integrated with on-chip microfluidics. For example, a microfluidic inlet channel 894 provides a liquid solution to the array 800. After the solution has been tested for the presence of target species by the array 800, the solution is removed through a microfluidic outlet channel 896. Each unit structure 810 in a given array 800 may test for the same or different target species. The sensitivity of the device 892 is amplified by the number of unit structures 810 in the array 800, which, as shown in the inset SEM image in FIG. 8B, can be about $10^8/cm^2$ or less. The volume of solution provided to the array can be on the order of a few attoliters (1 aL=$10^{-18}$ L) or greater.

Figure 9A:
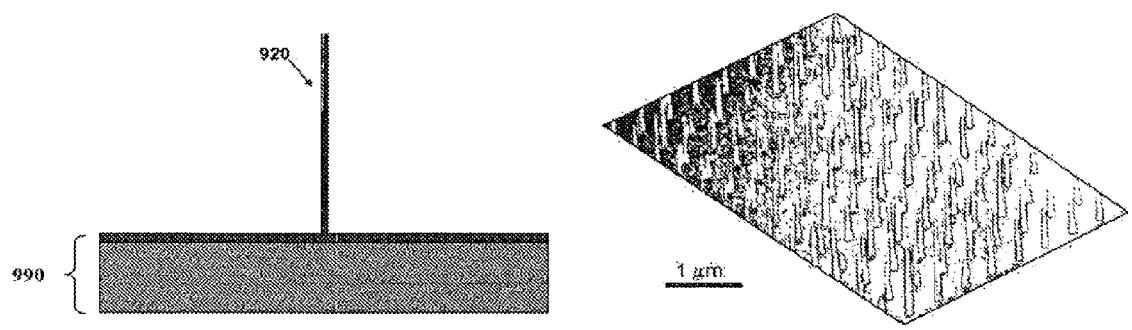
FIG. 9A-9F show the steps used for fabricating a nanoscale sensor according to an embodiment of the present invention.

FIG. 9A-9F show a method of making a nanoscale sensor apparatus according to an embodiment of the present invention. In FIG. 9A, catalyst particles, such as Ni nanodots, are deposited on a metallized substrate 990. In an embodiment, the metallized substrate 990 is a Si wafer coated with a metallic coating such as chromium. Carbon deposition is catalyzed underneath the Ni nanodots and forms a highly registered nanotube array with the presence of certain gasses, plasma, and high temperature (for simplicity, the schematic image shows a single nanotube 920). Typically, the nanotube 920 diameter is about 50-150 nm.

Figure 9B:
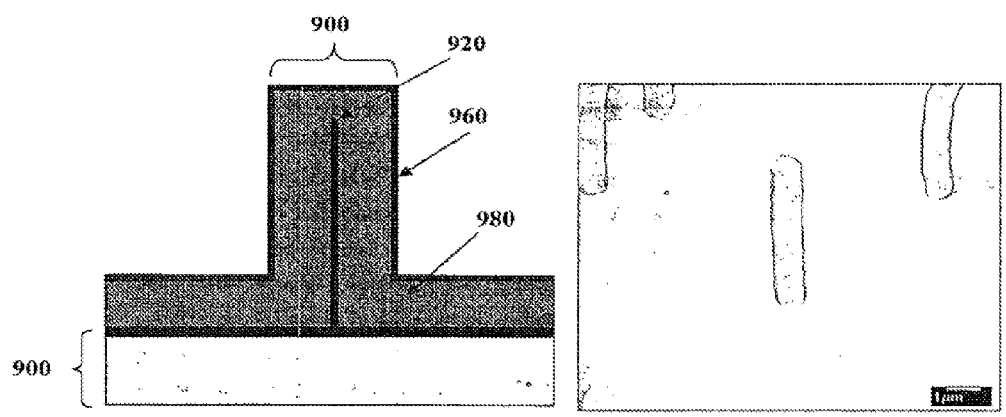

FIG. 9B shows a nanoscale coaxial transmission line 900 after the addition of a dielectric material 980 and a metallic layer 960 on the nanotube 920. In an embodiment, the dielectric material 980 is alumina and the metallic layer 960 is chromium. Depending on the size of the target molecule particles for detection, the dielectric 980 thickness can be adjusted from tens of nm to hundreds of nm, such as about 10 nm to about 500 nm. Both layers are deposited by sputter coating techniques.

Figure 9C:
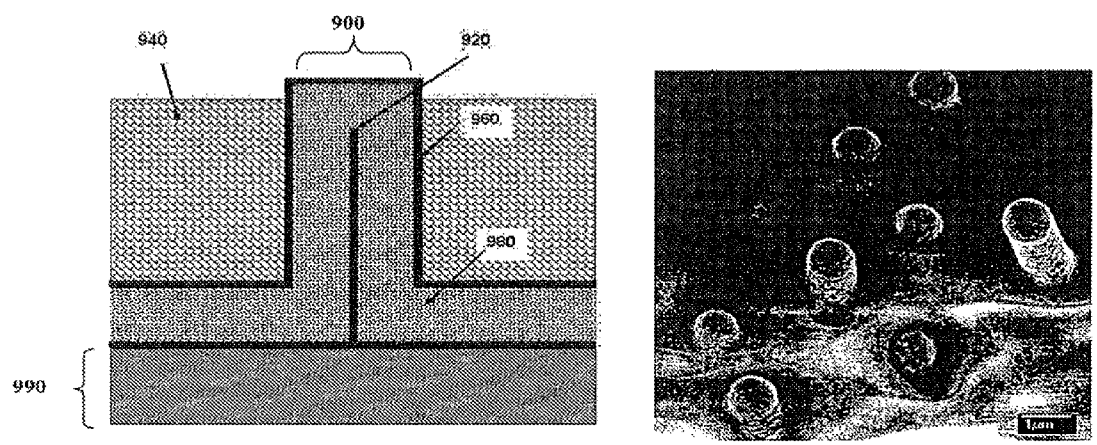

FIG. 9C shows the nanoscale coaxial transmission line 900 after spin-coating of a thick dielectric material 940. The dielectric material 940 should be biocompatible, insulative, stiff, water-resistant, and non-adhesive to biomolecules. In an embodiment, the dielectric material 940 is spin-on-glass (SOG). Alternatively, the material 940 is an epoxy, such as "Epon 828".

Figure 9D:
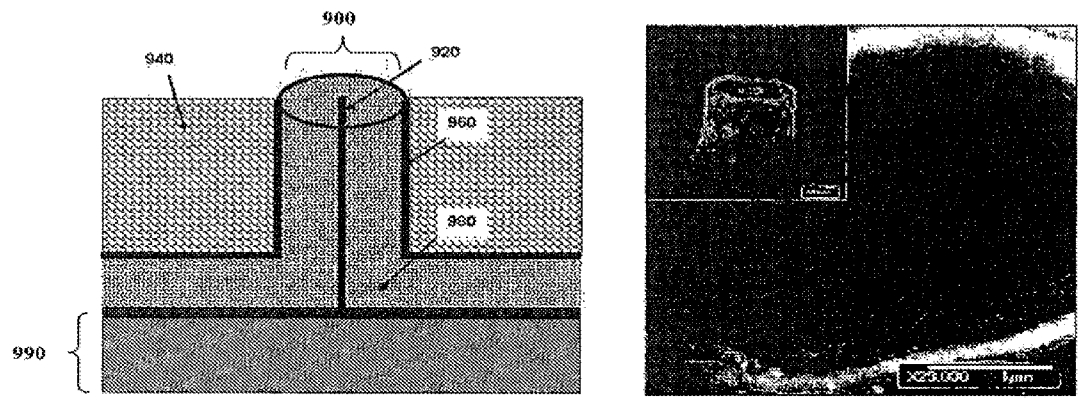

FIG. 9D shows the nanoscale coaxial transmission line 900 after mechanical polishing the tops of the nanoscale coaxial transmission lines 900 of FIG. 9C. The nanotube 920 in each nanoscale coaxial transmission line 900 has substantially the same length. Consequently, the capacitance of the nanoscale coaxial transmission line 900 will be close to the same.

Figure 9E:
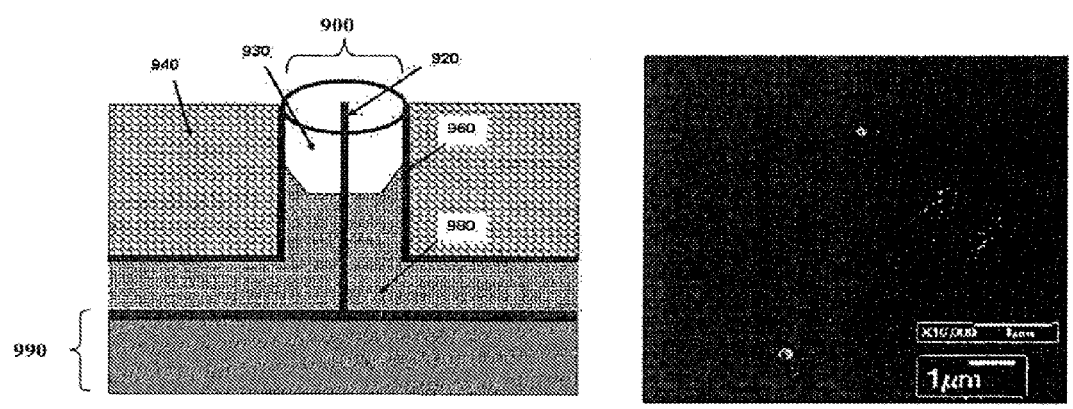

FIG. 9E shows the creation of nanocavities 930 in the nanoscale coaxial transmission lines 900. Nanocavities 930 are created by chemically etching the intermediate dielectric layer 980 between the nanotube 920 and the outer metal electrode 960. The nanocavity 930 provides size-dependent physical selection of target species entering into the nanocavity. The nanocavity is open at the top surface of the coaxial transmission line 900 to allow species having a size greater than the opening to enter into the nanocavity and to prevent species having a size greater than the opening from entering into the nanocavity. Significant impedance change will be produced corresponding to the capture of target species in the nanocavity 930. Partial etching of the dielectric layer 980 avoids nanotube 920 collapse due to surface tension. Preferably, etching is stopped before the nanotube 920 is shorted to the outer electrode 960. For example, the length of the nanotube 920 that is not surrounded by the dielectric layer 980 is about 50 nm to about 600 nm, such as about 100 nm to about 300 nm. In the high magnification SEM image in FIG. 9E, a developed cavity structure is broken on purpose to show the internal nanotube 920 component.

Figure 9F:
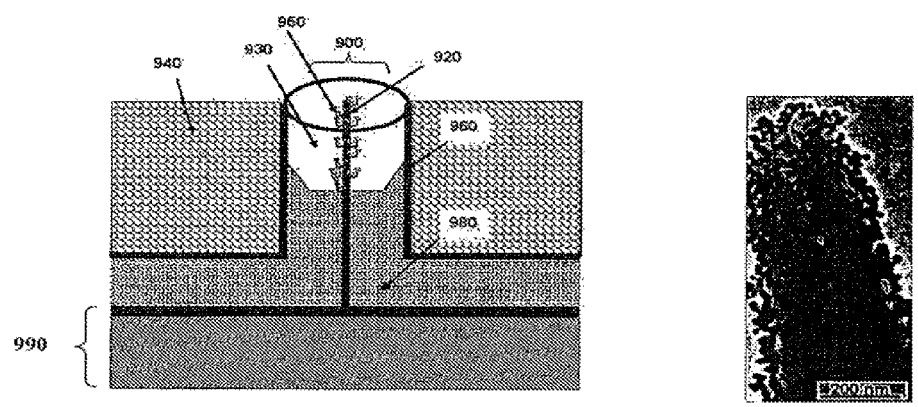

FIG. 9F shows the immobilization of sensing elements (e.g., molecules) 950 onto the top portion of the carbon nanotubes 920. Ferritin proteins were immobilized on the CNT by amide linkage, and the crystalline iron cores of the ferritin proteins are visible in the TEM image in FIG. 9F. The immobilization can be done by established covalent or non-covalent methods. The carbon nanotube 920 can be functionalized by chemical groups, or small molecules that carry the reactive groups, such as carboxylic acid, amine, and thiol groups. Functionalization can be performed by, for example, oxidation using a strong acid, nitrene addition, acrylation using diazonium salts, and 1,3-dipolar cycloadditions. For example, the carbon nanotube 920 is covalently functionalized with different types of small molecules to form the following molecular structures: 1) Ammonium-functionalized CNT; 2) Acetamido-functionalized CNT; 3) Fluorescein isothiocyanate (FITC)-functionalized CNT; 4) CNT bifunctionalized with ammonium and FITC; 5) CNT bifunctionalized with methotrexate (MTX) and FITC; 6) CNT bifunctionalized with amphotericin B (AmB) and FITC; 7) CNT bifunctionalized with ammonium and FITC. These groups will render the covalent linkages with the macromolecules. In a non-covalent version, for example, the chemical groups carry electro-charges and can facilitate the electrostatic attraction of macromolecules on to the nanotube 920 surface. In another embodiment, non-covalent immobilization is performed by an electropolymerization process to coat the CNTs with conductive (e.g., polypyrrole) and non-conductive (e.g., polyphenol) polymers. The thickness of the polypyrrole coating can be controlled by the deposition parameters. On the other hand, the polyphenol deposition process occurs by a self-limiting process which will stop once a compact and completely insulative coating is formed. The polymer coating can be doped with nanostructures (e.g., gold nanoparticles) or biomolecules (e.g., glucose oxidase which specifically binds to glucose). Another non-covalent strategy is based on the hydrophobic interaction. The nanotube 920 surface is originally hydrophobic. It is "sticky" to some macromolecules having hydrophobic residues. This mechanism can also be used to functionalize the nanotube 920 with small amphiphilic molecules. These molecules can be docked on the nanotubes 920 by its hydrophobic part. The hydrophilic end then can participate in the direct linkage or interaction with the macromolecules for immobilization. Many different CNT chemistries, including covalent and non-covalent chemistries, can be used to immobilize the active sensing elements on CNTs. For example, the methods described by D. Tasis et al., "Chemistry of Carbon Nanotubes," *Chem. Rev.* 106, 1105-1136 (2006) and K. Kostarelos et al., "Cellular uptake of functionalized carbon nanotubes is independent of functional group and cell type," *Nature Nanotechnology* 2, 108-113 (2006), all of which are incorporated herein by reference in their entirety, can be used.

A complete nanoscale sensing unit structure 900 will be finished upon the addition of active sensing elements 950 onto the top portion of the nanotubes 920. These active sensing elements 950 provide specific recognition of the sensing target species. The specificity is originated from the biological nature of biomolecule recognitions, such as antigen-antibody binding, complementary pairing of nucleotide molecules, targeted protein binding to certain DNA sequences, and specific catalytic activity to the chemical processes of their target molecules, etc. The sensor 900 will work in a fluidic environment that provides the compatibility to the biological activities of the molecules on nanotubes 920 or as the targets dissolved in the buffer.

The capture of the targeted species can be transduced to electric signals by the sensor 900 through different mechanisms, such as the changes in sensor impedance, capacitance, and Faradic current, etc. Detection can be performed by dielectric spectrometry, capacitance measurement (as of modified from that combined with patch clamp technique to measure femto fara level change in membrane capacitance), time-domain spectroscopy, waveguide resonators at THz frequencies, and electrochemical signals from the oxidant or reductant species in the nanocavity 930. The sensor 900 can detect biological processes occurring within the nanocavity 930, such as molecular redox reactions, enzyme catalyzed reactions, ligand-receptor and antigen-antibody interactions, DNA-protein binding and DNA stand duplexing.

A method of immobilizing sensing elements onto nanoscale coaxial transmission lines includes immersing an array of vertically aligned conductors of submicron to tens of microns in length supported on a metallized substrate in oxidative acids at room temperature overnight; rinsing the array with de-ionized water followed by critical point drying; sputtering the array with a dielectric material; sputtering the dielectric coated array with a metallic material to form external conductors; spin coating the array with about 1 to about tens of microns of insulating material; polishing the top of the array to expose a top portion of each of the conductors; immersing the array in etchant to partially etch off an area of dielectric material located at a top portion of the conductors to develop a nanocavity; immersing the array in a buffer solution to activate carboxyl groups on the conductors; adding in about 1 μg macromolecules containing primary amine groups to react with the functionalized conductors to form amide linkages; and rinsing the array with de-ionized water followed by critical point drying. In an embodiment, the array of vertically aligned conductors is an array of carbon nanotubes. In an embodiment, the oxidative acids may be about 0.5 M nitric acid or a mixture of 3 volume of 98% sulphric acid and 1 volume of 67% nitric acid. In an embodiment the dielectric material is sputtered onto the conductors at a thickness of about tens to about hundreds of a nanometer. In an embodiment, the metallic material is sputtered at a thickness of about 50 to about 200 nm. In an embodiment, the array is immersed in a buffer solution of about 0.1 M MES buffer (2-[N-morpholino]ethane sulfonic acid at pH 4.5) supplemented with 10 mgl-ethyl-3-(3-dimethylaminopropyl)carbodiimide (EDC). In an embodiment, the etchant to partially etch off an area of dielectric material is a sodium hydroxide solution, for example 100 mM sodium hydroxide solution.

An alternative method of immobilizing sensing elements onto nanoscale coaxial transmission lines includes depositing gold onto an upper portion of an array of vertically aligned conductors of submicron to tens of microns in length supported on a metallized substrate by e-beam deposition; sputtering the array with a dielectric material; sputtering the dielectric coated array with a metallic material to form external conductors; spin coating the array with about 1 to about tens of microns of insulating material; polishing the top of the array to expose a top portion of each of the conductors; immersing the array in etchant to partially etch off an area of dielectric material located at a top portion of the conductors to develop a nanocavity; incubating the array with 1 μg thiol modified macromolecules; and rinsing the array with de-ionized water followed by critical point drying. In an embodiment, the array of vertically aligned conductors is an array of carbon nanotubes. In an embodiment the dielectric material is sputtered onto the conductors at a thickness of about tens to about hundreds of a nanometer. In an embodiment, the metallic material is sputtered at a thickness of about 50 to about 200 nm. In an embodiment, the etchant to partially etch off an area of dielectric material is 100 mM sodium hydroxide solution. In an embodiment, the array is immersed in about 100 mM sodium hydroxide for about five minutes. In an embodiment the array is incubated with thiol modified macromolecules for about two hours.

An alternative method of immobilizing sensing elements onto nanoscale coaxial transmission lines includes immobilizing intermediate macromolecules with certain biorecognition properties to the bioreactive macromolecules, which are in charge of capturing the target bio-species. In an embodiment, the intermediate macromolecule is one of DNA probe, PNA (peptide nucleic acid) probe, aptamer, antibody, avidin, streptavidin, positively charged polymer, and/or negatively charged polymer. In an embodiment, the bioreactive macromolecule carries the ligand of the intermediate macromolecules, such as DNA, protein, biotin, or certain electric charge.

An alternative method of immobilizing sensing elements onto nanoscale coaxial transmission lines includes depositing gold onto an upper portion of an array of vertically aligned conductors supported on a metallized substrate by e-beam deposition; sputtering the array with a dielectric material; sputtering the dielectric coated array with a metallic material to form external conductors; spin coating the array with about 1 to about 10 micron of insulating material; polishing the top of the array to expose a top portion of each of the conductors; immersing the array in sodium hydroxide to partially etch off an area of dielectric material located at a top portion of the conductors to develop a nanocavity; incubating the array with streptavidin or thiol modified streptavidin to covalently link the macromolecules to the conductors; and rinsing the array with de-ionized water followed by critical point drying. In an embodiment, the array of vertically aligned conductors is an array of carbon nanotubes. In an embodiment the dielectric material is sputtered onto the conductors at a thickness of about tens to about hundreds of a nanometer. In an embodiment, the metallic material is sputtered at a thickness of about 50 to about 200 nm. In an embodiment, the array is immersed in about 100 mM sodium hydroxide for about five minutes. In an embodiment the array is incubated with thiol modified macromolecules for about two hours.

An alternative method of immobilizing sensing elements onto nanoscale coaxial transmission lines includes immersing an array of vertically aligned conductors supported on a metallized substrate in oxidative acids at room temperature overnight; rinsing the array with de-ionized water followed by critical point drying; sputtering the array with a dielectric material; sputtering the dielectric coated array with a metallic material to form external conductors; spin coating the array with about 1 to about 10 micron of insulating material; polishing the top of the array to expose a top portion of each of the conductors; immersing the array in sodium hydroxide to partially etch off an area of dielectric material located at a top portion of the conductors to develop a nanocavity; immersing the array in a buffer solution to activate carboxyl groups on the conductors; adding in amine enriched polymers to conduct aminization between the polymer and the conductors; rinsing the array with de-ionized water; transferring the array to neutral sodium chloride solution with about 1 μg macromolecules that carry negative charges at a pH of 7.0; incubating the array for about thirty minutes; and rinsing the array with sodium chloride solution followed by critical point drying. In an embodiment, the array of vertically aligned conductors is an array of carbon nanotubes. In an embodiment, the oxidative acids may be about 0.5 M nitric acid or a mixture of 3 volume of 98% sulphric acid and 1 volume of 67% nitric acid. In an embodiment the dielectric material is sputtered onto the conductors at a thickness of about tens to about hundreds of a nanometer. In an embodiment, the metallic material is sputtered at a thickness of about 50 to about 200 nm. In an embodiment, the array is immersed in a buffer solution of about 10 ml 0.1 M MES buffer (2-[N-morpholino] ethane sulfonic acid at pH 4.5) supplemented with 10 mgl-ethyl-3-(3-dimethylaminopropyl)carbodiimide (EDC). In an embodiment the amine enriched polymer is about 10 µl polylysine (0.01%, 70 Kd-140 Kd).

In an embodiment, goat anti-human antibody is immobilized on a nanoscale sensor of the presently disclosed embodiments, which enables the capture of human IgG target species in a solution. Impedance Spectroscopy measurements are performed with a Solartron 1470 Battery Test Unit and a Solartron 1255 B Frequency Response Analyzer (Solartron Inc., UK) for 2.5 mM $K_4[Fe(CN)_6]$+2.5 mM $K_3[Fe(CN)_6]$ in 0.1 M KCl+10 mM PBS (phosphate buffered saline) (pH 7.0) solution for the electrochemical detection of human IgG. A sinusoidal potential modulation of ±5 mV amplitude is superimposed on the formal potential of the redox couple of $[Fe(CN)_6]^{4-}/[Fe(CN)_6]^{3-}$ (0.22 V vs. Ag/AgCl). The redox couple provides a background impedance subject to be disturbed by the IgG binding. The change in the impedance is calculated and transformed based on the amount of molecular bindings. The impedance data may be fitted to the electrical equivalent circuit shown in FIG. 1B using the Zplot/Zview software (Scribner Associates Inc.). The equivalent circuit provides an electrical analogue of chemical/physical processes probed by Electrochemical Impedance Spectroscopy. Electrolyte solutions are deoxygenated by bubbling with high-purity nitrogen for at least 20 min. All measurements are carried out at room temperature.

Figure 10:
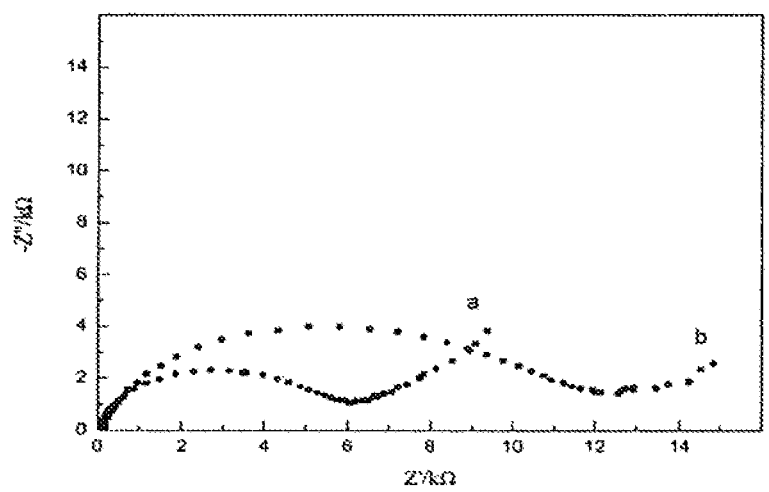
FIG. 10 shows a complex impedance (Nyquist) plot of a nanoscale sensor immobilized with goat anti-human antibody and the response to antigen, human IgG, binding. Trace a and b are the results before and after IgG binding.

In order to capture human IgG, the nanoscale sensor is immersed in a pH 7.0 phosphate buffer containing various concentrations of antigen, i.e. human IgG, at 37° C. for 30 min, followed by the rinsing of the nanoscale sensor in 0.01 M PBS (pH 7.0) solution to remove any unbound antigen. Impedance Spectroscopy measurements were then performed, and the results are illustrated by using a Nyquist plot, of which each point is the impedance at one frequency. A similar plot is shown in FIG. 10. The semicircle diameter will increase with the human IgG concentration, signifying that more amount of antigen was linked to the interface, and generating a larger inter-electrode resistance and stronger blocking to the electron transfer of the redox probe.

A typical shape of an electrochemical impedance spectrum includes a semicircle region lying on the Z axis and followed by a straight line. The semicircle portion, observed at higher frequencies, corresponds to the electron-transfer limited process, whereas the linear part is characteristic of the lower frequencies range and represents the diffusional limited electron-transfer process. In the case of a very fast electron-transfer process, the impedance spectrum could include only the linear part, whereas a very slow electron-transfer step results in a big semicircle region that is not accompanied by a straight line. The electron-transfer kinetics and diffusional characteristics can be extracted from the spectra.

Figure 11:
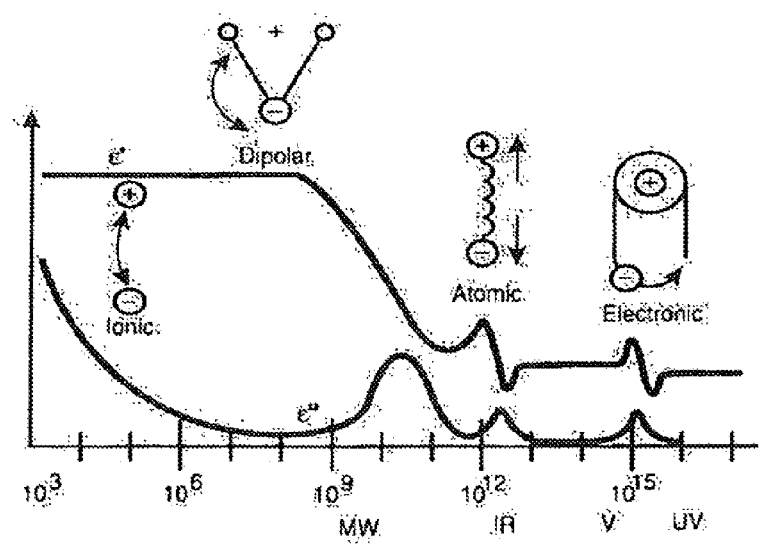
FIG. 11 shows a dielectric permittivity spectrum over a wide range of frequencies. The real and imaginary parts of permittivity are shown, and various processes are depicted: ionic and dipolar relaxation, and atomic and electronic resonances at higher energies.

As stated above, the equivalent circuit of FIG. 10 suggests the approach for detecting target species is Impedance Spectroscopy or Dielectric Spectroscopy. There are a number of different dielectric mechanisms, connected to the way a studied medium reacts to the applied field, as shown in FIG. 11. Each dielectric mechanism is centered around its characteristic frequency, which is the reciprocal of the characteristic time of the process. In general, dielectric mechanisms can be divided into relaxation and resonance processes. The most common, starting from high frequencies, are 1) Electronic polarization, this resonant process occurs in a neutral atom when the electric field displaces the electron density relative to the nucleus it surrounds; 2) Atomic polarization is observed when an agglomeration of positive and negative ions is deformed under the force of the applied field. This is also a resonant process; 3) Dipole relaxation, which originates from permanent and induced dipoles aligning to an electric field. Their orientation polarization is disturbed by thermal noise (which dis-aligns the dipole vectors from the direction of the field), and the time needed for dipoles to relax is determined by the local viscosity. These two facts make dipole relaxation dependant on temperature and chemical surrounding; and 4) Ionic relaxation, which is comprised of ionic conductivity and interfacial and space charge relaxation. Ionic conductivity predominates at low frequencies and introduces only losses to the system. Interfacial relaxation occurs when charge carriers become trapped at interfaces of heterogeneous systems.

Dielectric Spectroscopy has been used in materials science, and also in studying the electrical properties of biological materials. Impedance Spectroscopy is gaining renewed strength as a tool complementary to other techniques used to study the structural and related properties of proteins by providing important information about the protein's charge dynamics, as related to its structure. Impedance Spectroscopy is sensitive to polarization interfaces and intermolecular interactions, such as dipole-dipole interactions and cooperative processes.

Figure 12:
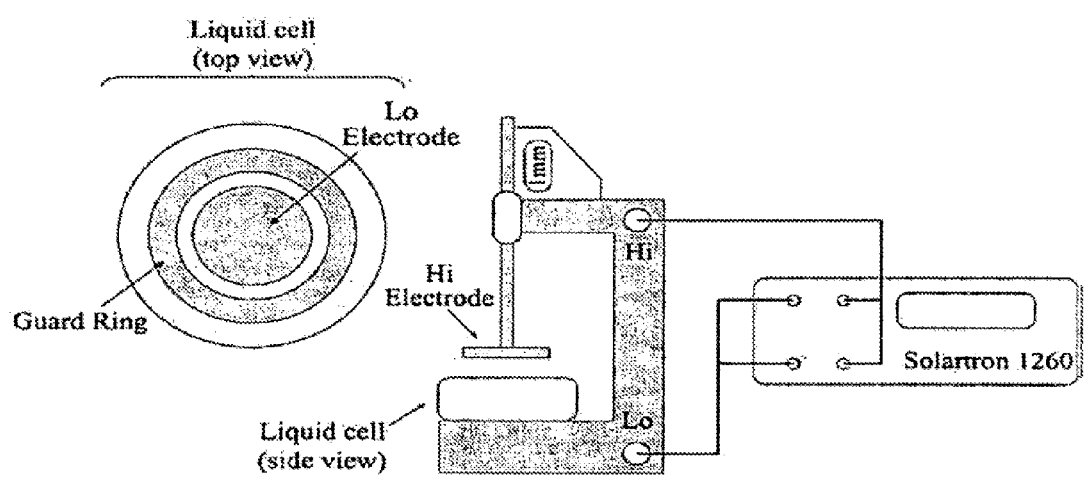
FIG. 12 shows an experimental setup of an Impedance Spectroscopy (IS) apparatus that may be used with the nanoscale ultrasensitive sensor unit structure according to an embodiment of the present invention.

FIG. 12 shows an experimental setup for Impedance Spectroscopy. For example, a Solartron 1260 impedance/gain-phase analyzer is used to sweep the frequency over a range of about 1 Hz to about 1 MHz. The liquid cell with stainless steel electrodes was 2 cm in diameter, and contained a guard ring that reduced fringing fields. The separation distance used in the experiments between the electrodes was 1 µm.

$$\Delta \varepsilon = (\varepsilon_s - \varepsilon_\infty) = \frac{g\mu^2 N_A C}{2\varepsilon_0 MkT} \quad (3)$$

Equation (3) tells us that, by measuring the low- and high-frequency-limiting dielectric constants, $\epsilon_s$ and $\epsilon_\infty$, one can calculate the dipole moment of the protein for given assumptions of g, thereby, to determine its identity based on the fingerprint. This relationship has been used for extracting with high accuracy the electrical dipole moment for other biomolecules, such as myoglobin, hemoglobin, DNA, etc. µ is the dipole moment of the protein, $N_A$ is Avogadro's number, C is the concentration in (mg/ml), M is the mass of the protein (kg/mol), k is the Boltzmann constant, T the absolute temperature, and g is the Kirkwood correlation factor, which is usually assumed to be 1.

Time Domain Dielectric Spectroscopy (TDDS) is based on the transmission line theory in the time domain and studies the heterogeneity in the coaxial lines according to the change in shape of a test signal. In this method a rapidly increasing voltage step arrives at the sampling head where the signal reflected from the dielectric sample is also registered. For the ideal system, the voltage applied to the sample is:

$$V(t) = V_o(t) + V_r(t)$$

where $V_o(t)$ and $V_r(t)$ are the incident and reflected signals, respectively. The expression for the flow of current through the sample is $$I(t) = \frac{1}{Z_0}[V_0(t) - R(t)]$$

where $Z_0$ is the characteristic impedance of the transmission line in the absence of a target specie between the conductors.

As long as the transmission line is homogeneous, the shape of this pulse will not change. But, in the case of heterogeneity in the line (for example, when a target specie is present between the conductors) the signal is partly reflected from the air-dielectric interface and partly passes through it. Dielectric measurements are made along a coaxial transmission line with the sample mounted in a sample cell that terminates the line.

FIG. 12 illustrates the experimental set-up used for the TDDS method according to an embodiment of the present invention. The recorded signals are shown in FIGS. 13 and 14.

Figure 13:
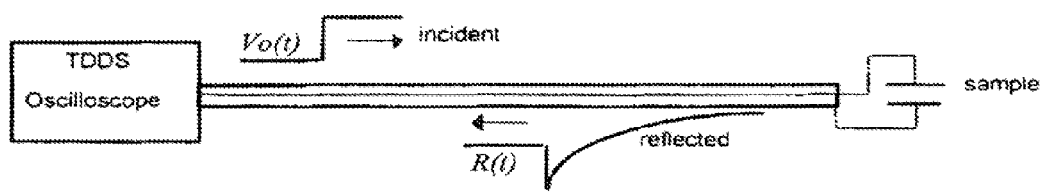
FIG. 13 shows a simplified block diagram of the set-up common for most Time Domain Dielectric Spectroscopy (TDDS) methods.

FIG. 13 is an illustration of the basic principles of the TDDS system, where $V_0(t)$ is the incident pulse and $R(t)$ is the reflected signal.

Figure 14:
FIG. 14 shows the characteristic shape of the signals recorded during a TDDS experiment as shown in FIG. 13.

FIG. 14 shows the characteristic shape of the signals recorded during a TDDS experiment.

The low-frequency conductivity ($\sigma$) of the sample can be determined directly in time domain. Here, $\epsilon_0 = 8.85 \times 10^{-12}$ F/m, and $C_0$ is the electric capacity of the coaxial sample cell terminated to the coaxial line.

$$\sigma = \frac{\varepsilon_0}{Z_0 C_0} \lim_{t \to \infty} \frac{V_0(t) - R(t)}{V_0(t) + R(t)}$$

FIG. 15A-15D are SEM images showing the steps used to fabricate an ordered pattern of nanocoaxial sensors according to an embodiment of the present invention. FIG. 15A shows a self-assembled mask of polystyrene nanospheres deposited on a substrate. E-beam deposition was used to deposit Ni catalyst in the interstices of the nanosphere mask. FIG. 15B shows the Ni catalyst after it was annealed to form a hexagonal pattern of Ni nanodots on the substrate surface. FIG. 15C shows the surface after CVD was performed to grow vertically-aligned CNTs at the catalyst sites. FIG. 15D shows an array of completed nanocoaxial sensors after the dielectric and outer conductors were deposited onto the CNTs. The distance between each nanocoaxial sensor can be adjusted by varying the size of the nanospheres. Other types of masks having different patterns can also be used. The spatial amplification of the nanosensor array can be adapted to scale linearly with the number of nanosensors in the array. For example, the array is group addressable. In an embodiment, the individual nanocoaxial sensors in an array are connected in parallel and the total capacitance of the array is the sum of the capacitance of each individual nanocoaxial sensor. In another embodiment, the individual nanocoaxial sensors in an array are connected in series and the total capacitance of the array is the inverse of the sum of the inverse capacitance of each individual nanocoaxial sensor.

FIG. 16A-16D show the precise placement and spatial arrangement of an ordered arrangement of CNTs formed on tungsten leads. FIGS. 16A and 16B are SEM images of tungsten leads formed on a Si substrate. The tips of the tungsten leads are spaced apart from each other, with gaps ranging from about 40 nm to about 1 µm. A single Ni catalyst nanodot having a diameter of about 100 nm is deposited on the tip of each lead, as shown in FIG. 16B. FIG. 16C shows an AFM image of the same leads. FIG. 16D is a SEM image of the leads after CNTs are grown from the Ni catalyst nanodots. Nanocoaxial sensors are formed around each CNT by depositing a dielectric and an outer metal layer around each CNT. Each nanocoaxial sensor in the array can operate independently of the others in the array. For example, the inner conductor of each sensor is not in electrical contact with any other inner conductor in the array, allowing each inner conductor to be probed at a different bias. The independently addressable array of nanocoaxial sensors allows multiplexing of the signal being provided by each sensor.

FIG. 17 shows four SEM images of nanocoaxial sensors having different sized nanocavity openings according to an embodiment of the present invention. The distance between the inner conductor and the outer conductor can be tuned by changing diameter of the inner conductor or the thickness of the dielectric material, or both. For example, when a CNT is used as the inner conductor, the diameter of the CNT can be controlled by the size of the catalytic Ni particle used. Also, the thickness of the dielectric material is controlled by the duration of the magnetron sputtering deposition. The depth of the nanocavity can be tuned by etching the dielectric material with different etchants or by varying the duration of the etching step, or both. The CNT diameter can be adjusted from about 40 nm to about 200 nm. The thickness of the dielectric can be adjusted from about 10 nm to about 500 nm. The depth of the nanocavity can be adjusted from about 50 nm to about 2000 nm. The nanocavity is adapted to exhibit a size-dependent physical selection of target species entering into the nanocavity. The size of the nanocavity opening is adjusted depending on the size of the target species to be detected by the nanocoaxial sensor. For example, a size of the nanocavity opening is selected such that substantially no molecules having a size greater than a critical size will enter into the nanocavity. The critical size is determined for a given target species, for example, by applying differently-sized target species, such as $E.$ $coli$ (ranging 0.5×1.5 µm to 0.8×2.2 µm) or SARS-CoV (ranging diameter 60 nm to 120 nm), to an array of nanocoaxial sensors of known opening size.

The nanocavities of the present invention are compatible with various methods for filling the nanocavities with solution. For example, the nanocavities are filled with solution by capillary action, whereby the nanocavity surface (e.g., the walls of the outer and/or inner conductors within the nanocavity) effectively draw the solution into the nanocavity by hydrophobic/hydrophilic interactions. Capillay action is optimized by judicious choice of conductor materials and carrier solvent. In addition, the solution can be drawn into the nanocavity by an electrowetting process, whereby an electrical potential is applied to the inner and/or outer conductors. For example, the electrowetting method described in an article by J. Y. Chen et al., "Electrowetting in Carbon Nanotubes," *Science* 310, 1480-1483 (2005), which is incorporated herein by reference in its entirety, can be used. Optionally, a supercritical filling process can be performed, including first filling the nanocavity with liquid carbon dioxide and then filling the nanocavity with the solution by substitution. For example, the supercritical filling process described in the article by X. B. Wang et al., "Nanofluids in carbon nanotubes using supercritical $CO_2$: a first step towards a nanochemical reaction," *Applied Physics A* 80, 637-639 (2005), which is incorporated herein by reference in its entirety, can be used. The target species can be labeled with magnetic and/or electrically charged nanoparticles and drawn into the nanocavities by magnetic and/or electrostatic attraction to complementary nanoparticles that are immobilized within the nanocavities. In an embodiment, the target species are magnetically and/or electrostatically drawn to the target species. Optionally, if CNTs are used as the inner conductors, an electrical potential is applied to the CNTs to enhance the electrostatic attraction.

Figure 18A:
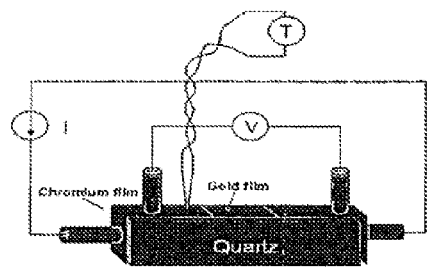
FIG. 18A-18C shows gold film nucleation and CNT functionalization according to an embodiment of the present invention.
Figure 18B:
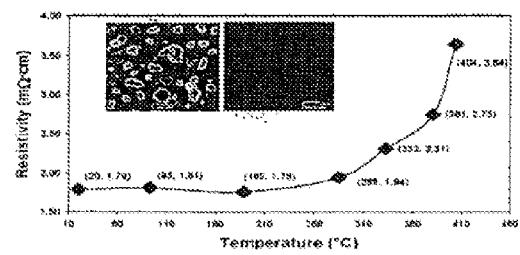

FIG. 18 shows nucleation of a gold film and CNT functionalization according to an embodiment of the present invention. FIG. 18A shows the experimental setup in which a gold film deposited on a quartz substrate was heated at a temperature (T) while its resistivity (mΩ·cm) was measured. FIG. 18B shows that the resistivity of the gold film increased exponentially as the temperature was increased from 270° C. to 450° C., above which the resistivity became to large to be measured, thus indicating the loss of electrical connection between the two electrodes. The inset of FIG. 18B shows SEM images of the gold film before (right) and after (left) the thermal anneal. As can be seen, the gold film nucleated into discreet and electrically isolated gold nanoparticles.

Figure 18C:
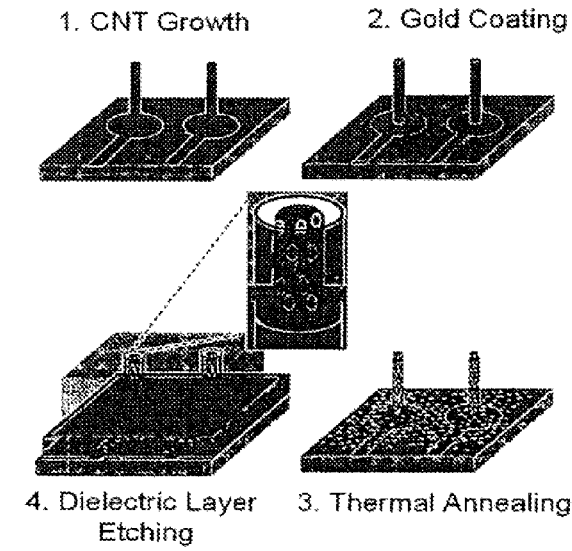
Figure 19A:
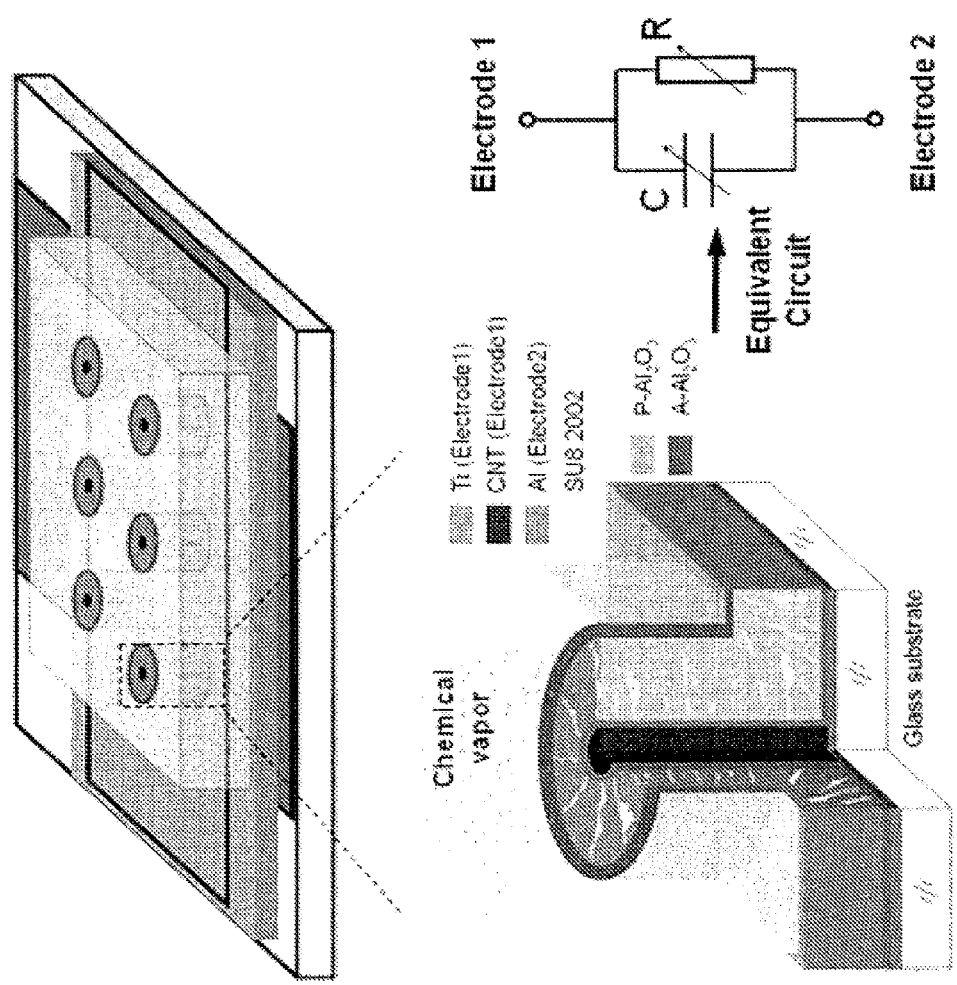
FIG. 19 A-B shows embodiments of nanoporous nanosensors.

FIG. 18C shows a method of functionalizing CNTs with gold nanoparticles. First, CNTs are grown by CVD or other suitable method on patterned electrodes, such as on the tungsten leads shown in FIG. 16A-16D. Second, the CNTs are coated with a gold film having a thickness of about 1 nm to about 12 nm by thermal or electron beam evaporation. Third, the gold film is annealed at a temperature greater than about 450° C., such as about 500° C. to about 650° C. for 45 min in a horizontal tube furnace with constant flowing Ar gas (50 sccm) and pressure of 5 Torr. The gold film is broken into discrete nanoparticles, and the CNTs grown on different electrodes are not in electrical contact with each other. Fourth, the gold-functionalized CNTs are coated with a dielectric material and then coated with an outer metal layer. At least a portion of the dielectric material is etched away to form a nanocavity and to reveal the gold nanoparticle-functionalized CNT. These gold nanoparticles are available for subsequent chemistries. For example, an anti-Fcγ antibody is modified with a thiol group through a C7 crank and is then bound to the gold nanoparticle-functionalized CNT. A secondary antibody (anti-SARS mAb) is then bound to the anti-Fcγ antibody for selective capture of SARS-CoV virus.

B. Multimodal Molecular Level Chemical Detection by an Array of Nanoaxial Structures A nanosensor described herein may, in addition to the above-identified features, also include a nanocoaxial dielectric impedance chemical sensor comprising an annulus filled with porous and nonporous layers. Described in the earlier sections is a coaxial nanocavity bio-chemical sensor that includes an annulus of the nanocoax forming a hollow cavity used to detect the presence of molecules entering the annulus. Detection of such molecules may be implemented by measuring changes in the capacitance and/or complex impedance across the nanosensor due to the dielectric constant of the molecule differing from that of the ambient material in said annulus.

In some embodiments, the nanosensor may be modified such that the annulus is not hollow, or at least, not entirely hollow. Instead, the annulus may be filled with a porous material. The porous material may include pore sizes, which may also be referred to as nanopores, and which may on the nanoscale of about between 1 and 100 nm in diameter. For example, the porous material filling the annulus may include the nanopores whose diameters may be between 1 and 10 nm, between 5 and 15 nm, or between 10 and 20 nm in diameter. In these embodiments, the target molecules may enter the pores and adsorb or bind onto the surfaces or walls of the nanopores inside the porous material. The adsorbed molecules may cause a change in effective dielectric constant of the coaxial capacitor, and thus induce a change in the capacitance and complex impedances. A nanosensor with a nanoporous material included in the annulus may have an advantage over other nanocavity detectors in that it has a larger surface area used the detection. The larger surface caused by the nanopores enabling the molecules to adsorb not only on the surface, but also inside the pores of the material, may cause the nanoporous nanosensor to have an increased physisorption (physical adsorption) as well as the increased chemisorption (chemical adsorption). In other words, the nanoporous nanosensor structure presented herein may have an increased probability of binding (and detecting) target molecules as well as an increased number of target molecules that can be detected in an individual nanoporous nanocoax. By increasing the probability of binding, this nanosensor may increase the total signal of the binding molecules detected. By increasing the number of target molecules that can be detected, this sensor may also increase the signal-to-noise ratio, thus making it the readings even more accurate.

In addition to the nonporous aspect of the dielectric annulus in the nanocoax chemical sensor discussed above, the nanoporous nanosensor may also include a thin nonporous dielectric. The thin nonporous dielectric may include a non-conducting, or electrically insulating film layer underneath the porous film layer. The nonporous layer may be situated between the coax inner metal conductor and the nanoporous dielectric layer. The nonporous layer may prevent electrical shorting of the inner and outer metals of the coaxial structure.

By introducing the porous dielectric medium in the annulus of the nanocoax, the nanoporous nanocoax chemical sensor may detect target molecules with more than 10 times more sensitivity than a nanocavity chemical sensor with no nanoporous material. Several different dielectric materials may be used as the nanoporous medium in the nanocoax annuli, such as aluminum oxide, silicon oxide, hafnium oxide, silicon nitride, activated carbon, vycor glass, zeolites, polymers, aerogels, and various metallic minerals and compounds of organic materials and metals or organic materials and silicon. In addition, the surfaces of the pores of such nanoporous materials may be modified or "functionalized" to facilitate or encourage specific binding of target molecules for detection, adding molecular specificity to the high sensitivity. In some embodiments, a nanoporous aluminum oxide may be functionalized with APTES for specific binding of TNT and DNT explosives.

In one example, a set of high density nanocoaxial arrays are used for molecular-level chemical detection and identification of various chemicals by nanospectroscopy. In an effort to combine specific nanoarchitectures with specific nanomaterials to improve detection capabilities, a nanoscale coaxial array architecture integrating nanoporous aluminum oxide and carbon nanowires may be used to conduct highly sensitive and multimodal electrical detection of a broad class of chemical molecules. In one such instance, a detection using ethanol was is achieved at 150 parts-per-trillion (ppt). Such detection capability may correspond to detection limits of each sensor unit at quasi-molecular level.

Referring now to FIGS. 19A-B, embodiments of the present example of a nanocoaxial array-based chemical detection platform is illustrated. The basic structure illustrated by FIGS. 19A-B may be composed of the CNT, alumina coatings by nonporous atomic layer (A-$Al_2O_3$) and porous sputter (P—$Al_2O_3$) deposition, and aluminum (Al)

coating applied by sputtering. The array may be supported by SU8-2002 polymer. As illustrated by FIG. 19A, the coaxial units may be mechanically polished to open access for the P—$Al_2O_3$ to chemical vapor. The outer (Al) and inner (CNT) coax conductors may form nanocoaxial cables whose equivalent circuit is a resistor (R) and capacitor (C) connected in parallel. As shown in the FIG. 19A, the CNT may be connected to the bottom titanium (Ti) forming "Electrode 1". The outer Al may form "Electrode 2".

Figure 19B:
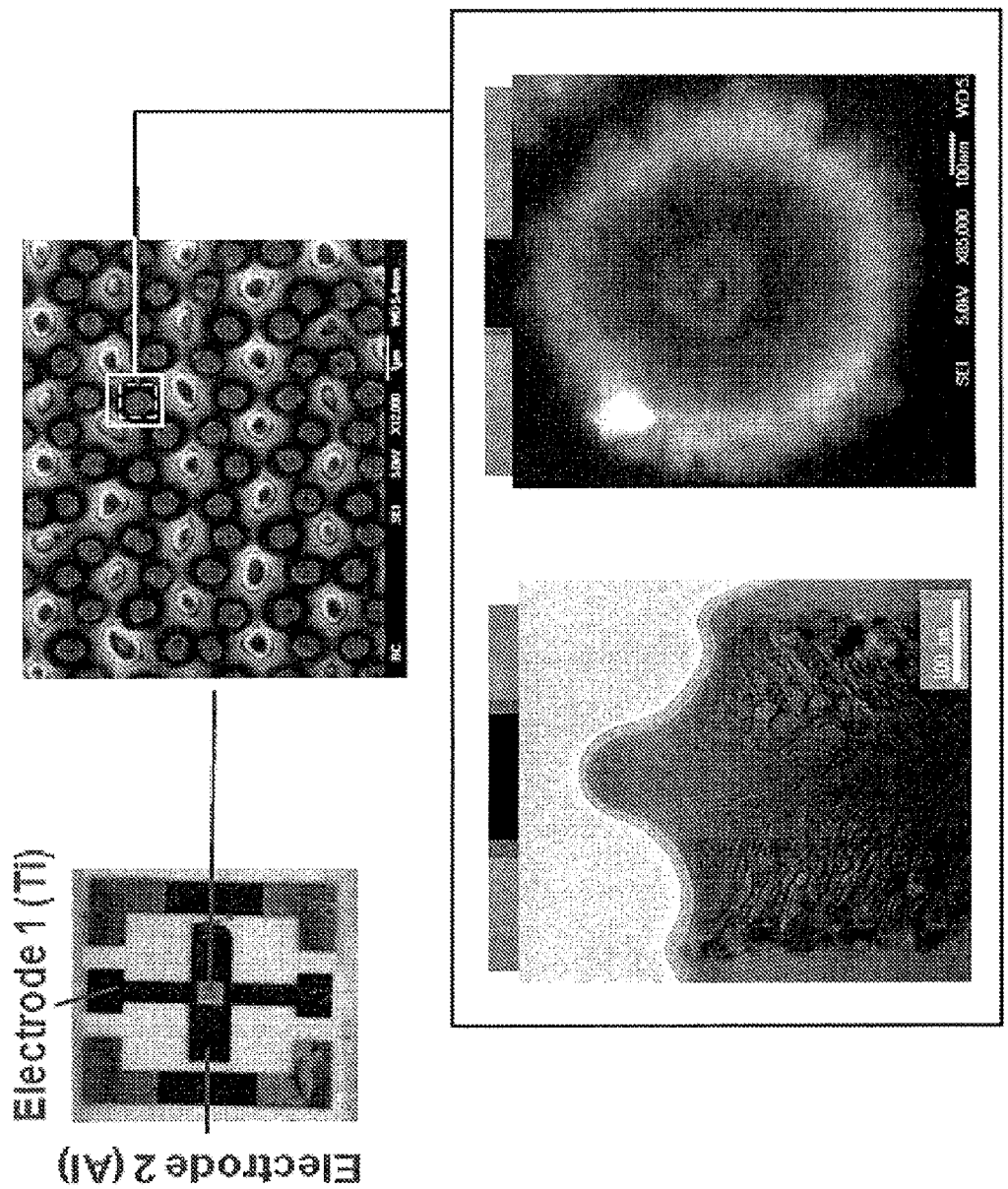

Referring now to FIG. 19B, a top view scanning electron microscope (SEM) image at low magnification shows a periodic array of identical nanocoax units. Electrodes 1 and 2, as expressed in FIG. 19A are shown using SEM and TEM images at higher magnifications at the lower part of the FIG. 19B, in which multiple components of a unit may be clearly observed, indicated by color code above the images. In some embodiments, in contrast to A-$Al_2O_3$, P—$Al_2O_3$ may capture chemical molecules by chemophysical adsorption, leading to changes in the sensor impedance as well as its components, R and C.

Further in reference to FIGS. 19A-B, a periodic array of vertically-oriented nanocoaxes may be fabricated with $10^6$ units in a 1 $mm^2$ area. Each unit may include a nanoscale coaxial cable whose coax annulus is filled with a nanoporous insulator, $Al_2O_3$. Target molecules entering this annulus (e.g. via chemical adsorption) may cause a change in the dielectric response (capacitance and conductance) in proportion to their number and dielectric properties. The well-defined structure and physical dimensions may lead to a multiplicative effect of each unit's functionality in measurements of the chip as a whole. A high throughput, multiplexed chip may be devised by micropatterning electrodes with consistent performance in the subdivided array. Arrays may be further physically stabilized by embedding them in a supporting epoxy. The nanoscale spacing between the coax inner and outer conductors may enhance the device's response to the introduction of trace amounts of analyte, such that high sensitivity may be expected. To determine the porosity of the coax annulus medium, a sputter-deposited $Al_2O_3$ coating may be prepared on a vertically aligned carbon nanotube (CNT) array. The porosity may be tested electrochemically by polypyrrole filling, and may produce estimated results of about 10%. A high resolution transmission electron microscopy shows a pore size in this alumina layer that may be smaller than 10 nm, which may be categorized as mesoporous.

Referring now to FIGS. 20A-C, results of humidity detection of an embodiment of the nanocoaxial sensor array discussed herein is illustrated. In FIG. 20A, Nyquist plots of impedance spectroscopy from 10 mHz to 1 MHz for dry (red) and water-immersed (blue) sensor are presented. FIG. 20B presents a capacitance extracted from data shown in FIG. 20A. Light gray symbols refer to the capacitance measurement by lock-in amplifier showing consistency with that extracted from spectroscopy by potentiostat (see SI). FIG. 20C illustrates an inset, a capacitance response vs. time for various levels of relative humidity RH, measured with a capacitance bridge and lock-in amplifier, at 10 Hz and 0.1 $V_{rms}$; (main panel) Delta C at 1,000 s vs. RH, showing power-law response across 3 decades in RH.

Using such a nanocoaxial array, dielectric spectroscopy may be employed to detect and identify target molecules entering the coax annuli. Such spectroscopy may be conducted by scanning frequency from 10 mHz to 1 MHz, and measuring the real and imaginary components of the electrical impedance. As shown in the resulting Nyquist plot of FIG. 20A, the empty or "dry" signal, conducted in air with relative humidity (RH)=25%, showed high intrinsic impedance dominated by capacitance. The presence of water may decrease this impedance by increasing both the device conductance and capacitance. At frequencies below 10 Hz, the data may be suggestive of frequency dispersion, attributed to polarization on electrode surfaces. The capacitance between 10 Hz and 30 kHz remained stable, as shown by FIG. 20B. It may be noted that moisture under the experimental conditions employed may be absorbed to the $Al_2O_3$ layer to form a thin water film. The accumulation of hydronium and hydroxide ions in a double layer on electrodes may determine the polarization characteristics. The influx of ion species may vary linearly with ion mobility and with concentration and electric potential gradients. Tangential ionic diffusion due to electrode roughness and media porosity, introducing non-uniform electric fields, could be involved as a dominant process in the spatially-confined water film. Corresponding to a reduced mobility, the establishment of equilibrium will be a slow process, such that dispersion caused by double layer capacitance may be observed only at very low frequency. In order to avoid this effect in the dielectric detection of chemicals, all subsequent recordings may be performed at 10 Hz. As shown in FIG. 20B, the addition of water may increase the capacitance at 10 Hz from 1.0 to 2.3 nF, due to a change in the net dielectric constant as the dielectric constant of water is about 80. As calculated in SI, the dielectric constants of empty (AlO+air) and water-filled (AlO+water) porous alumina/$Al_2O_3$ corresponded to 5.5 and 10.35, respectively. Thus, the calculated capacitances of the sensor array, in air and submerged in water, are 1.1 and 2.1 nF, respectively, in good agreement with the above measured values.

The adsorption-based sensing capability of the nanocoaxial array may be next examined as an RH sensor, with the result that water vapor diluted in $N_2$ gas increased the capacitance with a monotonic concentration dependence. An embodiment of a raw data for changes in capacitance, delta C (i.e. after subtracting the $N_2$-only capacitance value) vs. time for a set of RH values are shown in FIG. 20C (inset), due to the introduction vapor+$N_2$ at 1 bar (note, the phrase delta C and $\Delta C$ are used interchangeably throughout). Delta C values may be selected at t=1,500 s (inset dotted line) to characterize the response, as summarized in the main panel of the figure. Here, it may be seen that a power law dependence over 3 decades of RH emerges, delta C~$RH^\beta$, with $\beta$~0.85. The right scale indicates the corresponding fractional change in capacitance. With moderate improvements in signal-to-noise ratio, it may be anticipated that such measurements may be extended to the 0.01% RH range and below.

In some embodiments of this sensor's design, moisture adsorption may starts from the open end of the nanocoaxial unit, followed by diffusion into the deeper pores of the alumina layer. At 100% RH, a water "soaking depth" delta l may be estimated to be approximately 0.8 $\mu m$, based on the expression for a coaxial capacitor (SI), $\Delta l = \Delta C \ln(r_2/r_1)/(2\pi N \epsilon_0 (\epsilon_{AlO+air} - \epsilon_{AlO+water}))$. In this expression, t is the thickness of the coax annulus, $r_1$ the radius of the inner conductor, $r_2 = r_1 + t$ the inner radius of the outer conductor, $\Delta C$, also referred to as delta C, is the change of capacitance due to introduction of water into the porous annulus, N the number of nanocoaxial units functioning in parallel, $\epsilon_o$ the permittivity of air. Since all units are 1.5 $\mu m$ in height, the capacitance of any planar component at the bottom of chip may be considered to not participate in the response to moisture adsorption. The exceptional response across the full scale between 0 and 100% RH may be ascribed in part to the above relationship between $\Delta l$, also referred to as delta l, and $\Delta C$, also referred to as delta C, of the coaxial structure, as well as the additive effect of the N capacitors in parallel. The sublinear behavior ($\beta$<1) may be associated with the finite dissipation in the circuit, where β may also be referred to as beta. More remarkable is the extraordinary sensitivity that is also afforded within the large dynamic range. The lowest RH employed may be 0.1% (equivalent to 16 ppm at 20° C.). This result may be lower than the limit of detection of all extant alumina based humidity sensors. It also suggests that the pore size of the sputtered alumina may be smaller than that revealed by transmission electron microscopy (TEM), since the Kelvin radius ($r_k$) that dominates the capillary condensation is of subnanometer size at the given humidity. On the hand, ultrasmall pore sizes largely reduce Knudsen Fickian diffusivities of chemical molecules in porous alumina, leading to slower response rates.

Referring now to FIGS. 21A-D, results of an embodiment of a nanocoaxial sensor array for chemical detection are illustrated. FIG. 21A illustrates concentrations of methanol vapor in $N_2$ gas introduced (at t=0) increase capacitance over time. Capacitance at 100 s is marked with arrows. FIG. 21B illustrates a sensor response versus methanol concentration. The recordings illustrated show three separate readings (open circles) taken on different days. Each value is illustrated as taken at 100 s after the methanol application. The averages (solid circle) are illustrated as fitted by two isotherm expressions. FIG. 21C illustrates ethanol detection limit. The capacitive response (averaged over three independent measurements) at 0, 0.15 ppb and 0.60 ppb concentrations is shown and fitted. The quantities $\Delta C_\infty$ and $\delta(\Delta C)$ may be defined. FIG. 21D illustrates a summary of ethanol response, showing power-law behavior over almost 5 decades, and sub-ppb sensitivity. High (triangles) and low (squares) concentration regimes present readings investigated on separate days, with the latter repeated three times and resulting averages and standard deviations plotted. All data may be recorded by capacitance bridge and lock-in amplifier at 10 Hz.

The nanocoaxial sensor described herein may be used to detect a series of VOCs, including methanol, ethanol, 1-propanol, acetone, hexane, and cyclohexane, using gases commercially-prepared at ~3 ppm in $N_2$. Lower concentrations may be obtained by diluting individual gases in $N_2$ carrying gas at controlled flow rates. The general protocol to conduct measurements may include procedures for sensor initiation by evacuating the sample chamber, chemical gas injection to bring the chamber pressure to 1 bar, and recording the 1 bar capacitance response versus time in an enclosed environment without active flow. Capacitance recordings may show responses similar to the RH data above. To characterize the response, the change in capacitance of 100 s after the introduction of target gas to the chamber may be chosen. Also delta C may be chosen to be C(100 s)−C(0 s), as shown in FIG. 21A results for various concentrations of methanol in $N_2$. In these VOC experiments, the introduction of 1 bar of $N_2$ gas by itself may increase the capacitance by 2.2±0.1 pF (0 ppb line in FIG. 21A). Subtracting this value may yield a net response $\delta(\Delta C)$. FIG. 21B may show the resulting data vs. methanol concentration. These data may be fit with isotherms based on phenomenological models typically used to characterize adsorption in porous media. For example, Langmuir molecular adsorption may predict a variation with concentration c of ac/(b+c), where a and b are constants, while both Langmuir dissociative adsorption and Freundlich adsorption may vary as $\sim c^{1/2}$. Alcohols such as methanol, ethanol and 1-propanol, as well as acetone, may be better fit with the $c^{1/2}$ expression, while, for hexane and cyclohexane, the ac/(b+c) expression provided may provide a better fit. To confirm the adsorption basis for the detection, a control chip may be also prepared, by filling the annulus with nonporous $Al_2O_3$ (via atomic layer deposition, ALD) and etching to develop a cavity with comparable volume to the porous space in a regular sensor. Methanol at 2.5 ppm $N_2$ may show a 2.6±0.07 pF response in this control, about 100× lower response compared to the standard nanoporous chip, which may be as anticipated.

Referring now to data illustrated by FIG. 21C, illustrating data acquired where ethanol may be diluted to sub-ppb levels. The capacitance response for two such concentrations is expressed along with the undiluted $N_2$ response. Rather than choose a particular time to define the response, the data may be fit with the standard expression for a charging capacitor, $\Delta C(t) = \Delta C_\infty(1-e^{-t/\tau})$, where $\Delta C_\infty$ is the steady state amplitude (i.e., as t→∞), and τ is a time constant, and used $\Delta C_\infty$ as the figure of merit. From 0.15 to 6.0 ppb, $\Delta C_\infty$ increased from 3.0±0.1 pF to 4.5±0.3 pF, with τ~90 s for both. Subtraction of the background $N_2$ signal (shown only by its fit in FIG. 21C) yields the quantity $\delta(\Delta C)$ due to ethanol alone. An accumulation of all the data for ethanol is shown in FIG. 21D on logarithmic scales. Similar to the RH data, a power-law response to concentration c may be observed, with $\delta(\Delta C) \sim c^\alpha$ and α~0.46, now extending across nearly 5 orders of magnitude, to the ~100 ppt (parts-per-trillion) level. This exponent is close to that expected from a Freundlich isotherm, α=½, as plotted in the figure. For the 0.15 ppb ethanol data, it may be calculated that each nanocoax unit may detects a signal produced by only ~30 ethanol molecules (see SI). Such sensitivity for VOC detection may not have been yet reported for any alumina-based chemical sensor, or for any chemical sensor for the detection of ethanol. These results may show a sub-ppb detection for all VOCs.

Figure 30:
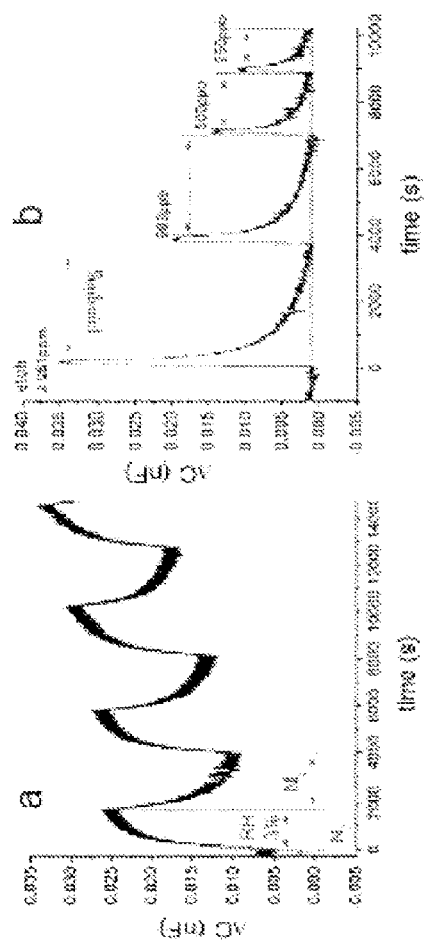
FIG. 30 shows sensor response to relative humidity (RH) and ethanol. Panel a: Sensor was treated with humidified $N_2$ gas at RH=3% and flushed with $N_2$ gas four times. Panel b: Response to a series of ethanol concentrations. The ethanol vapor carried by $N_2$ gas is applied to the sensor after evacuation with pumping. The recovery (desorption) takes tens of times longer than the rising (adsorption) phase.

As water has higher polarity than any of the aforementioned solvents, its equilibrium isotherm may also exhibit power-law behavior, consistent with the Freundlich isotherm. This may suggest that polar protic solvents may undergo multilayer adsorption, even condensation, on the surfaces of the sensor structure, as opposed to non-polar molecules, which may appear to saturate with limited adsorption sites due to monolayer formation. The fitting parameters of the solvent isotherms may be summarized in a table. The values of delta C corresponding to the chemicals at their highest concentrations may exhibit correlations to their relative dielectric constants $\epsilon_k$, which may agree with the detection mechanism addressed for humidity sensing. Delta C's were also observed to correlate with $r_k$, molecular weight and the maximum distance between atoms of each kind of molecule (FIG. 30), which could be connected to both diffusion and condensation of VOCs.

Referring now to FIG. 22A-B, an embodiment of impedance spectroscopy of VOCs for the nanocoaxial sensor array is illustrated. FIG. 22A illustrates a spectra of impedance phases for water, ethanol and hexane, as measured by scanning the signal from 10 mHz to 1 MHz. Three binned segments of the spectra are denoted G-band (1.0 to 1.5 Hz), B-band (50 to 100 Hz), and R-band (200 to 400 kHz). FIG. 22B illustrates the readings for the green band (G-band), blue band (B-band) and red band (R-band). An 8-bit brightness scheme (from 0 to 255) may be used to represent the designated range of phases. After reading phases of all chemicals at indicated frequencies (denoted by arrows), the phases may be converted to brightness of the corresponding color according to the following function:

$$\text{Brightness} = 255 \times (\text{phase}_{max} - \text{phase})/(\text{phase}_{max} - \text{phase}_{min})$$

The color code may be written as (G-band, B-band, R-band). Accordingly, the color for each chemical may be computer composed and shown as its legend box color, while the error bars in the spectra may represent standard mean errors for n=3 measurements.

Spectroscopic methods may exhibit a substantial power for analytical identification via impedance spectroscopy, for example, demonstrating potential for molecular detection. Notably, spectroscopic signatures of targets based on their intrinsic dipolar relaxation may be used to identify molecules more directly. The architectural advantages and outstanding sensitivity of the present nanocoaxial array may suggest its potential utility in nanospectroscopy. The device's ability to capture trace amount of molecules, read out polarization information at the nanoscale, and simultaneously superimpose the signal of millions of units with drastically enhanced signal-to-noise ratio are a few of the perceived innovative features. Using the same setup and procedure for the experiments of FIG. 20A, the magnitude and phase of the impedance spectra of chemicals may be obtained with the nanocoax sensor between 10 mHz and 1 MHz, as shown by data illustrated in FIG. 22A. The phase response provided more discrimination among various VOC species than did the magnitude. Highly reproducible recordings from various chemicals were then compared in subdivided frequency regimes, as shown in FIG. 22B.

In order to discriminate the chemicals and identify them, colorimetric identification may be employed to visualize the results. Frequency bins of 1.0 to 1.5 Hz, 50 to 100 Hz, and 200 to 400 kHz may be assigned green (G-band), blue (B-band) and red (R-band) colors. Each chemical may be represented by a unique color within an 8-bit scheme for each band. As shown in FIG. 22B, the color codes for the tested chemicals corresponding to the indicated frequencies (in Hz) are: methanol (228, 203, 144), ethanol (125, 90, 224), 1-propanol (142, 53, 192), and hexane (32, 19, 169). Accordingly, the representative color sets of the chemicals may be indexed by computer.

Accordingly, the present nanocoaxial structure may be used as a nanospectroscopic device to discriminate chemicals. It may enrich the family of chemical detectors as a promising new member for VOC detection. Comparing to detection with electronic nose devices that had cross-reactivity and inconsistency between chemiresistor units, the present nanospectroscopy technique may be considered superior with respect to explicit differences of the spectra and colorometric reading, as well as the obvious potential for portability.

Note that, although a number of electrical detection techniques (e.g., impedance spectroscopy) are described herein, other detection techniques may be used in addition or alternative to electrical detection. For example, optical techniques known in the art, such as optical spectroscopic detection may be used.

In summary, ordered nanocoaxial sensor arrays as described herein may achieve quasi-molecular level sensitive, and multimodal on-chip nano-spectroscopic, detection of a broad class of chemical compounds. These results may demonstrate a fusion platform affording the ultrasensitive quantization and potential identification of chemicals. This work may emphasize the combination of nanomaterials and nanocoaxial structures, with a derived high-throughput and multimodal functionality that may help to minimize false positives and negatives in the detection of various chemical and biological entities.

EXAMPLES

In some embodiments, nanosensors described herein may be produced using materials and methods listed below. The section below provides some non-limiting examples which may be used in combination with any other examples, features or embodiments comprised herein to produce a nanosensor device.

1.1. Equipment and Chemicals

Aligner (MA6/BA6, SUSS MicroTec);
Sputtering evaporator (PVD 75, Kurt J. Lesker Comapany);
Electron beam evaporator (PVD 75, Kurt J. Lesker Comapany);
Atomic layer deposition (Cambridge Nanotech);
Vibrome 2 Polisher (Buehler);
SM-31160 Scanning electron microscope (JEOL);
Gamry Reference 600 (Gamry Instruments);
Vacuum oven (Lindberg Blue M);
Model SR830 DSP Lockin amplifier (Stanford research system);
Rotameters Model 7263, accuracy ±4% (Dwyer.com);
Mass Flow Controller and readout, accuracy ±0.1% (MKS);
Metal targets (metal targets Ti and Al, purity 99.99%, Kurt J. Lesker Company);
S1813, Photoresist (Rohm and Haas electronic materials LLC);
MF 319 Photoresist developer (Rohm and Haas electronic materials LLC);
Polystyrene sphere Sulfate latex 8% w/v 1.4 m (Invitrogen/Molecular Probes);
Alumina etchant (Transene Company, Inc.);
Tetrahydrofuran T 397-4 (Fisher Scientific);
Atomic layer deposition precursor trimethylaluminum (Sigma-Aldrich);
Polishing slurry, Masterprep Suspension 0.05 µm (Buehler);
Analytical gases: methanol 2.53 ppm; ethanol 2.95 ppm; Hexane 2.96 ppm;
Cyclohexane 2.97 ppm; n-propanol 2.64 ppm; acetone 3.00 ppm; mixture with high purity nitrogen, with the analytical uncertainty of ±5% (Airgas);
HPLC grade water (Sigma-Aldrich);
Gases (ultrahigh purity nitrogen gas, Airgas.com).

1.2. Preparation of Periodic Carbon Nanotube Arrays

Figure 23:
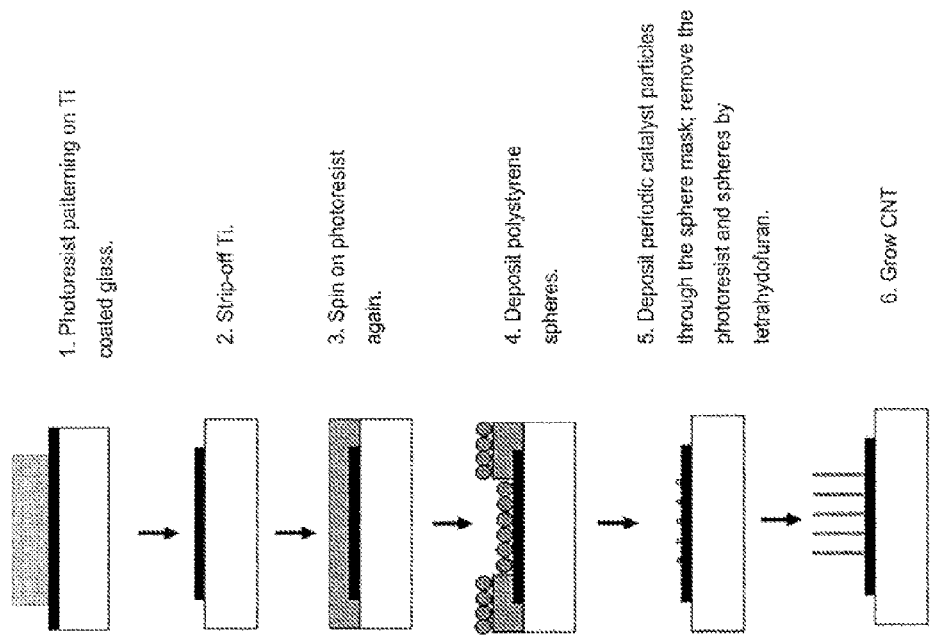
FIG. 23 is a schematic showing growth of a periodic CNT array.

Periodic carbon nanotube (CNT) arrays were prepared. As show in FIG. 23, Shipley 1813 photoresist was patterned by photolithography and used to strip-off Ti. The Ti strip was used as Electrode1 to grow CNTs. A second photoresist coating (Shipley 1818) was applied by spin-coating, with 1×1 $mm^2$ windows opened to expose the Ti strips underneath. The Ti thickness was 100 nm. UV ozone descumming was used to clean the Ti surface in the window. A monolayer of 1.4 µm diameter polystyrene microspheres was deposited to form a mask for E-beam evaporation of Ni (60 nm). Upon removal of the photoresist and sphere layers with tetrahydrofuran (THF) and sonication, a periodic array of Ni dots was revealed on the Ti electrode. These were used to catalyze CNT growth. The site density determined by the sphere monolayer corresponded to $10^8/cm^2$. At the beginning of CNT growth, the Ni dots were annealed and plasma etched at 550° C. for 2 min. CNTs were vertically grown by supplying $NH_3$ at 160 sccm and $C_2H_2$ at 80 sccm with plasma and 650-700° C. for 15-20 min. The CNTs were approximately 1.5-2.0 µm in length and 150 nm in diameter.

1.3. Fabrication of CNT-Based Nanocoaxial Cavity Arrays

Figure 24:
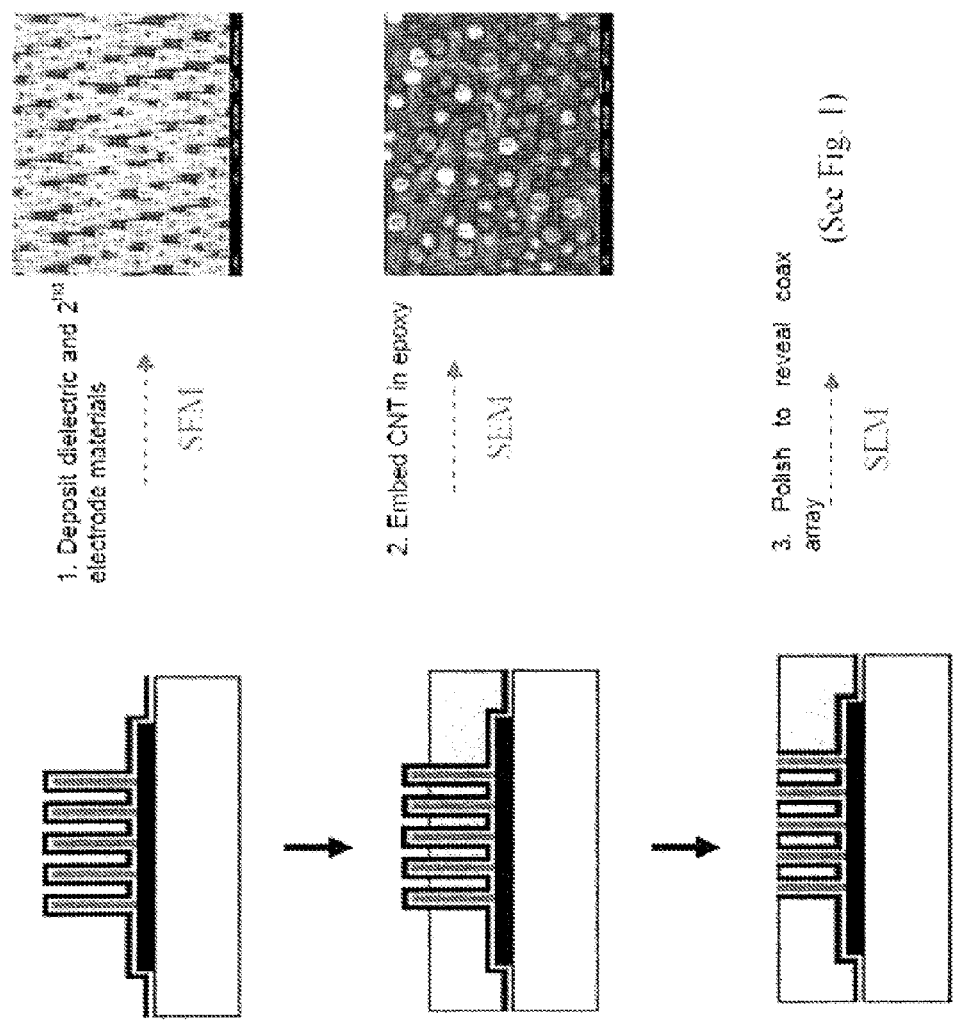
FIG. 24 a schematic showing fabrication of a nanosensor array.

To fabricate the coaxial structure, $Al_2O_3$ and Al layers were successively deposited on the CNT array. As shown in FIG. 24, an initial coating outside of the CNT of 10 nm $Al_2O_3$ was deposited by atomic layer deposition (ALD) to prevent potential shortages between the inner and outer coax electrodes; deposition was carried out at 200° C. in 100 cycles. Following ALD, reactive sputtering was employed to apply 90-100 nm porous $Al_2O_3$ by introducing $O_2$ with 1:4 ratio to argon during Al sputter deposition.

Deposition rate was calibrated at 0.4 Å/s, and thickness determined by a Sigma SQM-160 monitor. The final layer of the coax structure was 250 nm-thickness Al (corresponding to Electrode 2), sputter deposited through a mask. Electrodes 1 and 2 overlapped at the 1×1 $mm^2$ window that contained the coax array. In order to stabilize the chip structure and electrical properties, an annealing was performed for 8 hr between 150-200° C. in a vacuum oven. The DC resistance between Electrodes 1 and 2 was nominally in the giga-ohm range. The coax arrays were then embedded in SU8-2002 photoresist by spin-coating. After being soft baked at 100° C. for 5 min, SU8 was exposed to UV light for 3 min, then hard-baked at 150° C. overnight. Finally, the coax array was polished with a vibratory polisher at a power level of 80% for 4-6 hr until approximately 95% of the nanocoax structures were exposed (as visualized in a top-view of SEM). Of note, for nanocavity formation only nonporous $Al_2O_3$ was deposited. A wet etchant was then applied to the chip for 12 hr at room temperature, resulting in 200-300 nm vertical etching of the dielectric $Al_2O_3$. Note that Electrode 2, which is the external conductor of the nanocoax structure, corresponded to Ti.

1.4. Focused Ion Beam Milling

TEM samples were prepared using the in-situ liftout (INLO) technique. The bulk sample containing the embedded nanocoax structures was placed in a JEOL JSM 4500 multibeam instrument and tilted to 52° such that the sample surface was normal to the focused ion beam column. A protective 15 μm (length)×3 μm (width) tungsten strap was first deposited on the sample surface using the focused ion beam (FIB) and tungsten hexacarbonyl as precursor gas. Initial rough cuts, 15 μm wide, 12 μm long and approximately 10 μm deep were milled into the sample on either side of the tungsten deposit using a beam current of 5.3 nA. The area was then further thinned at a beam current of 277 pA until the thickness of the tungsten strap was approximately 1 μm. The sample was then tilted to 0° such that the FIB impinged on the sample at a 38° angle of incidence. A "U" cut was then milled through the membrane, perforating the membrane along the bottom and up either side, leaving a small amount intact on top of the sides in order to secure the sample to the bulk. A Kleindiek MM3A micromanipulator was used to locate a tungsten probe into contact with the top of the tungsten deposit and welded to the membrane using FIB W deposition. The remaining portion of the sample, fixed to the bulk, was then cut free and the free-standing sample removed and transferred to an Omniprobe grid and affixed to one of the posts using FIB W deposition once again. The sample was then tilted back to 52° (normal incidence to the FIB) and thinned to a final thickness of approximately 100 nm using a beam current of 30 pA.

1.5. Electrochemistry to Characterize Electrical Properties and Porosity of $Al_2O_3$ Thin Film Electropolymerization of polypyrrole (PPy) was used to characterize the integrity of an $Al_2O_3$ film and measure its porosity. To demonstrate the difference of $Al_2O_3$ coatings by sputter deposition and ALD, the $Al_2O_3$-coated CNT arrays were subject to electropolymerization by connecting the Ti strip as the working electrode in a three-electrode system. A platinum wire served as counter electrode and AgCl coated Ag foil was used as a reference electrode. The buffer contained 0.5 M pyrrole and 0.1 M NaCl. Cyclic voltammetry (CV) was performed with the voltage scanned from 0 to 0.9 V at 100 mV/s for 10 cycles.

Figure 25:
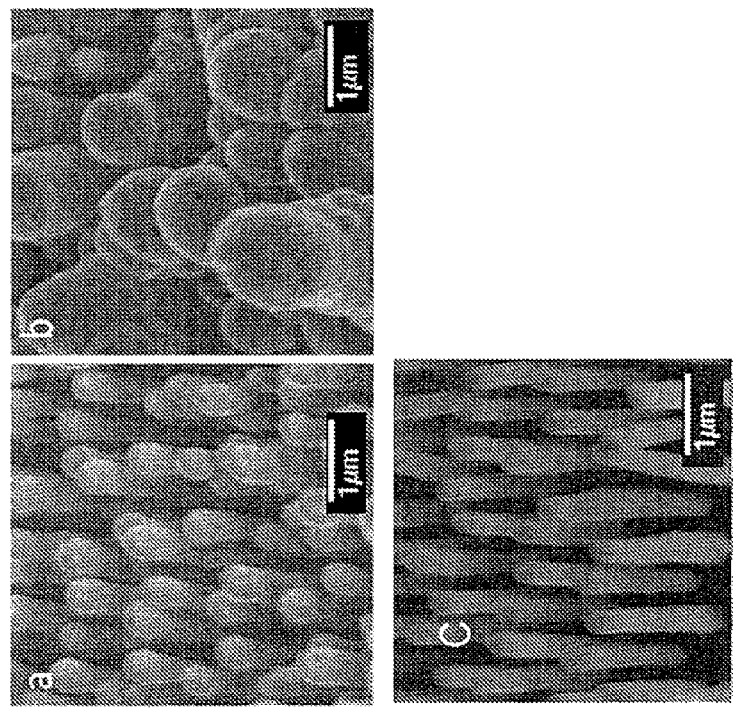
FIG. 25 shows Electropolymerization of PPy on $Al_2O_3$-coated CNT arrays. For $Al_2O_3$ from sputter deposition, (a) and (b) correspond to the SEM images before and after PPy electropolymerization, respectively. No apparent PPy deposition was shown on the ALD $Al_2O_3$ (80 nm) coated CNT array (c).

Basically, the porous structure can generate leakage in the $Al_2O_3$ film. In a liquid environment for PPy electropolymerization, electrolytes and pyrrole monomers can diffuse into the film and support electrochemical reactions at the CNT surface, provided an oxidative voltage is applied. Because PPy is a conductive polymer, polymerization will proceed in the pore structures and continue outside the film after the pores are filled in the sputter deposited $Al_2O_3$ (FIGS. 25 a and b). In contrast, when the CNT array was coated by ALD $Al_2O_3$, the surface was completely insulated by the compact coating and no PPy deposition could be observed (FIG. 25 c).

Figure 26:
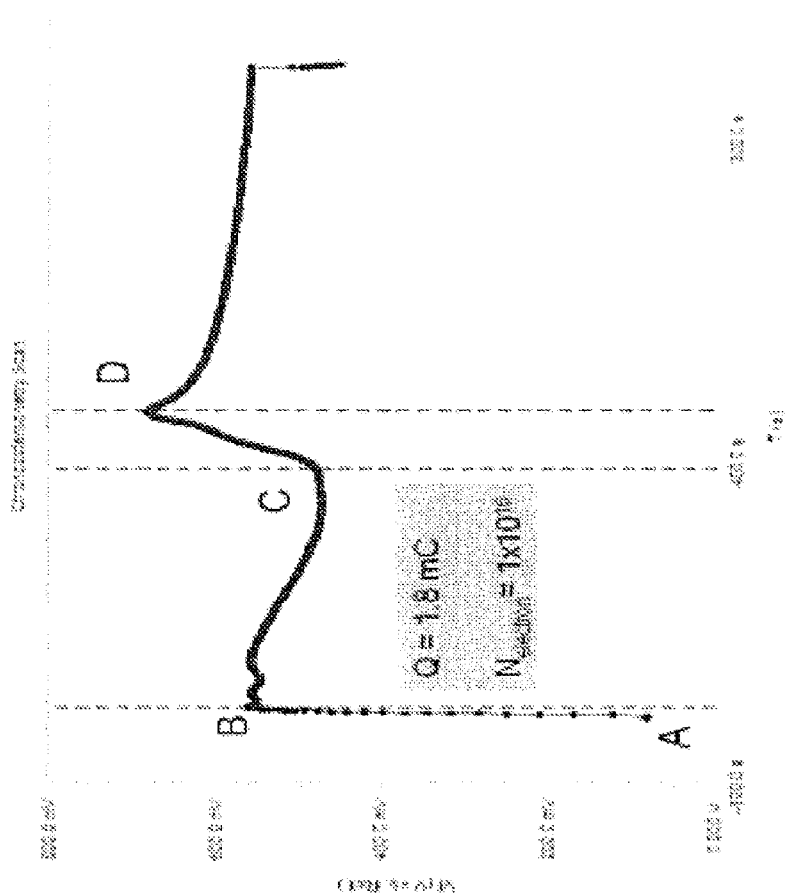
FIG. 26 is a plot showing the phases of galvanostatic deposition of PPy in porous $Al_2O_3$ thin film. a-b: PPy nucleated at the pore bottom of $Al_2O_3$; b-c: PPy grew inside the pores; c-d: the transition phase; d: PPy deposited outside the $Al_2O_3$ coating.

To determine the porosity, galvanostatic deposition of PPy was conducted on a Ti-metalized glass with sputtered $Al_2O_3$ film. A constant 5 μA current was applied to the sample in the same buffer mentioned above. The potential vs. time was recorded as an indication of different deposition phases by which the amount of PPy filling into the pores was determined (FIG. 26).

The potential recorded during the galvanostatic deposition indicated multiple phases of the reaction. A-B: PPy nucleated at the pore bottom of $Al_2O_3$; B-C: PPy grew inside the pores; D-C: the transition phase; D: PPy deposited outside the $Al_2O_3$ coating (FIG. 26).

The total charge of PPy filling into the porous cavities during phase BC can be converted to volume of PPy, also volume of porous cavities $V_{cav}$ according to:

$$V_{PPy} = V_{cav} = \frac{m \cdot Q_{PPy}}{F \cdot \sigma}$$

where m is the molecular weight of pyrrole, $Q_{PPy}$ the total charge from PPy filling into the porous cavities. F the Faradic constant and σ the density of pyrrole, equal to 1 $mg/mm^3$.

The percentage porosity (φ) can then be calculated by:

$$\phi = \frac{V_{cav}}{V_{Al_2O_3}} \times 100$$

where $V_{Al2O3}$ is the volume of $Al_2O_3$ calculated based on the thickness of $Al_2O_3$ coating.

According to FIG. 26, φ was 10% for sputter-deposited $Al_2O_3$ coating.

1.6. Spectroscopic Measurements with Gamry Reference 600 Potentiostat

A polypropylene o-ring was attached to the center area encircling the nanocoax array in order to contain the test liquid. A two-electrode electrochemical system was configured by using the top Al film (Electrode 1) as the combined reference and counter electrodes, and the Ti film (Electrode 2) as the working electrode. An AC sine-wave voltage (10 mV peak-to-peak) was applied to the coax chip. The maximum frequency range was from 0.01 Hz to 1 MHz with 20 impedance readings per decade. The impedance data were analyzed using Echem Analysis software (Gamry, Inc.). Note, before loading the sample, the sensor chips were thoroughly dried under vacuum oven at 90° C. for 1 hr.

1.7. Capacitance Measurements with Lock-in Amplifier (LIA) for Humidity and Chemical Detection Measurements were conducted in a recording chamber. The chamber is air-tight with valves for gas inlet, pumping, and exhaust. A pin socket provided the electrical connections from the LIA to the sensor electrodes and shielding chassis.

Figure 27:
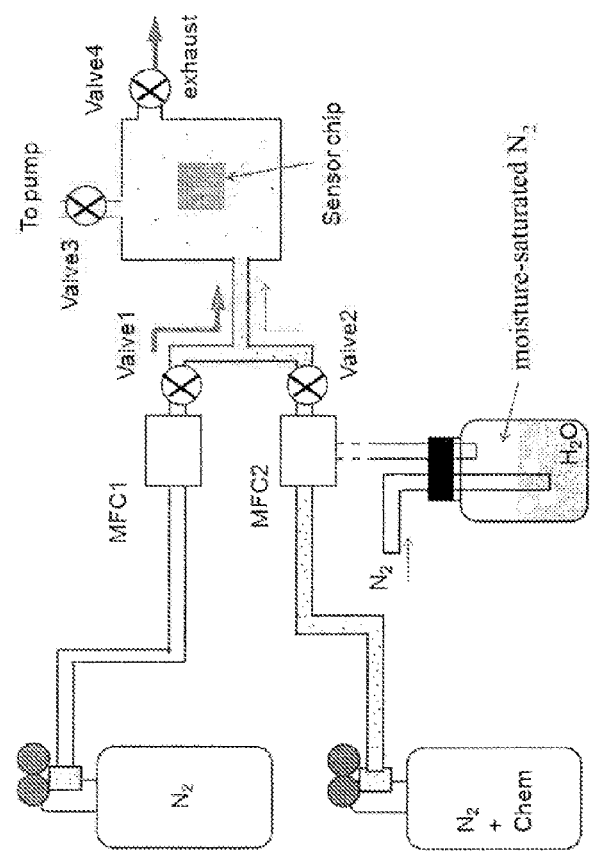
FIG. 27 is a schematic of a gas dilution and control system.

To measure the capacitance, Stanford Research Model 830 LIA was set as follows: voltage 0.100 V; frequency 10 Hz; time constant: 3 s; and sensitivity 10 µV full scale. A gas dilution system was constructed and used to control the concentrations of humidity and chemical vapors (FIG. 27). For humidity measurements, moisture-saturated $N_2$ from a bubbling bottle was diluted by ultra high purity $N_2$ according to the ratio of their flow rates. For VOCs, stock gasses were diluted by ultra high purity $N_2$. The concentrations were determined by the flow rate ratio of the chemical gas and the dilutant $N_2$ gas controlled by mass flow controller. The purity and concentration of each gas was manufacture-certified based on gas chromatography. For all measurements, the gases were introduced into the chamber at 5000 SCCM total flow rate.

The measurement procedure was as follows:
1. All electrical and pneumatic connections are established, close chamber, and pump down the system until the capacitance stabilizes. Here, the vacuum level corresponds to 8 mTorr.
2. Balance the LIA with a high precision capacitance bridge (General Radio Model 1616) and zero the capacitance and conductance display.
3. Purge and pump the chamber three times with $N_2$.
4. Introduce mixtures of the chemical gas and $N_2$ at different ratios to supply at the designated concentrations.
5. Stop flow and maintain the pressure at 1 bar during data recording.

2. Other Results 2.1. Dielectric and Capacitance Calculations

Given the dielectric constant of nonporous alumina ($\varepsilon_{AlO}$=9.3), and porosity ($\phi$=0.1), the dielectric constant of porous alumina can be calculated to be $\varepsilon_{ALO+-air}$=5.5, according to:

$$\varepsilon_{ALO+air} = \frac{3\varepsilon_0 - (\varepsilon_0 - 4)\phi}{3 + (2\varepsilon_0 + 1)\phi}$$

Typically, the nanotube diameter ($2r_1$) was 150 nm, and the alumina thickness (t) was 100 nm. The radius of the outer conductor was $r_2=r_1+t$. Based on electron microscopic information, the length (l) of a nanocoax was 1.5 µm. The basal capacitance of the sensor chip ($C_0$) was 1.1 nF given by:

$$C_0 = \frac{2\pi\varepsilon_0\varepsilon_{ALO+air} \cdot l \cdot N}{\ln\left(\frac{r_2}{r_1}\right)}$$

When the porous spaces were filled with water, the equivalent dielectric constant ($\varepsilon_{ALO-water}$) of the alumina film became 10.35, following the Clausius-Mossotti equation:

$$\frac{\varepsilon_{ALO+water} - 1}{\varepsilon_{ALO+water} + 2} = \phi \cdot \frac{\varepsilon_{water} - 1}{\varepsilon_{water} + 2} + (1 - \phi) \cdot \frac{\varepsilon_{ALO} - 1}{\varepsilon_{ALO} + 2}$$

where $\varepsilon_{water}$ is the water dielectric constant (~80). Due to the change of dielectric constant, the capacitance of the chip became 2.1 nF, close to the 2.3 nF measurement discussed in the text.

2.2. Detection Sensitivity Calculation

This calculation estimates the minimum amount of chemical molecules that can be detected by the nanocoax sensor. The parameters for the calculations may include: $V_{mol}$, the molar volume of ideal gas at 25° C., corresponding to 24.465 L/mol; $V_{cham}$, the volume of the measurement chamber approximates 0.2 L; $S_{cham}$, the internal surface area of the chamber and corresponds to $2\times10^4$ mm$^2$; N, the total number of nanocoax units, approximately $1\times10^6$; $S_{array}$, the adsorption area of the sensor chip, designed to be 1 mm$^2$; [EtOH]$_{min}$, the minimum detectable ethanol concentration, 150 ppt; and $A_0$, Avogadro's constant, $6.023\times10^{23}$ molecules/mole.

At 1 bar, the amount of ethanol molecules $N_{EtOH}$ in the chamber is calculated by:

$$N_{EtOH} = \frac{V_{cham}}{V_{mol}} \cdot A_0 \cdot [\text{EtOH}]_{min}$$

Assuming all ethanol molecules were adsorbed to the surfaces, the amount of molecules captured by the sensor $N_{chip}$ is:

$$N_{chip} = N_{EtOH} \cdot \frac{S_{array}}{S_{cham}}$$

So the amount of ethanol molecules detected by each nanocoax, $N_{coax}$, is:

$$N_{coax} = \frac{N_{chip}}{N} \approx 33$$

Figure 28:
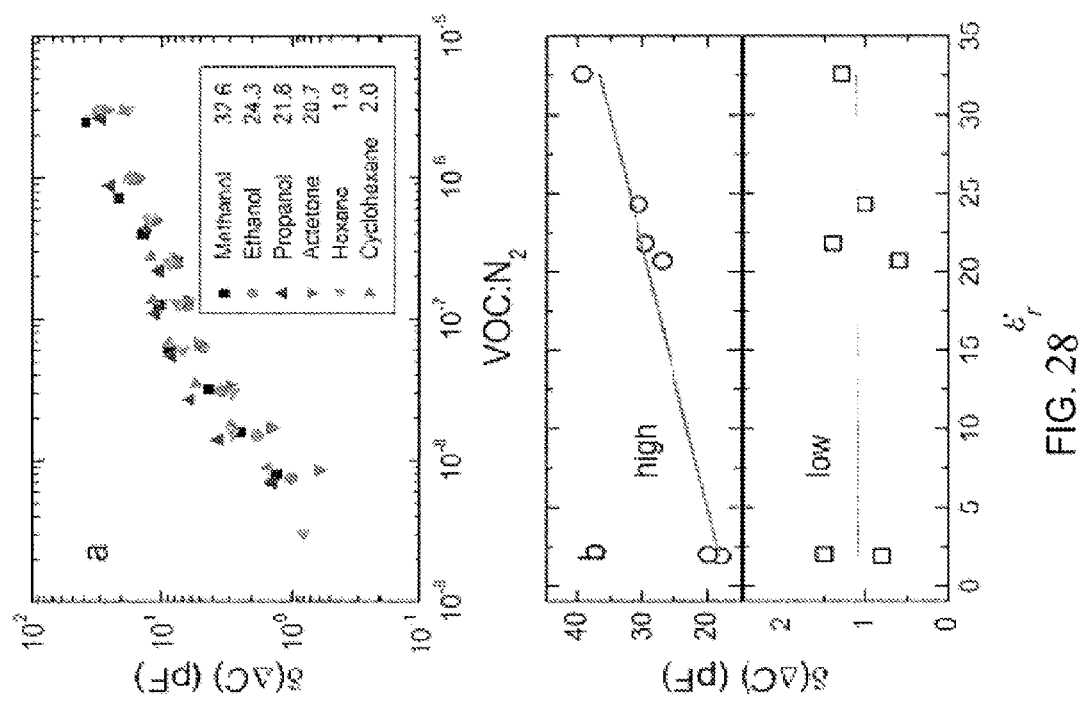
FIG. 28 shows the results of volatile organic compound (VOC) detection by the nanocoaxial sensor array. Top Panel: Concentration dependent responses of various VOC species. Numbers in the figure legends are the values of $\in_r$ of the chemicals. Bottom Panel Relationship between sensor response to VOC and $\in_r$. The sensor responses at 8 ppb ($\Delta C_{low}$) and 3 ppm ($\Delta C_{high}$) are plotted vs. respective $\in r$ values. Lines shown are linear fits.

The sensor was used to detect a variety of other VOCs, including ethanol, methanol, propanol, acetone, hexane, and cyclohexane, with results for concentrations in the ppb and ppm ranges (FIG. 28 a). It is noteworthy that at higher concentrations, the response was nominally linear with respect to relative dielectric constant $\varepsilon_r$, while at low concentration, such a correlation was absent (FIG. 28 b). The mechanism underlying signal transduction of this nanocoaxial capacitor at extremely low chemical concentrations nay be that when the molecule is polar, condensation readily occurs in the $Al_2O_3$ pores, such that at high concentration, molecules with high dipole moment, i.e. high $\varepsilon_r$, tend to form multiple layers, with weakly bound outer layers that are thus free to respond to the oscillating electric field. At low concentrations, monolayer formation of absorbed molecules inhibits such free dielectric response. This could play a role in the weak $\varepsilon$ dependence at low concentration.

Figure 29:
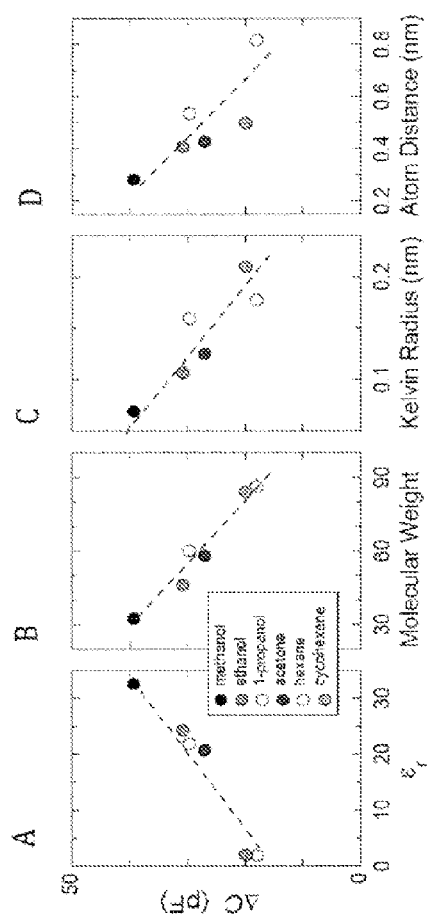
FIG. 29 shows capacitance responses to 3 ppm VOCs vs. dielectric constant (A), molecular weight (B), Kelvin radius (C), and maximum atom distance (D).

FIG. 29 shows capacitance responses to 3 ppm VOCs vs. dielectric constant (A), molecular weight (B), Kelvin radius (C), and maximum atom distance (D). Chemical dielectric constants, surface tension, saturation vapor pressure were obtained from *Handbook of Chemistry and Physics*, CRC Press; maximum atom distances of chemical molecules were obtained from National Institute of Standards and Technology.

Rising and Recovery Phase in Humidity and Ethanol Detection

The following figures show the time dependent sensor response to 3% RH under the dynamic detection process (FIG. 30a), as well to a series of ethanol concentrations under the static detection process (FIG. 30b). The static detection process shows much more rapid response to the range of concentration introductions than does the dynamic process performed at 3% RH. In terms of the sensor recovery, the dynamic detection process used for 3% RH was operated under constant $N_2$ flow. It is noted here that the complete recovery was not necessary to ensure the good repeatability of its response to certain RH levels. For the recovering phase in static process in ethanol detection, one can initiate a sensor by vacuum pumping to ensure consistent measurements for deferent concentrations, although $N_2$ flow might help to reduce recovery time.

Comparison of Sensor Responses to the Dynamic and Static Models

Figure 31:
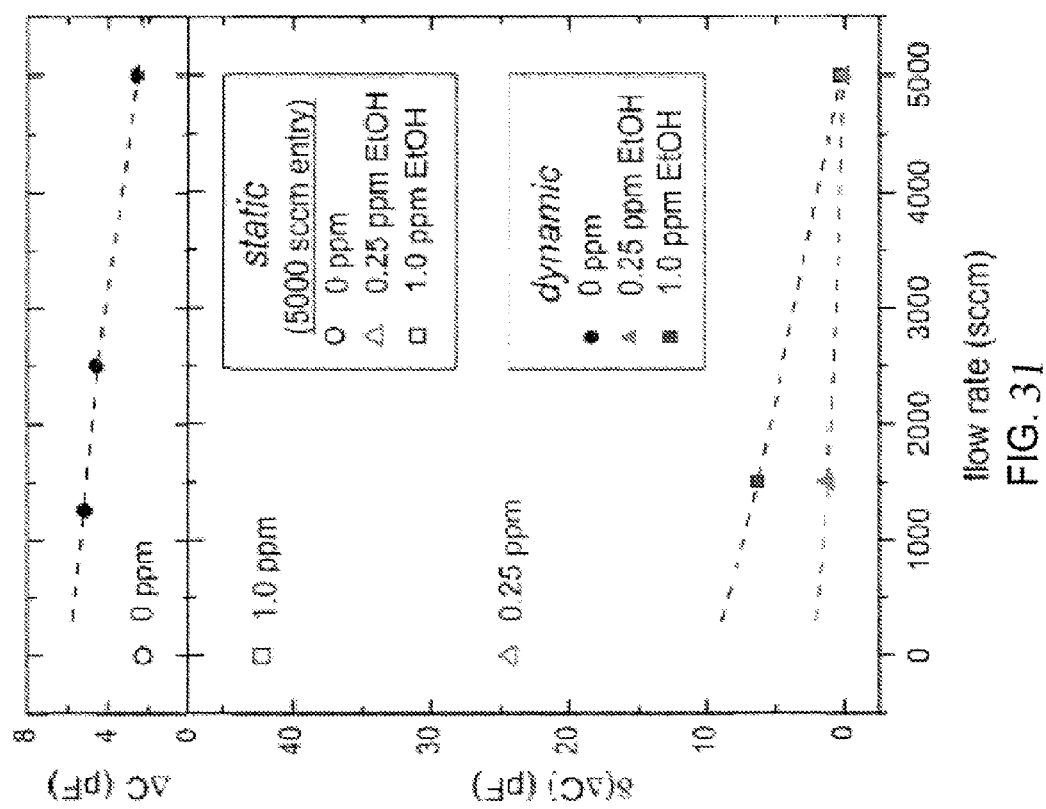
FIG. 31 shows Flow rate dependence of sensitivity for pure nitrogen and ethanol at 0.25 ppm and 1.0 ppm concentrations in $N_2$, under dynamic and static measurement conditions, showing considerably higher sensitivity for the latter.

As shown in FIG. 31, static and dynamic processes employed for $N_2$ and ethanol detection yield different results, with 0.25 and 1.0 ppm shown. For the response to pure nitrogen (upper panel), it can be seen that sensor response decreased in a nontrivial manner with increasing gas flow rate. It was concluded that the gas flow served to flush impurities from the array surface, with higher flow flushing more aggressively. Once largely flushed, at 5000 sccm, the response to pure $N_2$ was minimized to the ~2.5 pF value shown as the open circle. This flushing process was employed prior to the subsequent introduction of VOC at various concentrations. A similar reduction of net dynamic VOC response $\delta(\Delta C)$ with flow rate was observed (lower panel of FIG. 31). Thus, the dynamic process suppresses adsorption of target molecules into the porous dielectric, leading to reduced response with respect to that from static detection process (again, after gas entry at 5000 sccm to reach the desired concentration and zero flow rate after pressure reaches 1 bar within a few seconds). On the contrary, the static process may facilitate adsorption, and thus high response can be obtained. The latter is indicated for both 0.25 and 1.0 ppm by the open symbols. The nanoporous coax annulus thus facilitates enhanced capillary action under static flow conditions.

CONCLUSION

In various embodiments, the sensors described herein may be used to detect any suitable analyte, including organic and inorganic compounds. In some embodiments, the analyte may be a biomolecule. Detected biomolecules may include nucleic acids (DNA, RNA, etc.), proteins, polysaccharides, lipids, phospholipids, vitamins, hormones, metabolites, carbohydates, petides, heavy metal binding complexes, toxins (e.g., neurotoxins), etc.

As used herein the term "light" and related terms (e.g. "optical") are to be understood to include electromagnetic radiation both within and outside of the visible spectrum, including, for example, ultraviolet and infrared radiation. Portions of the electromagnetic spectrum referred to herein include are defined as followed: ultraviolet "UV" (wavelengths of 10-400 nm), visible (wavelengths of 380-760 nm), near infrared (wavelengths of 750-2500 nm), infrared (wavelengths of 750 nm-1 mm).

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A nanosensor, comprising a capacitor having a space between a first and second conductor of the capacitor, wherein:
the space is at least partially filled with a nanoporous dielectric material;
the nanosensor produces a signal in response to the capture of a target species in the space, wherein the capacitor comprises a nanocoaxial capacitor; the first conductor comprises an outer conductor of the nanocoaxial capacitor; and the inner conductor comprises an inner conductor of the nanocoaxial capacitor; a nanoporous dielectric material disposed between the inner and outer conductors;
wherein a space between the outer and inner conductors running along substantially the entire length of the inner conductor is substantially filled with dielectric material; and
wherein an unfilled nanocavity is located at one end of the nanosensor between the inner and outer conductors.

2. The nanosensor of claim 1, wherein the nanosensor is adapted to exhibit each of: a size-dependent physical selection of target species entering into the space; a selective capture of at least one of the target species within the space to at least one of the first and second conductors; and an electromagnetic shielding within the space such that a signal produced in response to the selective capture within the space is substantially undisturbed by a capture outside of the space.

3. The nanosensor of claim 2, wherein the size-dependent physical selection is performed by an opening to a nanocavity in the space which prevents species having a size greater than a critical size from entering into the nanocavity.

4. The nanosensor of claim 2, wherein the size comprises a distance between the first and second conductors.

5. The nanosensor of claim 1, wherein the signal produced in response to the capture comprises a change in capacitance of the capacitor.

6. The nanosensor of claim 1, comprising an etched nanocavity in at least a portion of the dielectric material.

7. The nanosensor of claim 1, wherein the nanoporous dielectric material substantially fills the space between the inner and outer conductors.

8. The nanosensor of claim 7 wherein the nanoporous material is configured to selectively capture the target species.

9. The nanosensor of claim 8 further comprising a nonporous dielectric coating on at least one of the inner conductor and the outer conductor.

10. The nanosensor of claim 9 comprising at least one active sensing element immobilized on a portion of the nanoporous dielectric material or the nonporous dielectric material, the at least one active sensing element is adapted to selectively capture the at least one target species.

11. The nanosensor of claim 10, wherein the at least one target species comprises an antigen; the at least one active sensing element comprises an antibody; and the selective capture comprises a specific binding of the antigen with the antibody.

12. The nanosensor of claim 1, comprising a layer of nonporous dielectric material located adjacent to the inner conductor.

13. The nanosensor of claim 1, comprising a layer of nonporous dielectric material located adjacent to the outer conductor.

14. The nanosensor of claim 1, wherein the nanoporous material has a porosity of at least 1% by volume.

15. The nanosensor of claim 1, wherein the nanoporous material has an average pore size of 500 nm or less.

16. A nanosensor, comprising a capacitor having a space between a first and second conductor of the capacitor, wherein
the space is at least partially filled with a nanoporous dielectric material;
the nanosensor produces a signal in response to the capture of a target species in the space, wherein the capacitor comprises a nanocoaxial capacitor; the first conductor comprises an outer conductor of the nanocoaxial capacitor; and the inner conductor comprises an inner conductor of the nanocoaxial capacitor, a nanoporous dielectric material disposed between the inner and outer conductors, wherein the inner conductor comprises a non-conductive nanopillar coated with a conductive layer.

17. A nanosensor, comprising a capacitor having a space between a first and second conductor of the capacitor, wherein the space is at least partially filled with a nanoporous dielectric material; the nanosensor produces a signal in response to the capture of a target species in the space, wherein the capacitor comprises a nanocoaxial capacitor; the first conductor comprises an outer conductor of the nanocoaxial capacitor; and the inner conductor comprises an inner conductor of the nanocoaxial capacitor, a nanoporous dielectric material disposed between the inner and outer conductors, wherein the outer conductor circumferentially surrounds the inner conductor, wherein the outer conductor comprises a cylinder and the inner conductor comprises a nanofiber.

18. A nanosensor, comprising a capacitor having a space between a first and second conductor of the capacitor, wherein the space is at least partially filled with a nanoporous dielectric material; the nanosensor produces a signal in response to the capture of a target species in the space wherein: the capacitor comprises a nanocoaxial capacitor; the first conductor comprises an outer conductor of the nanocoaxial capacitor; and the inner conductor comprises an inner conductor of the nanocoaxial capacitor, a nanoporous dielectric material disposed between the inner and outer conductors wherein: the outer conductor circumferentially surrounds the inner conductor wherein: the inner conductor is about 40 nm to about 200 nm in diameter; and the nanocavity is about 50 nm to about 2,000 nm in depth measured from the one end of the nanosensor.

19. A nanosensor, comprising a capacitor having a space between a first and second conductor of the capacitor, wherein the space is at least partially filled with a nanoporous dielectric material; the nanosensor produces a signal in response to the capture of a target species in the space wherein: the capacitor comprises a nanocoaxial capacitor; the first conductor comprises an outer conductor of the nanocoaxial capacitor; and the inner conductor comprises an inner conductor of the nanocoaxial capacitor, a nanoporous dielectric material disposed between the inner and outer conductors, wherein the outer conductor circumferentially surrounds the inner conductor, wherein the inner conductor is in electrical contact with a metal layer deposited on at least a portion of a substrate and the inner conductor is elongated in a direction substantially perpendicular to the substrate.

20. The nanosensor of claim 19, wherein the outer conductor is not in electrical contact with the metal layer.

21. A sensor array comprising a plurality of sensors, wherein each sensor comprises a nanosensor, comprising a capacitor having a space between a first and second conductor of the capacitor, wherein the space is at least partially filled with a nanoporous dielectric material; the nanosensor produces a signal in response to the capture of a target species in the space wherein the nanoporous material has an average pore size of 500 nm or less, wherein the inner conductor of at least one sensor is not in electrical contact with the inner conductor of at least one other sensor.

22. The sensor array of claim 21, wherein the array comprises an ordered pattern of the sensors on a substrate.

23. The sensor array of claim 22, wherein the ordered pattern comprises a hexagonal pattern.

24. The sensor array of claim 21, further comprising an insulative material disposed between the outer conductors of adjacent nanosensors.

25. A method of using a nanosensor to detect a presence of a target specie, comprising: transmitting electromagnetic waves through a nanoporous dielectric medium disposed between a first and second electrode of the nanosensor, wherein the first and second electrodes have an inter-electrode spacing of no more than about 500 nm and the waves are substantially shielded between the first and second electrodes; and monitoring for a change in the electromagnetic waves based on a change in a dielectric constant between the first and second electrodes, wherein the change in the dielectric constant corresponds to a selective capture of a target specie between the first and second electrodes and wherein the electromagnetic waves comprise an oscillating electromagnetic field; the step of monitoring comprises using at least one of Impedance Spectroscopy or Time Domain Dielectric Spectroscopy to measure at least one of impedance or dielectric constant between the first and second electrodes as a function of frequency of the field; and the frequency is swept over a range of about 1 Hz to about 10 GHz.

26. The method of claim 25, wherein the frequency is swept over a range of about 1 Hz to about 10 MHz.

27. The method of claim 25, wherein the frequency is swept over a range of about 1 MHz to about 10 GHz.

28. The method of claim 25, wherein the electromagnetic waves comprise visible light.

29. The method of claim 25, wherein: the first and second electrode each comprises a coplanar layer of a nanoscale coplanar transmission line; and the medium comprises a dielectric layer disposed between the coplanar layers.

30. The method of claim 25, wherein the target species comprises a biomolecule.

31. The method of claim 25, wherein the biomolecules comprise at least one selected from the list consisting of: a nucleic acid, a protein, a polysaccharide, a lipid, a phospholipid, a vitamin, a hormone, a metabolite, a carbohydrate, a peptide, a heavy metal binding complex, and toxins.

32. The method of claim 25, wherein the target species comprises a volatile organic chemical.

33. A method of using a nanosensor to detect a presence of a target specie, comprising transmitting electromagnetic waves through a nanoporous dielectric medium disposed between a first and second electrode of the nanosensor, wherein the first and second electrodes have an inter-electrode spacing of no more than about 500 nm and the waves are substantially shielded between the first and second electrodes; and monitoring for a change in the electromagnetic waves based on a change in a dielectric constant between the first and second electrodes, wherein the change in the dielectric constant corresponds to a selective capture of a target specie between the first and second electrodes and wherein: the electromagnetic waves are transmitted through the medium in a transverse electromagnetic mode; and the step of monitoring comprises measuring at least one of intensity or wavelength of the transmitted waves.

34. A method of using a nanosensor to detect a presence of a target specie, comprising transmitting electromagnetic waves through a nanoporous dielectric medium disposed between a first and second electrode of the nanosensor, wherein the first and second electrodes have an inter-electrode spacing of no more than about 500 nm and the waves are substantially shielded between the first and second electrodes; and monitoring for a change in the electromagnetic waves based on a change in a dielectric constant between the first and second electrodes, wherein the change in the dielectric constant corresponds to a selective capture of a target specie between the first and second electrodes and wherein: the first electrode comprises an outer conductor of a nanoscale coaxial transmission line; the second electrode comprises an outer conductor of the nanoscale coaxial transmission line; and the medium comprises a nanoporous dielectric layer disposed between the inner and outer conductors.

35. The method of claim 34, wherein: the nanosensor comprises a nanocavity formed between the inner and outer conductors.

36. The nanosensor of claim 1, wherein the nanoporous dielectric material comprises at least one of $Al_2O_3$, $SiO_2$, $MgO$, $Si_3N_4$, $TiO_2$, and a non-conductive polymer.

* * * * *